United States Patent [19]

Margrey et al.

[11] Patent Number: 5,366,896
[45] Date of Patent: Nov. 22, 1994

[54] ROBOTICALLY OPERATED LABORATORY SYSTEM

[75] Inventors: Keith S. Margrey; Robin A. Felder; James C. Boyd, all of Charlottesville; J. William Holman, Earlysville; Jonathan H. Roberts, Charlottesville; John Savory, Keswick; Antonia Martinez, Charlottesville, all of Va.

[73] Assignee: University of Virginia Alumni Patents Foundation, Charlottesvile, Va.

[21] Appl. No.: 739,204

[22] Filed: Jul. 30, 1991

[51] Int. Cl.$^5$ .................. G06F 15/42; G01N 1/00
[52] U.S. Cl. .................. 436/48; 436/43; 436/47; 436/50; 436/55; 436/807; 422/62; 422/63; 422/64; 422/67; 422/68.1; 422/103; 422/104; 422/105; 422/107; 364/497; 364/500
[58] Field of Search .................. 422/63, 67, 100, 102, 422/104, 64, 62, 68.1, 103, 105, 107; 436/43, 48, 49, 50, 54, 55, 47, 807; 364/497, 500

[56] References Cited

U.S. PATENT DOCUMENTS

| | | | |
|---|---|---|---|
| 3,871,832 | 3/1982 | LeBlanc | 422/104 |
| 4,670,219 | 6/1987 | Nelson et al. | 422/63 |
| 4,676,951 | 6/1987 | Armes et al. | 422/65 |
| 4,708,886 | 11/1987 | Nelson | 422/72 |
| 4,781,891 | 11/1988 | Galle et al. | 422/64 |
| 4,835,707 | 5/1989 | Amano et al. | 364/497 |
| 5,080,864 | 1/1992 | Shaw | 422/62 |
| 5,158,895 | 10/1992 | Ashihara et al. | 436/526 |

Primary Examiner—James C. Housel
Assistant Examiner—Long V. Le
Attorney, Agent, or Firm—Sheldon H. Parker

[57] ABSTRACT

The present invention relates to an integrated analytical system which includes a plurality of remote laboratories and a central monitoring station. The remote laboratories include a specimen analysis member and a plurality of peripheral devices. The central monitoring station includes a computer for controlling predetermined functions of the peripheral devices. A local area network provides communication between each of the remote laboratories and the central monitoring station. A computer interface provides bi-directional communication between analytical instruments, robots and peripheral devices and a computer. The system employs a robot which is responsive to computer commands and capable of performing mechanical functions.

The mechanical functions include manipulating an analytical instrument, transporting the specimens to be analyzed through a variety of locations, and the manipulation of the container in which the specimen is housed.

7 Claims, 13 Drawing Sheets

ROBOTICALLY OPERATED LABORATORY SYSTEM

BACKGROUND OF THE INVENTION

1. Field of the Invention

The invention relates to an integrated analytical system which includes a remote laboratory and a central monitoring station, and more particularly to a robotic system for operating a remote laboratory.

2. Description of the Prior Art

Dramatic improvements in industrial productivity and quality have been achieved with the application of robotic technology. Spinoffs of this technology that will impact everyday living are rapidly emerging as exemplified by home robots for housecleaning, lawn-mowing and fast food robots. Against this backdrop hospitals and hospital laboratories across the country are beginning to consider the benefits of robotic automation. Health care traditionally has been a difficult marketplace for automation because of the complexity of the procedures and the potential risks to human life if an error were to occur. Nevertheless, exciting medical applications such as the use of robots as assistants in surgical procedures have recently been described. Robots will have a significant impact on medical care by eliminating mundane chores, reducing the exposure of personnel to AIDS, and lowering labor costs.

In confronting increasing pressure to reduce the cost of providing analytical results, many laboratories have centralized their services to conserve resources. By consolidating services, expensive equipment has less idle time and labor is used more cost effectively. However, centralization may adversely affect the sample-to-result turnaround time by increasing the distance of the centralized laboratory from the origin of the specimen. Frequently, analytical results must be obtained in a short time to provide information for rapid assessment of a situation so that corrective actions may be taken. In medical care, for example, the clinical state of a critically ill patient must be assessed and corrected before a life threatening condition occurs. Similarly, in the outpatient clinic, providing results of blood analysis to physicians while the patients are still in the physicians' office is highly desirable because it obviates the need for a return appointment to discuss abnormal laboratory results. In industrial process control, real-time monitoring of the progress of chemical reactions by on-site analytical techniques prevents dangerous conditions or loss of products.

Up to now, improvements in the turnaround of results have been obtained either by dedicated rapid specimen transportation systems or by simplifications of analytical techniques that make the specimen analysis faster. Pneumatic tube systems, mobile carts, and human messengers have been used with some success to transport specimens rapidly to the central laboratory. However, these systems are expensive to install and maintain; and in some facilities retrofitting of pneumatic tube systems or cart systems is not possible.

Additionally, there has been much interest in simplifying analytical instruments so that non-technical employees can perform complex analyses. For example, physician's office laboratories have been equipped with a new generation of analyzers that can provide rapid results with minimal operator training. Unfortunately, the results provided by many of these simple analyzers are not as precise or accurate as the results obtained in the centralized laboratories. Furthermore, the adequacy of quality control has frequently been overlooked. New pending federal regulations require that only trained medical technologists perform laboratory tests. These regulations will prohibit the physician or paramedical personnel (e.g. nurse or respiratory therapist) from performing clinical laboratory tests.

By definition, a robot is any machine that can be programmed to perform any task with human-like skill. Practically, the term robotics refers to programmable devices that can perform a variety of skilled actions by using a combination of mechanical and electronic components. Robots are often considered simply a mechanical extension of the computer. The greatest asset of a robot is that it can be configured to perform a multiplicity of tasks and therefore should wear out before it becomes outmoded. Devices designed for only one repetitive task are referred to as "hard automation," e.g., auto-samplers, pipetters, and all other instrumentation with limited mechanical capabilities or restricted programability.

Laboratory robots can take many forms, however, three basic configurations of robots are predominately used in the clinical laboratory environment, although many other robots are available that are suitable for the laboratory environment.

Cartesian robots are devices with three linear degrees of freedom. Items can be moved about in a three-dimensional (x,y,z) space, but not rotated. Cartesian robots are the basis for sampling devices in many automated analyzers. However, cartesian robots have found more versatility in the clinical laboratory as pipetting stations, designed to perform many liquid-handling activities.

An example of a cartesian robot would be the Biomek pipetting station (Beckman Instruments, Brea, Calif.) where the robot can be programmed to perform various liquid-handling protocols. Cartesian robot-pipetting stations allow placement of a pipette tip at any point in space, within ~0.2 mm repeatability, with the capability of aliquoting and diluting specimens and dispensing reagents. Cartesian robot-pipetting stations have as their principal components microprocessor-controlled stepping motors that drive liquid-handling syringes, pipetting arms, and in some units movable sample trays.

The Biomek is a hybrid robot in that it has a series of interchangeable hands that allow it to vary its pipetting capabilities. However, the Biomek cannot mechanically manipulate test tubes. In addition, it comes equipped with a built-in spectrophotometer. The Biomek and other similar pipetting stations can be programmed to perform other useful liquid-handling chores such as washing an antibody-coated bead, or rinsing the wells in a microtiter plate.

Recently the Biomek has been configured to perform a monoclonal solid-phase immunoenzymatic assay for carcinoembryonic antigen (Hybritech Inc., San Diego, Calif.). Because of the Biomek's built-in spectrophotometer, the entire assay, including bead washing and data reduction, is handled automatically.

There are several examples in the clinical laboratory of the use of pipetting stations to perform analytical procedures. Brennan et al demonstrated the use of the Tecan Sampler 505 (Tecan AG, Hombrechtikon, Switzerland) in the screening test for anti. HTLV-III antibodies. The procedure required placing a patient's plasma sample in a rack, after which the pipetting station diluted the plasma 441-fold. A barcode reader and pipette washer were retrofitted to the device to positively identify patients and to eliminate carry-over, respectively. The system operated at approximately the same rate as a trained medical technologist but demonstrated better precision and allowed technologists to perform other tasks.

The cylindrical robot, exemplified by the Zymate robot (Zymark Corp., Boston, Mass.) works in a cylindrical performance envelope. The four degrees of freedom exhibited by cylindrical robots (base rotation, elevation, movement in and out of a plane, and wrist roll) are usually sufficient for most laboratory operations. The major limitation of these robots is the lack of wrist pitch, which would be useful for getting in and out of tight places. Additional flexibility in task performance is obtained by programming the robot to use a series of interchangeable hands (a feature patented by Zymark Inc.). Hand and finger orientation is determined by potentiometric servo motors that allow the robot to "sense" its orientation at all times. This arm is a popular choice for simple repetitive tasks and has been used successfully for many sample-preparation protocols, both in the clinical laboratory and in the pharmaceutical industry.

The use of a cylindrical robotic arm to produce an automated blood-typing system that would be affordable to most laboratories has been investigated. The system consists of an indexing rack for samples, which are identified by a barcode reader. After significant development over several years, the system was described again, with throughput increased from 40 to 104 samples per hour. The device was later commercialized by Microban (Dynatech Laboratories, Chantilly, Va.). The success of robotic applications in the blood bank is due to the production line nature of blood typing. Laboratory services that support blood banks require many repetitive analyses before the blood can be used for transfusion. It has been estimated that, in 1984, 12 million units of whole blood were collected in various medical centers, each unit of which required ABO and Rh typing. The blood-typing process has been automated by some manufacturers, but these units cost greater than $100 000 and so are not accessible to most regional hospitals with small transfusion volumes. Robotic arms not only are less expensive than a dedicated blood-typing instrument but also can be reprogramed when the laboratory's needs change.

The cylindrical robot has been used in the clinical chemistry laboratory at the Cleveland Clinic Foundation to prepare samples for an HPLC method in a complex series of steps: sample extraction, separation of liquid phases, and injection. These investigators incorporated several Zymate robotic systems into a laboratory for the analysis of antidepressants. Medical technologists were needed to prepare the reagents, to place necessary supplies at the designated locations within reach of the robot, and to evaluate the quality of the final results. The robotic laboratory was placed under a fume hood to eliminate any toxic fumes originating from extracted samples during the evaporation process. The robot completed the drug extractions and made the sample injection into the chromatograph by using a specially designed injection hand. For several years these robots have been performing their repetitive tasks with only minor malfunctions.

The use of a robot to perform preparative immunologic precipitations, with final placement of the samples into a rotor for subsequent analysis has been recently reported. This robotic system, which consisted of a Zymate robot and a Cobas-Bio rotor (Roche Diagnostics, Nutley, N.J.), was the first reported system to combine a clinical analyzer and a laboratory robot. However, placing the rotor in the analyzer and transferring the data to the laboratory computer were performed manually.

The Vancouver General Hospital has automated a highly complex steroid-receptor analysis, using a Zymate robotic system. The estrogen receptor assay ordinarily is a manual procedure, involving many critical steps such as centrifugation, incubation, and subsequent placement of completed samples in scintillation vials. In the automated procedure, the incubation water bath, centrifuge, and supply and reagent stations are placed in a circular pattern around the robotic arm. The reagents, which are particularly labile in this assay, are kept cold in an ice bath. Finished samples are added to scintillation vials by the robotic arm. Because more than one rack of vials is produced in a single uninterrupted robotic procedure, the scintillation vial racks are placed in a tiered holder to allow the robot access to two racks.

A Zymate robot, fitted with exchangeable pipetter hands, has been used to dilute and transfer samples for blood grouping in the blood bank. The robot, configured as a pipetting device, was also used to orient samples for barcode reading. After the robot had performed the liquid handling, a human operator proceeded with additional manual aspects of the test. As discussed earlier, many blood-bank analytical methods are relatively simple and are used in sufficient numbers to warrant a dedicated analyzer.

The most versatile robot available to the clinical laboratory is the articulating robot in that it offers more degrees of freedom than either the cartesian or the cylindrical robots. The articulating robot has shoulder, elbow, and wrist joints, rotating on a pivoting base. Furthermore, the robot has wrist pitch-and-roll, as well as wrist yaw maneuvers, that allow access to areas often difficult to reach on analytical instruments. Positional accuracy of 0.5 mm or better is obtained by using optically encoded discs that must be set by nesting to a home or zero location each time the robot is turned on.

A recent example of a sophisticated articulating robot is from Cyberfluor Inc. (Toronto, Ontario, Canada). The Cyberfluor robot has a high degree of flexibility, with five degrees of freedom. Sample processing is currently the rate-limiting step in most clinical laboratories. Using a robot in conjunction with a clinical centrifuge allows processing of samples as they enter the laboratory. One advantage of an articulating robotic arm is its ability to reach over the rim and into a clinical centrifuge to retrieve samples. For a cylindrical robot to perform this task requires use of a custom-altered centrifuge or a custom-made robotic hand. A novel serial centrifuge has also been developed to separate sera or plasma from formed elements in the blood-collection tube. The single-tube centrifuge will eventually be incorporated into a robotic sample-handling system that should not only speed up laboratory productivity but also reduce risk of exposure to AIDS and hepatitis.

Articulating robots are also beginning to be used in the blood- bank laboratory. One manufacturer of blood-banking automation (Flow Laboratories, McLean, Va.) markets a robot interfaced to various microplate-handling devices (pipetters readers, washers, centrifuges). The entire device (the IROBAL) is enclosed in a protective hood, obviously designed to reduce operator exposure to contaminants.

Establishing control of robot motion to mimic the smooth movement of the human arm with a high degree of repositional precision is a difficult problem addressed by the science of kinematics. Kinematics are applied to the robot in three levels of complexity. First, trajectory planning determines position, velocity, and acceleration for each movement made by the robotic manipulators. Second, inverse kinematics are applied to translate the movements required in the coordinate system into the joint movements required by the particular geometry of the robot being developed. Finally, inverse dynamic equations are applied to establish how the robot moves in response to various applied torques and forces. Each movement of the robot is represented, therefore, by a set of remarkably complex equations, the implementation of which has fortunately been simplified through the use of high-level computer languages.

Robot locomotion is a general term applied to all types of robot movement in which the robot can venture away from a fixed point. Locomotion imparts another degree of freedom to the robot but also allows an increase in the variety of hardware with which a robot can interact. Robots can be made mobile by several methods. Robotic arms can be attached to linear tracks or to a mobile cart. In the case of a mobile cart, the portion of the robot imparts mobility is considered an "Automated Guided Vehicle" (AGV). AGVs are either equipped with an automatic onboard guidance system or follow a path on the floor wall or ceiling. Guidance is provided through various sensors, e.g., infrared, video, magnetic, or simple light sensors for reflective tape paths. Equipping AGVs with a robotic component produces a mobile robot. Some robots are being designed to have human-or animal-like gait, so that they may climb stairs, for example. The study of bringing human-or animal-like gait to robotic machines is called bionics.

A recent improvement in robot locomotion is the use of linear tracks. The robotic arms can travel the length of a linear track, either upright or upside down, with positional precision of 0.5 mm. This concept has altered the evolution of laboratory design from circular tables with the fixed robot in the middle, back to the classic laboratory bench stretched along the perimeter of the room. Ergonometric laboratories are now possible, such that either technologists or robots can operate the instruments. Robots that can travel the length of a laboratory bench have performance envelopes (the areas in which the robot can perform useful work) that resemble an elongated hemisphere of a doughnut.

Several attempts at robot locomotion have been tried in the clinical setting. Computer-driven vehicles that move about the hospital corridors picking up specimens and delivering them to the main laboratory have been popularized. Similarly, robotic vehicles that move about the laboratory, returning empty specimen racks to the central specimen-receiving area of the lab have also been designed. Mobile robots that can negotiate the corridors of a hospital for specimen delivery have been investigated by Transitions Research Corp. (TRC, Danbury, Conn.). Unlike many mobile robots, the TRC Helpmate does not rely on a guide affixed to the floor. The TRC mobile robot is equipped with infrared, ultrasonic, and vision sensors to acquire information about the environment. With the aid of a preprogrammed knowledge base of the hospital layout, the robot arrives at its destination without colliding with patients or objects in its path.

The mechanical performance of the robot can be enhanced by adding sensor technology on the hands or joints of the robot. Various mechanical and electronic sensor systems may be used, e.g., computerized imaging systems to check for sample integrity and container position for access by a robot. Currently, video systems allow a robot the greatest degree of spatial resolution. Several investigators are looking at the feasibility of tactile sensing in the fingertips of robotic fingers. Tactile sensing approaching that of the human finger is in the foreseeable future.

The advantage of sensor technology is the ability of the robot to respond to changes in the analytical method. With proper sensor technology, closed-loop operation of robots becomes a possibility. Analytical data can be checked by the robot's host computer, which is equipped with an expert system, and corrective measures such as sample re-analysis can be initiated if necessary. Many of these enhancements to increase the intelligence of the robotic system have not been examined in the clinical laboratory setting. However, both the Zymate and Cyberfluor robots have fingers that can sense the presence of absence of objects in their grasp. This feature is helpful if test tubes or syringes are dropped inadvertently during a procedure.

Perhaps the single most important factor that has stimulated the introduction or robotics into the clinical laboratory has been the development of high-level robot programming languages with English language commands. For example, the simple command GOTO MIXER initiates an intricate sequence of steps to drive the robotic arm to the mixing device. Several interfaces away from the user's command, the software generates electronic signals to the robot's motion-control mechanism to coordinate a smooth movement arc that terminates at a precise location near the mixer. Complex algorithms involving robot kinematics translate computer machine-code into signals that control the acceleration after commencing the movement and the deceleration before the robotic arm stops at the mixer. Furthermore, to avoid spilling any liquid, the robotic fingers are held parallel to the work surface throughout the complex series of movements. Elaborate procedures can be developed by combining a series of simple commands, which are programmed and tested individually. The robot can be instructed to pause in a procedure, examine the status of a sensor or instrument, and then proceed through a choice of subsequent programs, depending on the outcome of the test. Programmed intelligence of this sort allows highly adaptive systems for performing many assays.

The integration of the various levels of programing language and the input and output ports of the robotic system are controlled by a high-level robot language. Future robotics software is being directed toward standardization and modularization of the basic operations performed in the clinical laboratory: sample manipulation, liquid handling, separation, conditioning, weighing, measuring, reporting, and storing by use of a modular approach. High-level robotic control languages will reduce the time necessary for assay automation. Intellibotics (Oxnard, Calif.) has used a computer graphics interface to simplify writing robot programs. The programs can be implemented graphically before being used to actually run the robot. Modular programming will allow rapid integration of several basic operation modules into a complete assay procedure with appropriate instrumental status checks. Standardization of interfaces with peripheral hardware (i.e., centrifuge, mixer, and pipetter) will be essential for the rapid incorporation of various sample manipulations in the development of robotically controlled assays.

The term user interface implies a software design that makes many of the complex codes for robotic motion control and data input/output transparent to the user. One should be able to use simple English language commands to train a robot to perform any task within its mechanical performance envelope. Perkin-Elmer Corp., Zymark, and Cyberfluor, Inc. have developed simple-to-use robotic-control languages accessible to most computer programmers. Unfortunately, no robot vendor has simplified all aspects of robotics software. In particular the programing associated with communication with other devices remains incomplete.

The use of digitized images (e.g., a picture of the robot and peripheral equipment on the touch screen computer monitor) should allow the user to point to destinations in the picture to which the robot will then physically move. Graphic image inter-faces should reduce the time needed to train laboratory technologists to implement new procedures. Training a laboratory robot to move to specific coordinates on the robotic work-surface can be effected through either a teaching pendant (a group of switches on a remote control) or directly through the robotic keyboard. The robot is positioned by the trainer to a certain location and then the coordinate is entered into the computer via a switch or press of a key on the keyboard. A second coordinate may then be entered in a similar manner. Using simple commands from the keyboard, one replays the coordinates and the robot will move as instructed. Because robots are inherently blind and without tactile senses, they will collide with any obstacles in the path between the two points. Thus trainers must include a third point in the robot program that will allow a collision-free trajectory. A recent innovation in robotic training is the "limp mode" used by the CRS robot marketed by Cyberfluor. In this mode a robot trainer can simply grasp the robot arm and move it to a location. A press of a button automatically enters the position into the robot software, where it will be repeated once the software routine is started. Some future prospects for robot training may couple hand movements with digitized images of the work surface. The monitor will display a picture of the robotic laboratory from a choice of perspectives (e.g., top or side view). A trainer then moves his or her hands on the computer monitor in the path the robot will take during the execution of a procedure. Imaginative methods to train robots will simplify and accelerate the programming of new procedures.

Efficient robotic laboratories use procedures that are reduced to LUOs (laboratory unit operations); these are used repeatedly or recombined in a different order as laboratory procedures change. Creating new procedures is simplified by the modular design of the robotic laboratory. The most basic LUOs encompass the moving of items around the laboratory bench, or manipulation. A subcategory of this LUO is robotic interaction with a matrix. Many designers of robotic software have simplified the steps necessary to define and interact with a matrix, such as a test-tube rack, because retrieving samples is universal to almost all procedures. To be successful, implementation of laboratory robotics requires careful planning, attention to detail, and specialized training of staff and skilled support personnel.

Currently there are only a handful of companies that sell robotic devices for laboratories. Only a few actively market to the clinical laboratory. Of those few, none offer off-the-shelf systems that can perform a clinical laboratory test or process a blood specimen. Commercial robotic devices require a knowledge of computer programming and electronic interfacing as well as analytical assay design by the end user. Furthermore, the difficulty in designing robotic systems is complicated by the lack of engineers trained in all the disciplines required for the clinical laboratories. Zymark normally sells turnkey robotic systems, however, for $50-90,000. Recently it has added a line of simple robotic workstations selling for $5-20,000 that should have utility in clinical toxicology and drug screening laboratories.

Nationally, there has been an increasing trend toward performance of selected laboratory tests using whole blood analyzers located close to the critical care patient's bedside. This approach has the advantage of providing an average test turnaround time of 5 minutes. Up to now, this testing generally has been performed by individuals with minimal training in medical technology. Newly instituted Joint Commission of the American Hospitals Organization and College of American Pathologists ancillary testing regulations require a similar level of quality control as that required by larger laboratories offering similar services. Because most personnel working in intensive care settings have neither the experience nor desire to perform rigorous quality control, this function will be assumed by trained medical technologists from the clinical laboratory in many centers. Staffing these satellite whole blood analysis laboratories with medical technologists will result in much higher costs unless an automated alternative can be developed.

The problems outlined above have been overcome through the instant invention which serves as an alternative to the centralized laboratory by providing analytical services near to where the specimen is obtained without substantially increasing the need for additional labor. The instant invention consists of a method to control commercially available analytical instruments via a computer interface linked to novel computer software. The analytical, electronic and mechanical performance of the laboratory is monitored remotely through an electronic, radio or optical link.

Robotic technology could also find a use in laboratories peripheral to the medical center. The estimated 100,000 physicians office laboratories in the United States perform approximately 25% of total laboratory testing. Besides being profitable for physicians, the major incentive for performing laboratory tests in the physicians office is the rapid turnaround. Rapid analysis results in prompt initiation of treatment, reduction in patient stress, and a reduction in repeat office visits. The major criticism of physician office testing is the lack of adequate quality control. Proposed regulations recently issued by the Health Care Finance Administration (HCFA) to carry out the Clinical Laboratory Improvement Act of 1988 (CLIA) require each physicians' office laboratory to monitor and document quality assurance, proficiency testing, safety, and instrument maintenance. Employees must all meet the qualifications set forth by the Department of Health and Human Services and be involved in a continuing education program. Robotics can provide many physicians with the laboratory services they require on site yet put the responsibility of monitoring quality, hiring and training qualified personnel, and maintaining instruments in the hands of a local commercial laboratory or hospital. Connection of the remote laboratory in the physicians office to the commercial laboratory could be through a telephone line.

Additional uses can be in the field of microbiology, as many microbiology tests have been reduced to simple devices which can be easily handled by robot. The remote laboratory can be configured to also include microbiology analyses.

The next major medical frontier is the use of molecular biology for identification and diagnosis of genetic-based diseases. Once the aberrant gene is identified, gene therapy eventually may allow replacement of defective genes. Molecular biology is already providing many new tests which are being used to identify various genetic diseases (e.g., cystic fibrosis and sickle cell anemia). There has been a rapid expansion in the number and variety and simplicity of analyses based on genetic markers. The remote laboratory can be used for rapid, on site testing based on molecular biology.

Hematology analyses are usually performed on heparinized whole blood specimens. The heparin (usually in the specimen tube before the blood is drawn into it) serves as an anticoagulant so that the blood remains free flowing. Hematologists are usually concerned with analyses such as white blood cell concentration, the number of subpopulations of white cells, red cell concentration and morphology gradients, and platelet concentrations, to name a few. Hematology instruments have become fully automated in the last several years, therefore, they are well suited to incorporation into the Remote Laboratory Under Central Control.

U.S. Pat. No. 4,670,219, Nelson et al, discloses an analysis system having a first region in which sample materials are stored at an appropriate storage temperature and an analysis region which is maintained at a controlled and stabilized temperature higher than the temperature of the first region. The transfer mechanism includes a liquid handling probe that is mounted on a probe transport carriage, and a drive for moving the transport carriage between the first and second regions. The transport carriage includes a storage chamber connected to the liquid handling probe, thermal energy supplying means in heat exchange relation with the storage chamber, and thermal sensor means carried by the transport carriage. Means responsive to the thermal sensor supply thermal energy to the transport carriage to maintain the storage chamber at substantially the same temperature as the analysis region.

U.S. Pat. No. 4,676,951, Armes et al, discloses an automatic system for analyzing specimens which have been selectively treated. The specimens are arranged in a plurality of specimen trays with each tray containing a plurality of specimens. A work station selectively moves the trays one a time from the tower to selectively deliver reagent or analyze the specimen in the tray. A control system is adapted to sequentially actuate the work station to properly sequence the system so that the reagents are administered to the respective specimen and the specimen have been analyzed after a desired incubating period.

U.S. Pat. No. 4,781,891, Galle et al, discloses an automatic analyzing apparatus for effecting chemical analyses for various sample liquids such as blood, urine and the like, comprising a sample delivery pump for metering a sample liquid into a reaction cuvette, a reagent delivery pump for delivering to the reaction cuvette a given amount of a given reagent selected from a plurality of reagents contained in a reagent cassette, to form a test liquid, a feed mechanism for successively supplying reaction cuvettes along a circular reaction line, a plurality of photometering sections arranged along the reaction line for effecting a plurality of measurements for each test liquid at different time instances to produce a plurality of results.

Although the use of robotics in medical facilities appears to be beneficial to all, health care providers have been cautious in their approach to robotic technology. Much of the delay in robotic use in hospitals has been a result of the lack of off-the-shelf systems, the wide variety of electronic and mechanical standards existing in clinical instrumentation, a shortage of research and development dollars in hospitals, the necessity for manufacturers to have Food and Drug Administration (FDA) approval to sell medical devices, and the lack of combined skills necessary to implement robots in clinical laboratories.

A major difficulty facing implementors of robotics in health care is the lack of electronic communications, software, or hardware standards in clinical instruments. Many clinical laboratory analyzers, for example, operate as discreet devices with only a RS-232C port for the output of analytical data. Robotic operation of instruments requires an electronic communication standard that allows many of the instrument electronic functions be accessible to the robot host computer. For example, an analyzer which has been internally programmed to self-calibrate on a predetermined schedule should not initiate a calibration cycle at the same time as an irreplaceable medical specimen is being injected into the sampling port.

Many of the injection ports or aspiration needles built into clinical analyzers are simply inaccessible to most robotic devices. This necessitates that each site redesign a separate sample introduction mechanism which is compatible with the instrument hardware.

Although several robots are available for use in the laboratories today, existing systems do not appear to offer much flexibility in handling multiple tube types or the wide variety of containers used for medical specimens. Laboratories may either design their laboratories around the fixed automation inherent in the large integrated systems, or integrate specimen processing modular work-stations into the flow of their existing laboratories. All of these robotic specimen processing systems require technologist supervision and so must be placed directly into the clinical laboratory.

The laboratory disclosed herein is an alternative model to the large centralized laboratory facility. One of the major disadvantages of centralized laboratory facilities is the extended length of time to obtain analytical results. Long turnaround time can result in compromised patient care, particularly in intensive care units. A high cost specimen transportation system has been the traditional method to reduce specimen transit time.

SUMMARY OF THE INVENTION

The present invention relates to an integrated analytical system. The system includes a plurality of remote laboratories and a central monitoring station. The remote laboratories includes a specimen analysis member and a plurality of peripheral devices. The central monitoring station includes a computer for controlling predetermined functions of the peripheral devices. A local area network provides communication between each of the remote laboratories and the central monitoring station. The local area network can be hard wired or employ telephone communication. The network, for example, can employ an optical link or a radio link.

A universal electronic interface enables computer communication with the specimen analysis member and the peripheral devices.

Each remote laboratory includes a user interaction station, which includes a computer and a monitor. Advantageously, the monitor has a software controlled touch sensitive screen. The touch sensitive monitor including means to display a plurality of images and the touching of a image by a user, causes the monitor to display requested information. The information can be patient data, the results of analytical tests, and the like. The images also serve to facilitate the control of the remote laboratory. A computer interface provides bi-directional communication between analytical instruments, robots and peripheral devices and a computer.

The system employs a robot which is responsive to computer commands and capable of performing mechanical functions. The mechanical functions include manipulating an analytical instrument, transporting the specimens to be analyzed through a variety of locations and the manipulation of the container in which the specimen is housed.

A specimen holding or storage device, is provided which includes an indexing rack and mechanical means for rotatably moving the indexing rack, and a plurality of sensors. The sensors function to determine the position of the indexing rack so that the rack can be positioned to present empty specimen holding areas to the robot. The indexing rack is located within a temperature regulated region. Refrigeration provides the temperature regulation of the indexing rack region at a subambient temperature in order to preserve integrity of the specimen. Advantageously, mixing means are employed to provide a uniform consistency of the specimen. Movement of the specimens within the indexing rack through rotation of the rack can provide the required mixing of the specimens. The storage device includes a region in which the specimen is placed in an atmosphere of inert gas, such as nitrogen or argon, in order to isolate the specimen from contamination by oxygen and carbon dioxide present in room air.

The process of the instant invention for analyzing a sample specimen comprising the steps of:

a- placing a first sample on a sample receiver station, b- robotically transferring the sample from the sample receiver station to a storage unit, c- determining the next available position within the storage unit based on the storage unit computer database's information on position availability within the storage unit, d- placing the first sample in the next available open position, the storage unit preferably being maintained at a temperature substantially below ambient temperature in order to preserve the sample and the sample being agitated while in the storage unit in order to maintain the sample in a uniformly mixed state, e- searching the computer database's information relating to sample priorities of samples stored within the storage unit, f- determining sample in the storage unit with the highest priority, g- running a computer check of an analytical instrument to determine if the instrument is ready to analyze a sample, h- robotically transferring the highest priority sample, as determined in step (f), from the storage unit to a container processing member, i- robotically placing the highest priority sample in the decapper to unseal the specimen container. The decapping device preferably includes sensor means to determine if the cap has been successfully removed from the specimen container.

j- repeat step (f) until the instrument is ready to receive a sample, h- when the instrument is ready to receive a sample, as determined in step (j), the instrument is prepared to receive a sample, and the sample is processed in preparation for transfer to the analytical device and is robotically transferred to the analytical device, i- docking the sample the instrument, j- delivering an aliquot of the sample into the instrument, k- determining when the instrument has enough sample and removing the sample from the instrument, l- the sample is delivered from the analytical instrument to a bubble remover which aspirates air out of the specimen by applying negative pressure to the open end of the specimen container, m- robotically delivering the sample to the decapper, n- robotically transferring the sample from the decapper to the storage unit, preferably transferring the sample to the same position within the storage unit from which it was originally removed, o- analyzing the sample in the instrument, p- transferring the results from the analyzing of the sample to a computer at a remote location, through the use of a computer data transfer link, q- searching the computer data base for the highest priority sample, based on the age of the sample or other criteria, for which results have been determined to be acceptable by a technologist at a remote location, r- robotically removing from the storage unit, the sample determined in step (o) to be the highest priority sample and discarding the oldest sample.

BRIEF DESCRIPTION OF THE DRAWINGS

The objects and features of the invention will become more apparent from the following drawings when read in conjunction with the specification.

DESCRIPTION OF THE PREFERRED EMBODIMENTS

Component Definition

Satellite Central (SATCEN)

Figure 1:
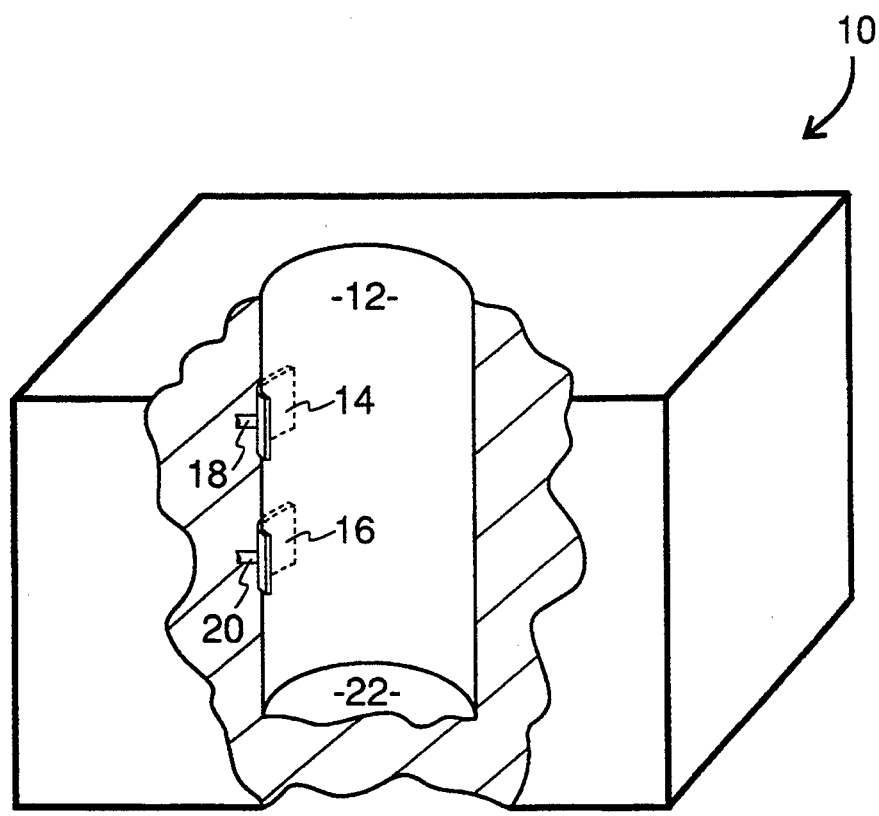
FIG. 1 is a perspective view, partly in section of the syringe receiving member of the receiving station.

This device consists of a DOS based PC computer equipped with a video monitor with a touch sensitive screen to input choices made by the medical technician. The software program has been written to interpret the digital electronic information arriving from the satellite laboratory to allow the medical technologist to view results and carry out the appropriate action. Patient results are sent from the Satellite Laboratory to the network file server where they are stored in a results database. SATCEN checks the results database for new results and displays them on the video monitor for appropriate medical technologist action.

Server

Demographic information and results interface—A dedicated micro-computer (network file server) is utilized for acquisition of patient demographic information from the hospital information system and for return of completed laboratory test results to the laboratory information system. The demographic information is acquired in real-time and stored in the local area network (LAN) server demographic database. The file server is the central storage device for all results sent from Satellite Laboratories. The file server contains a sample storage database file for each Satellite Laboratory that tracks where patient samples are in the Satellite Laboratory. The storage database file is updated when a sample is returned to the sample storage device after analysis, when new samples are put into the storage/mixing device and when the medical technologist has decided on an action to take after review of patient results.

Local area network (LAN)

Computer to computer communication is achieved through standard commercial networking hardware and software. The ANSI/IEEE 802.3 (CSMA/CD) standard is utilized as the LAN communication protocol with Novell version 3.1 networking software and EtherNet LAN interface cards for the computers on the network. Optical fibers, twisted pair, or coax cable are used to couple the network computers together.

SATELLITE LABORATORY

User interaction station

This device consists of a DOS based PC micro computer equipped with a video monitor with a touch sensitive screen. Software has been written to display choices of patient demographics, analytical tests to be performed, and modifications to the outputted data (e.g. patient temperature and hemoglobin which influence the calculation of the results of the analysis) which may be selected by the user of the laboratory.

MAGIK interfaces

MAGIK is an electronic interface that contains a microprocessor equipped with software (stored on an EPROM) which interprets the output information from the various sensors that are located on devices on the robot table (e.g. decapping device, specimen holding device, target device, storage device, personality cards).

Specimen storage device

The specimen storage device allows the temporary storage of the medical specimen. The device can be incorporated in a temperature controlled refrigeration unit and combined with a rotational specimen storage device which will mix the patient sample according to proper medical storage to stabilize the sample until analysis. The refrigerated device can keep a sample, such as a blood gas, stabilized for up to two (2) hours.

Sensors

Various sensors are used throughout the Satellite Laboratory to determine the progress of a patient sample through the Satellite Laboratory. The sensors check whether doors have opened and closed, caps have been removed and replaced on patient samples, and positions of samples in the sample storage device. Sensors which can be used in the instant invention include air pressure sensors, Hall effect sensors and optical sensors.

PC Computers

All DOS based computers used in the Remote Laboratory under Central Control are IBM computers or IBM compatible computers.

Three computers are employed in the operation of the satellite laboratory operation. The robot PC, into which all the information from the remaining two computers is fed, the environment computer (using MAGIK software) controls the periphery items. The air aspirator computer which handles the aspirator is an independent device.

The specific type of analyzer employed is not critical, since the prime aspect of the invention is the accepting, through remote operation, of a sample by a robot, the handling and processing of the sample by the robot, as required, delivering the sample to an analytical device and ultimately disposing of the sample.

The program, as written, can record the information for a number of different tests, depending upon the commercial analyzer used in conjunction with the program. Quality Control samples can be isolated within the mixer for testing and future reference.

Another feature of the computer program is self analysis by checking the various calibrations within the machinery to insure that all points are at zero, or any desired baseline. This allows the technician SATCEN to remotely check and, if necessary, reset the calibrations on the machinery at the satellite location.

Robot

Any mechanical device which can move the specimen from the specimen holding device to the uncapping device, to the air aspirator, and to the injection port of the clinical analyzer can be used as the robot. The CRS M15A or CyberFluor robots are two examples of the type which can be incorporated. Both are articulating robots and consist of the robot itself and the robot controller.

The robot is controlled by its own computer which is in communication with the various computers which form the environment and additionally, is in communication with the satellite central station's computer through the storage database on the network file server. A robot laboratory computer obtains patient demographics from a network file server in response to a request from a operator at the robot laboratory. Additionally, data from robot control files (the sample storage database files) in the network file server can be accessed at the robot laboratory. The results of tests run on a sample are transmitted to the results database file on the network file server. The satellite central computer receives the sample results for review by the satellite central station medical technologist. When the test results are accepted and the information is ready to be added to the patient's data file, the satellite central station computer interfaces with the laboratory information system computer which inter faces with the hospital information system file MIS. The cycle is repeated when patient data in the MIS file is accessed by the network server at the command of the operator in the robot laboratory who is requesting the patient data.

Personality cards

Interface cards have been produced which will translate the output of a clinical analyzer into electronic information which is standardized and compatible with the input to the software driving the Remote Laboratory under Central Control.

Analytical instrument

Any commercially available analytical instrument, such as the Corning 288 or the Nova Stat 5, can be placed in the Remote Laboratory under Central Control because of the unique design of the interfaces, hardware, and software. While reference herein is made to devices for testing the gaseous components of blood, the system also applies to devices for testing the white and red blood cells or non-hospital related analytical devices. It should be understood that while this represents a preferred system, additional components can also be used or fewer components can be employed. For example, the system can provide the desired result without the use of the refrigerated mixing storage station, although in a limited fashion.

Many clinical laboratory instruments are not designed for robotic compatibility, hence the need for standardization of data communications and analyzer interface hardware. We developed an interface with supporting software that simplifies communication between a microcomputer and clinical instruments. Our interface establishes a standardized bi-directional communications protocol, which is useful in many clinical laboratory robotic projects. Instruments targeted for interfacing require no prior on-board communications capabilities. Additionally, modifications to the clinical instrument are minimized. Once installed, the interface translates input commands to codes or actions recognizable by the analyzer. Features not normally available to the user, such as electrode real-time response and full instrument status, are also reported by the interface, thereby establishing a remote monitor and control mechanism for the interfaced instrument. The instant invention utilizes an operating system to control the interface microcomputer, which in turn commands and monitors the clinical analyzer. A host computer controls the information flow to the interface and provides (a) requests to the interface for instrument operation and status and (b) commands to the interface to initiate the desired instrument operation. This arrangement maintains complete instrument functionality as designed by the manufacturer while allowing remote monitoring and operation of the instrument.

Many instruments used in the clinical Laboratory are designed to be autonomous, easy-to-operate devices. Provisions are made for sample introduction, user data input through a keypad or other peripheral device, and reporting instrument status and test data. Instrument operation is controlled by the user or by an internal computer that coordinates instrument operation. Each manufacturer of laboratory instrumentation follows its own protocol for device control commands and instrument communications. Often data from the analyzer are limited solely to final calibration set point reports and results for patients' samples. Most instruments will report derived data to an external device, such as a printer or host computer, according to established communications protocols (RS-232C, Electronic Industry Association Recommended Standard 232, version C).

Each analyzer used within the robotic laboratory must have the ability to be controlled by and communicate to the laboratory host computer in a standard format. Operational control and monitoring of an analyzer must not only include access to the data produced by the instrument but also allow for total peripheral control of the analyzer. Most instruments today are not designed to be operated remotely by a host computer; however, implementation of the instant interfacing techniques allows for remote operation. This approach to instrument control and monitoring simplifies the inclusion of new instrumentation within a novel unmanned clinical robotics laboratory.

The environment in which the interface is to be implemented dictates the priority of design features, e.g., (a) minimal modification of the target instrument, (b) access to bus structure or equivalent information paths, (c) independence of manufacturer communications protocol, and (d) complete remote monitoring and control of the target instrument, including real-time status of clinical instrument operation.

Maximizing interface flexibility led to a two-board design (microcomputer and personality card) in conjunction with a custom cable to connect the instrument with the interface. To simplify the connection of the interface to the instrument, we limited hardware changes to the personality card, which allowed the microcomputer hardware to remain standard for each application. Interrupt jumpers and an instrument-specific software package were the only microcomputer board changes required for each new instrument. Communications between the interface and the workcell host computer were made via RS232C hardware and software protocols.

The interface is designed around two boards (microcomputer and personality card). Standard electronic hardware is used in the design of the interface, which is based on Intel Corp. (Santa Clara, Calif.) integrated circuits (3). The microprocessor (no. 8085), a peripheral interface adapter (PIA, no. 8155), universal synchronous/asynchronous receiver/transmitter (USART, no. 8251), 4-kilobyte (kbyte) erasable programmable read-only memory (EPROM, no. 2732), 8-kbyte static random-access memory (RAM, no. 6164), and support circuitry composed the interface microcomputer.

The personality card is designed and fabricated in-house by using an 8kbyte RAM (no. 6164), a 4-kbyte EPROM, and support circuitry. The two boards are connected via a 40-pin address/data/control cable. A custom cable from the personality card connected the target instrument buses to the interface. The personality card hardware alterations were limited to jumper-selectable address/data/control bus configurations. The EPROM on board the personality card set valid addresses, through which the interface was to gain target instrument information.

Software used to write the assembly code necessary for interface operation included the Turbo C 2.0 editor (Borland International Inc., Scotts Valley, Calif.), a software package necessary for cross-assembly of the source code to Intel no. 8085 assembly language (Version 4.01, 2500 A.D.; Software Inc., Aurora, Colo.), and an EPROM programmer (EPROM-I) and driver software (International Microsystems Inc., Milpitas, Calif.). The clinical instruments we used to implement the interface were the Corning 178 and 288 blood gas analyzers (Ciba-Corning Boston, Mass.) and the DuPont NaK and NaKLi electrolyte analyzers (DuPont Co., Wilmington, Del.).

The design of the interface concentrates on availability of data on the instrument computer system buses. Bus level control reduced the dependence on individual manufacturer's design techniques and gave the interface access to the same information as the instrument microprocessor. Since not all laboratory instruments have bus level operations, the design considerations are selected to accommodate these systems. The interface microcomputer (MAGIK: Medical Analyzer Generic Interface Kard) incorporated peripheral interface adapters that access input/output lines for controlling non-bus-structured instruments. Using the personality card and a specific software package, a non-bus-structured instrument is controlled. Interface operation is similar in function to any peripheral instrumentation that the existing instrument may have attached, except that MAGIK also possesses the ability to control the instrument with the aid of information from a host computer.

Analyzers have subassemblies for storing or displaying information on operation and function. The personality card mirrors the necessary subassemblies and can also mimic the instrument input command sequences used to operate the analyzer. Both target instrument and microcomputer interact with the personality card, which gives MAGIK the desired control over the target instrument. Personality card access is prioritized to allow the analyzer to maintain default control. When MAGIK requires data and (or) operational status, it takes control of the personality card and performs the specific task requested. This mirroring of the target instrument gives MAGIK the ability to return to instrument realtime status and, in some cases, provides data not normally available from the manufacturer's original design (e.g., electrode response during calibrations, sampling sequences).

The operating system (KAOS: Klinical Analyzer Operating System) is designed to simplify target instrument program requirements. KAOS routines control the interface mirocomputer and personality card that were called by the specific instrument software packages. Because there are set procedures that the interface performs to control an instrument, a large portion of any software package is included in KAOS, a feature that reduces the time required to develop each new application. The interface software supports communications port handshaking (control of data transmission or reception), transmission error checks (confirming the integrity of data sent), and interruptable operation (the interface servicing a time-dependent operation) along with the necessary operations for instrument control.

A unique set of software commands is used for each clinical instrument to allow the instrument to be controlled by the inter-face. The instrument-specific software translates instrument data into a standardized string for transmission to a host computer.

The standardized output string for each instrument is made up of an instrument identifier, a mode of operation, the instrument command, device real-time status, results, error checking, and a transmission terminator. The instrument identifier field holds a lead character and a two-digit number (e.g., Corning: COI). The mode of operation was a single ASCII (American Standard for Communications Information Interchange) character. A-Automatic, C-Command, D-Diagnostic, E-Error, R-Results. The default mode is Command. If the interface detects an instrument operational error, the Error mode is indicated. The Diagnostic mode can be set by the host computer to enable routines on board the interface to assist in instrument evaluation and troubleshooting. The Automatic mode, also externally selectable, was used to assist in the quality-control operation of the instrument. The interface is capable of automatically testing calibration results and operations and, if an error is detected, a selected number of attempts to correct the malfunction are initiated. The interface computer attempts to "repair" the instrument by initiating wash or purge sequences, for example, according to the manufacturer's recommendations. If the device error cannot be corrected, an error status is set and the host computer is informed.

The command-field is a character selected from a standard command set developed for this interface. Use of a standard command set for all target analyzers simplifies the MAGIK/KAOS instrument control routines. The command set is divided into subsets that perform calibrations, retrieve data, set operation parameters, ascertain device status, and control manual instrument function. One set of commands for any instrument or group of instruments reduces the demands on the host computer for specific device evaluation. Instrument real-time status was packaged as an 11-character ASCII set and decoded to indicate full instrument operational status. Most target instrument functions can be indicated within this field.

Instrument results are packaged within delimiting brackets to allow ease of extracting results. Any sequence of instrument results could be mimicked by other similar devices used with the interface. For example, if two different blood gas analyzers are controlled by MAGIK, both will report results in the same sequence, irrespective of the original manufacturer's design (pH, pCO2, pO2, etc). This sequencing allows the host computer to be unaffected by changes resulting from manufacturer design or user instrument selection, which simplifies instrument control and processing of results.

A routine for checking transmission errors can be selected that will send a pair of characters in the command and the results strings, to ensure accurate data transmission. A transmission termination character is sent to inform the host computer of the end of the string. In reverse, MAGIK/KAOS also translates standardized commands from the host computer into operational requests that the target instrument recognizes.

Corning 178 blood gas analyzer. Modifications of the analyzer were limited to removal of a switch logic board (board no. 7) and replacement of it with a connector card and custom cable. Commands that the blood gas analyzer used to initiate operation were loaded to a particular personality card memory location and an interrupt was triggered. Data as well as instrument operation were indicated from the memory output and, with proper decoding, a real-time status was returned. Use of the real-time scan gave the host computer (or operator) full monitoring of the blood gas analyzer and, in conjunction with the input commands, complete control and remote monitoring of the analyzer. An added benefit offered by the real-time scan was monitoring of electrode response of the analyzer at any time. With this scan, we could troubleshoot instrument errors from a remote site.

DuPont Na/K benchtop analyzer (Na/K/Li, Model 985). Full operational control and monitoring were possible by using MAGIK/KAOS and a software package designed for the analyzer. Results from the analyzer were sent to a single memory location on the personality card interrupting MAGIK/KAOS, which in turn saved the character, mirroring the analyzer display. The Na/K analyzer is a menu driven system with yes and no key controls for operation. These keys were disabled and, using two peripheral interface adapter control lines, the switch units were replaced..

Corning 288 blood gas and electrolyte analyzer. Similar in approach to the DuPont system, the Model 288's display information is captured by MAGIK/KAOS through the use of interrupts to the interface. Manipulation of the display information allows remote monitoring of instrument function by the host or operator. Keypad function is mimicked by use of the peripheral interface lines, which give full operational control of the instrument.

There are three basic areas in which instrument standardization is necessary: sample preparation and introduction, operator input of information to the analyzer, and output of information from the analyzer to the user. Instrument input and output standardization has been addressed by the MAGIK/KAOS interface. For example, the standardized output string is made up on an instrument identifier, a mode of operation, the instrument command, device real-time status, results, error checking, and a transmission terminator-a protocol designed with enough inherent flexibility to be used with virtually any instrument currently on the market. Our input strings are simply the reverse of the output string except that a field for instrument control is substituted for device real-time status. A single set of interface input commands is used to control any analyzer used with the interface.

In summary, the implementation of the MAGIK/KAOS interface allows the standardization of target instrument communications as well as complete device monitoring and initial phases of troubleshooting, all from a remote site. The application for which the interface was designed-the automation of a critical-care robotic laboratory-has been simplified: the host computer communicates by using a defined set of commands and receives a standardized string for any analyzer encountered. The design allows any instrument to be implemented and is independent of the manufacturer's design and communications protocol. Applying the MAGIK/KAOS interfacing techniques will facilitate a more-uniform information transfer within any setting, independent of the target instrument design.

Process sequence Example I

Figure 24:
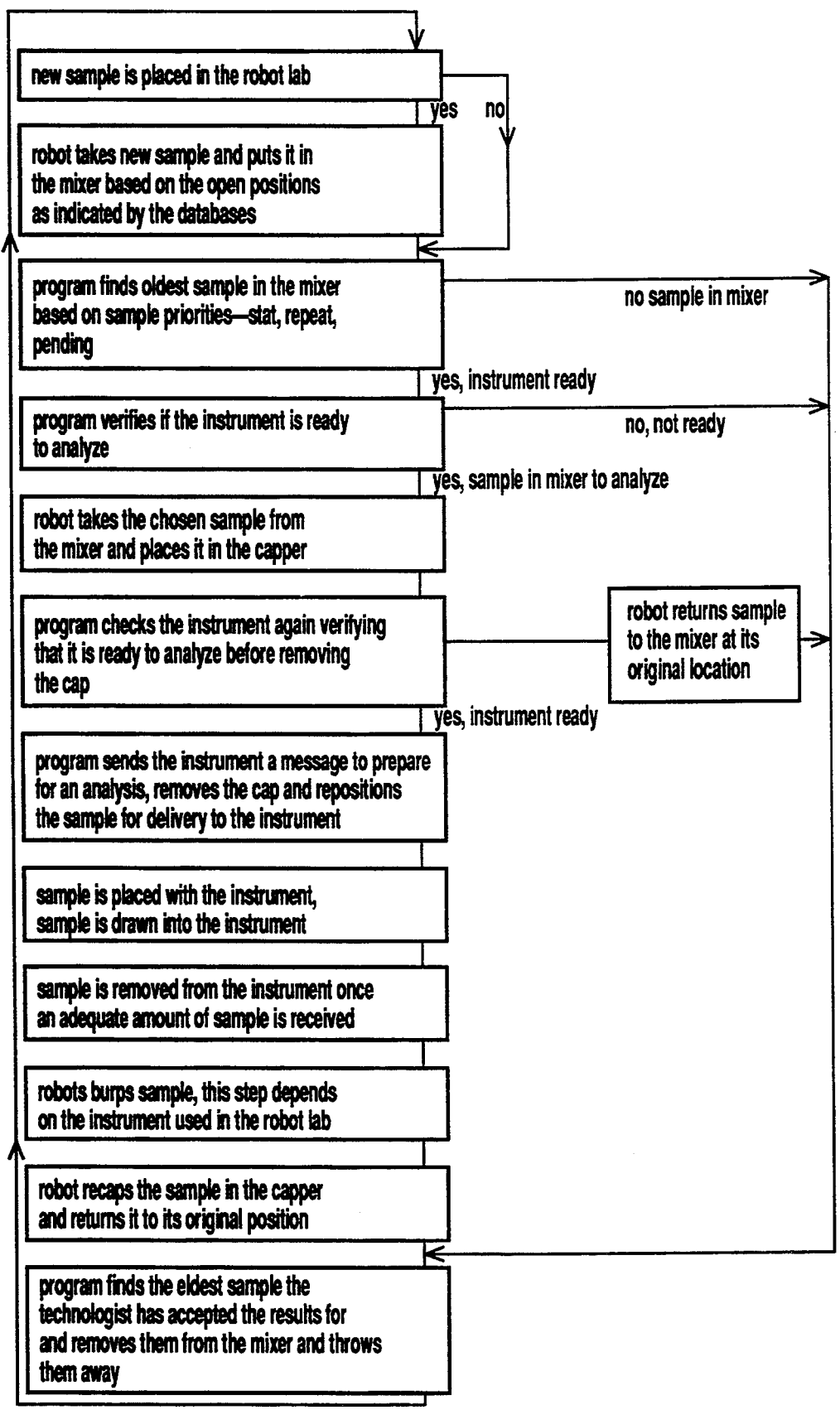
FIG. 24 is a flow chart of sample handling logic.

The logic sample of Example I is illustrated in FIG. 24.

1 A new sample is placed on a sample receiver station,
2 The robot gets the sample and places the sample in the storage unit based on the storage database's information on the next available open position,
3 The program finds the oldest sample in the storage unit, based on the sample priorities,
4 The program checks the instrument to see if its is ready to analyze a sample,
5 The robot gets the chosen sample from the storage unit and places it the decapper,
6 The program checks the instrument again to see if it is ready to analyze before removing the cap from the sample containing device,
6 The program sends the instrument a message to prepare for an analysis, removes the cap and repositions the sample for delivery to the instrument,
7 The sample is docked with the instrument and a portion of the sample is drawn into the instrument,
8 The sample is removed from the instrument when the instrument tells the program it has enough sample,
9 The robot delivers the sample to an air aspirator and removes air from the sample,
10 the robot delivers the sample to the decapper and the decapper replaces the cap on the sample containing device,
11 The robot returns the sample to the position within the storage unit from which it was originally removed,
12 The program finds the oldest sample for which the technologist has accepted the results, removes the sample from the storage unit and discards the sample.

Process Sequence Example II

The programs that run on the DOS based PC's (SatCen, User Interaction Station (UIS), and Samhand, which controls the handling of the samples) are all written in the computer language called "C". The compiler is called Turbo C, version 2.0 which takes the "C" source code and complies it into a executable program. Paradox 3 is a commercial database program; Paradox Engines, version 1.0 is a set of functions called libraries that are used with the "C" source code. These functions allow the programmer to access the Paradox 3 database files. No programs were written in Paradox 3. They were written in "C" using the Paradox Engine functions to access the Paradox 3 databases.

SatCen, Satellite Central, Samhand—Sample handling, robot computer are names used for the following programs.

1. Samhand asks MAGIK to check to see if a new sample is in the holding block, MAGIK returns to Samhand that it "sees" a new sample.
2. Samhand tells the robot arm to get the new sample.
3. Samhand finds an open position in the mixer by looking at the storage database file on the server.
4. Samhand translates the open position into commands that MAGIK and the robot arm can understand.
5. Samhand tell MAGIK through the command in step 4 to find the face on the sample mixer where it will be put.
6. MAGIK finds the face, stops the mixer, locks the mixer and opens the door. When all this is done, MAGIK sends to Samhand it is done—the door and face are ready,
7. Samhand sends the command (from step 4) to the robot arm to put the sample in the open position in the mixer. The robot arm sends to Samhand when it is done.
8. Samhand sends a command to close the mixer door and start the mixer. Throwing away an accepted sample is similar to getting a new sample.

To analyze a sample:

1. Samhand checks to see if there is a sample in the storage database on the server that needs to be analyzed. Samhand finds the position of the sample on the mixer through the storage database.
2. Samhand translates the sample into commands, as in step (4) above.
3. As in step (5) above, Samhand tells MAGIK to find the right face to get the sample from.
4. As in step (6) above.
5. As in step (7), but get the sample, then step (8) above.
6. Samhand sends command to robot arm to put sample into decapper.
6a. Samhand checks to see if the instrument is ready to analyze the sample, yes it is ready. Samhand sends command to instrument to prepare for sample analysis.
7. Samhand sends command to MAGIK to close the capper gripper.
8. Samhand asks MAGIK if the capper did close.
9. MAGIK sends to SAMhand, yes the capper is closed.
10. Samhand sends command to robot arm to move sample out of the decapper.
11. Samhand asks MAGIK if the cap has been left in the capper.
12. MAGIK sends to Samhand, yes there is a cap in the capper.
13. Samhand sends command to robot arm to reposition the sample.
14. Samhand sends command to robot arm to dock with instrument.
15. Samhand sends command to instrument to analyze sample.
16. Samhand checks instrument to say it has enough sample.
17. Samhand sends command to robot arm to undock with instrument.
18. Samhand sends command to robot arm put sample in decapper.
19. Samhand sends command to MAGIK to open the decapper.
20. Samhand asks MAGIK if the capper is open.
21. MAGIK sends to Samhand, yes capper open.
22. Samhand sends command to robot am to seat cap on sample and remove sample from decapper.
23. Samhand asks MAGIK if there is a cap in the capper.
24. MAGIK sends to Samhand, no-there is no cap.
25. As in step (3), step (4), step (5), but put the sample in mixer.
26. Samhand sends command to MAGIK to close the mixer door and start the mixer.

MAGIK Interface

The MAGIK interface has a microprocessor with a software program that has been permanently written to the microprocessor (the EPROM). The computer language is called assembly. Information sent to and from the MAGIK microprocessor uses the RS232C protocol. The information is sent one bit at a time. MAGIK controls the environment the robot works in, i.e. the sample holding device, the decapping device, and the mixer. MAGIK can sense what state a device is in and sends commands to a device. The commands MAGIK sends to a device depends on the command Samhand has sent to MAGIK. MAGIK is a smart device in to itself, but it is a slave to the Samhand program and does nothing until Samhand sends it a command. The DOS based programs (SatCen, UIS, Samhand) are going through logic decisions all the time, but MAGIK waits until Samhand has told it to do something.

| Analytical Test Result Example I |
|---|
| PATIENT NAME: TEST EXAMPLE 1 |
| HISTORY NUMBER: 0304867 |
| MIS NUMBER: 940584 |
| ANALYSIS TIME: 11:36:34 |
| LOCATION: 9999 |
| pH: 7.299 |
| pCO2: 1.2 mmHg |
| pO2: 191.7 mmHg |
| hct: 33.% |
| Na: 146. mmol/L |
| K: 0.3 mmol/L |
| Cl: 41. mmol/L |
| Ca++: 0.29 mg/dl |
| Glucose: 13. mg/dl |
| Analytical Test Result Example II |
| PATIENT NAME: TEST EXAMPLE 2 |
| HISTORY NUMBER: 0000123 |
| MIS NUMBER: 930191 |
| ANALYSIS TIME: 14:26:54 |
| LOCATION: NOVA |
| pH: 7.408 |
| pCO2: 4.2 mmHg |
| pO2: 171.7 mmHg |
| hct: 3.% |
| Na: 138. mmol/L |
| K: 4.3 mmol/L |
| Cl: 98. mmol/L |
| Ca++: 4.29 mg/dl |
| Glucose: 3. mg/dl |

DETAILED SEQUENCE OF OPERATION

A satellite central station, SATCEN employs a DOS based PC type computer for receiving and processing inputs from a plurality of robot laboratories. The robot laboratories can be located in a variety of locations within the same hospital which houses satellite central station or they can be located at various doctors offices, clinics or hospitals. The satellite laboratory can, advantageously, employ a separate computer for each robot operated component of the laboratory, such as an analyzer, a refrigerated specimen storage device/storage unit, and an air remover or air aspirator.

When members of the medical staff of the hospital enter the room containing the robot they are greeted by the User Interaction Station, a touch sensitive computer screen, similar in use to a bank teller machine. Access to the system is controlled by user specific passwords, although other technologies such as magnetic card stripe, barcode, key, or fingerprint recognition devices could be used. The patient and his/her hospital identification number are selected from a menu of patients displayed by the User Interaction Station for the nursing location selected or by the patient's hospital history number. Following patient selection, the analyses desired together with any modifying information are entered by simple touchscreen selections. After the patient demographics and chemistry profiles are selected and reviewed, the patient specimen in a freshly-drawn unlabeled syringe is placed in a holding rack. The rack can be either an indexing rack with multiple receptacles for the specimen or a single receptacle. Furthermore, the rack may be cooled and rotated to preserve the integrity of the specimen. The robot retrieves the specimen from the specimen holding rack, uncaps it in an uncapping device and then introduces it into the analyzers. After the analysis is complete the specimen is recapped in the capping device by the robot and placed in a temporary storage device.

Results are sent to the main hospital laboratory through a local area network (LAN) coupled to the robot laboratory via a wire, optical fiber, or radio signal. In the main laboratory a trained medical technologist reviews the results of the analysis by observing the computer running the SATCEN program, which has been equipped with a touch screen. Options available to the technologist are to either accept the results if they are within the reference range or repeat the analysis if critical values (values which may indicate a life threatening condition) are obtained. If the results are within the limits of normal healthy individuals then the technologist prompts the robot to discard the remainder of the specimen into a hazardous waste container. When critical results are obtained, the robot is asked to repeat the analysis. If the results of the first and second analytical run agree then the critical result is telephoned to the patient's physician. Samples can be repeated multiple times until all of the sample has been used for analysis. Discrepant results require a trained person to visit the laboratory and resolve the error.

The system as disclosed herein is designed to operate with standard syringes, such as Beckton & Dickenson, 3cc syringe, reorder #5586 and Beckton & Dickenson, Luer Tip Caps, reorder #8341. Both are produced by the Beckton & Dickenson Co, Rutherford, N.J. The system can be designed for any type or size syringe and cap; however for consistency, all references made herein are to the foregoing sizing.

Figure 2:
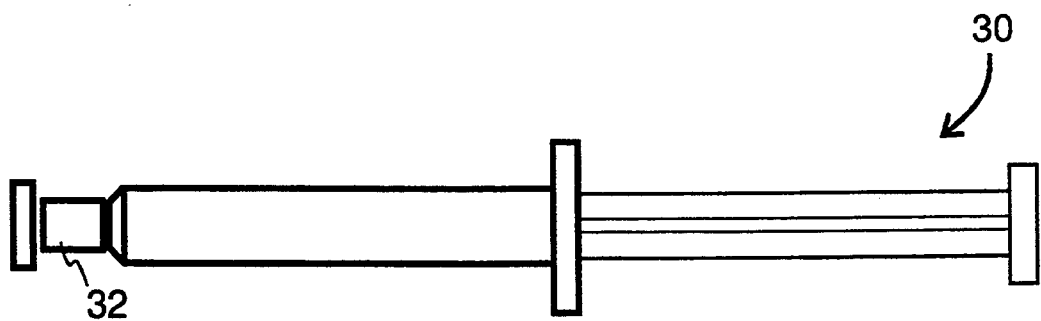
FIG. 2 is a side view, partly in section, of a prior art syringe and cap of the type used in the instant disclosure.

The receiving station 10, as illustrated in FIG. 1, is used for initial receipt of the syringe 30, thereby initiating the mechanical process. The syringe 30 of FIG. 2 is placed in the receiving area 12 of the receiving station 10 by the technician so that the cap 32 firmly rests on the base 22. The sensors 14 and 16 register the presence of the syringe 30 and signal, through wires 18 and 20, the environment computer that a syringe 30 is in place. The double sensors 14 and 16 are is employed to insure that prior to activation, an actual syringe has been inserted rather than just a cap or other small object. The robot PC has been instructed to initiate the testing program and the insertion of the syringe 30 into the receiving area 12 commences the robot arm activation.

Figure 21:
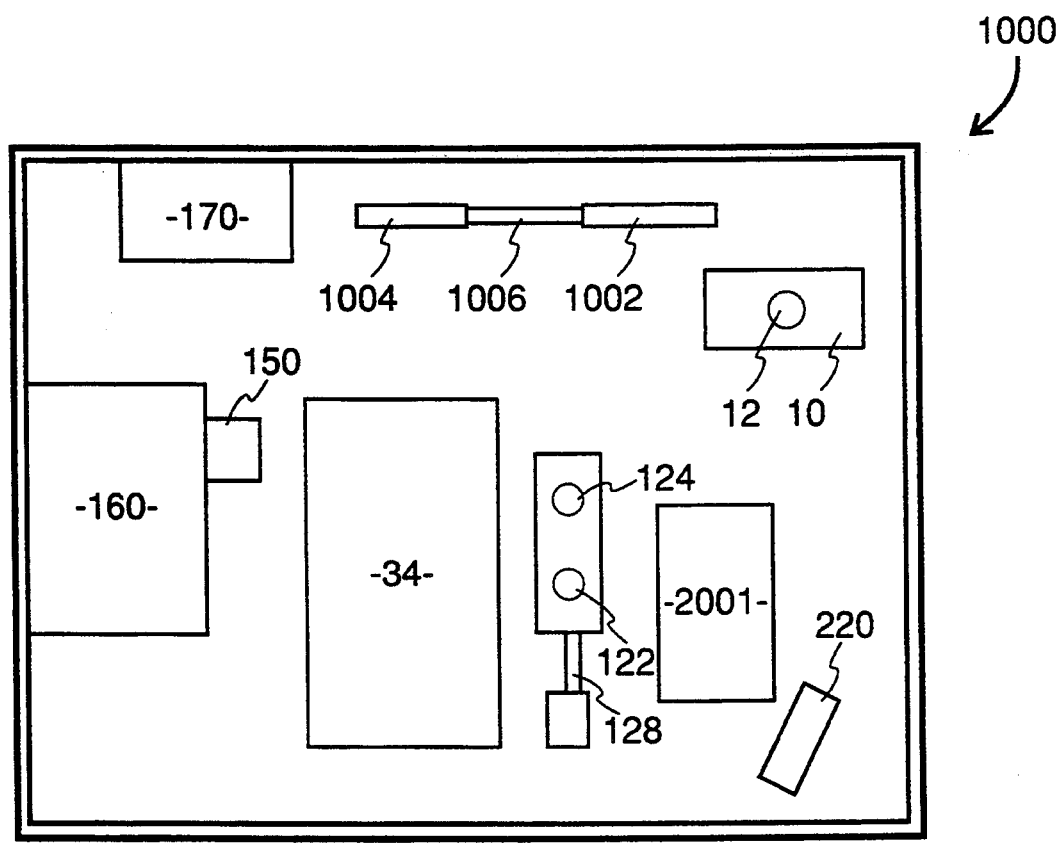
FIG. 21 is a plan view of the robot station.

The environment program checks and double checks that the syringe 30 is in place and signals the robot PC program to bring the robot 2001, of FIG. 21 to place itself at the preprogrammed position for grasping the syringe 30 at the receiving station 10. The robot 2001 grasps the syringe 30 with its fingers 190 (FIG. 18), lifting it from the receiving area 12.

Figure 3:
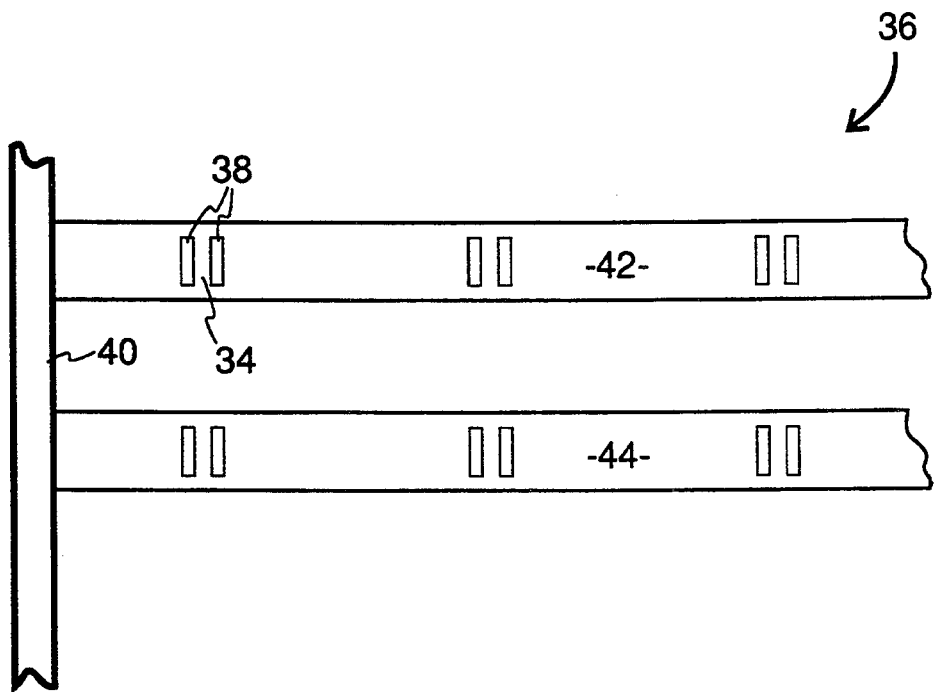
FIG. 3 is a fragmentation plan view of the storage member of the instant disclosure.
Figure 4:
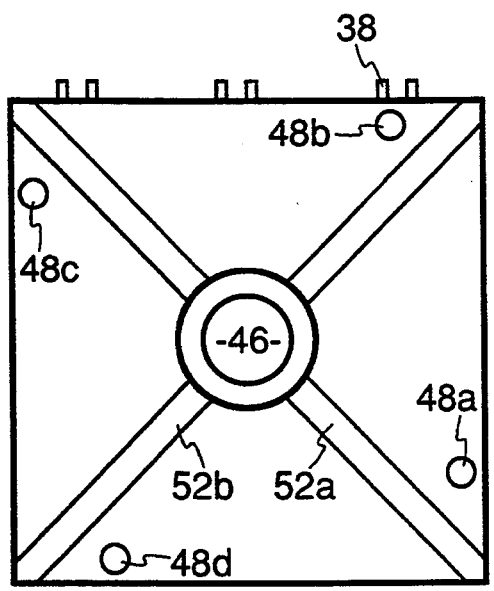
FIG. 4 is a side view of the storage member of FIG. 3.

Once the environment computer has indicated that the robot 2001 is to commence the process of retrieving the syringe 30, the environment computer then locates the next available specimen storage space 34 in the specimen storage device rack 36 as shown in FIGS 3 and 4. The specimen storage device rack 36, as disclosed herein, is divided into four faces, each face having a placement on the face disc 50. The environment computer is continually aware of the empty specimen storage device clips 38 on the faces and once the specimen storage device clip 38 to be use is determined the computer stops the specimen storage device rack 36 at the appropriate face. The selection of a four sided specimen storage device rack 36 for the instant disclosure does not, in any way, limit the scope of the sizing of the specimen storage device. The storage capacity of a specimen storage device would be determined by the estimated number of specimens to be processed in a given period of time, as well as cost. The number of faces and number of clips per face can be selected as desired. Four, six and eight faces are preferred configurations, whereas the length of the faces, that is, the number of clips per face, is determined the space limitations and cost restrictions.

Figure 5:
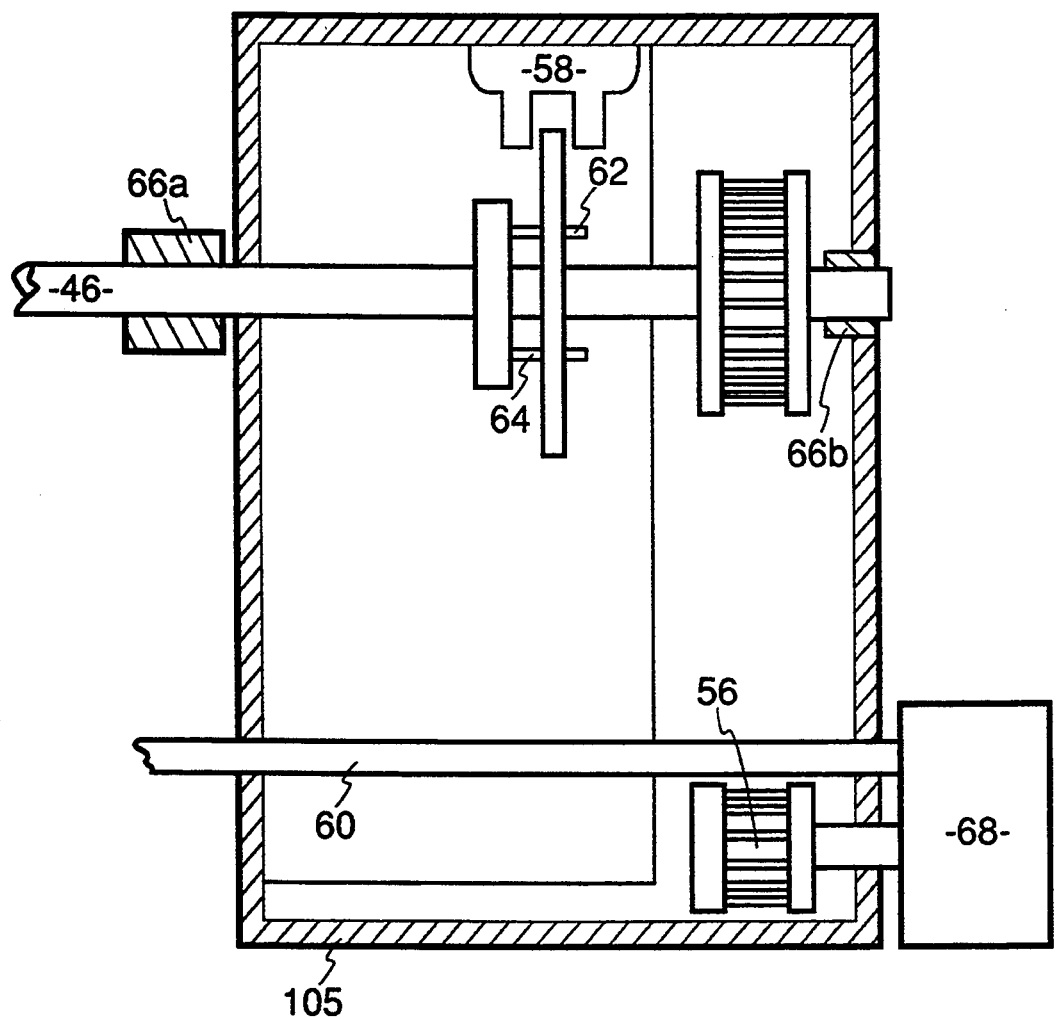
FIG. 5 is a side view, partly in section, of a portion of the storage member drive and positioning member of the instant disclosure.
Figure 8:
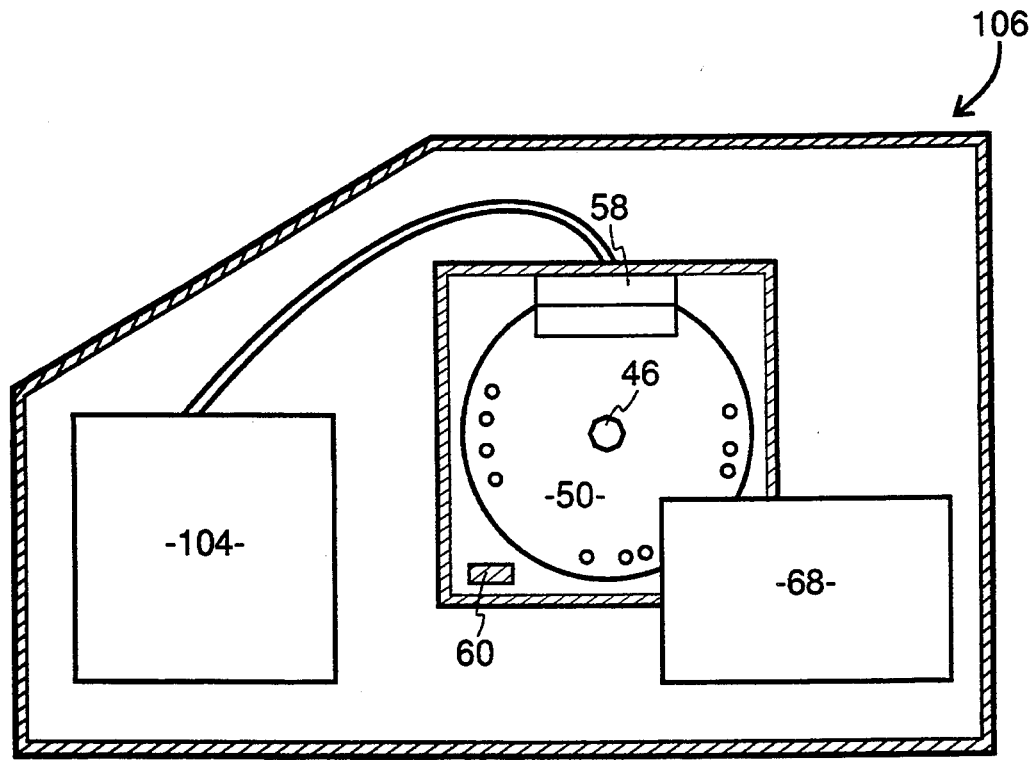
FIG. 8 is a side view of the storage member assembly of the instant disclosure.
Figure 9:
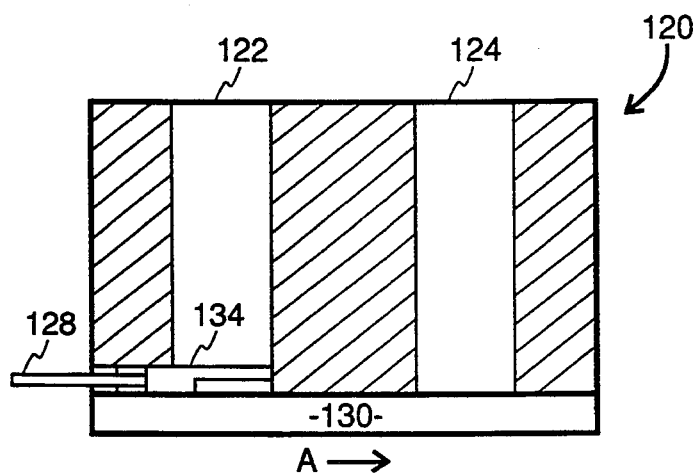
FIG. 9 is a fragmentary side view, partly in section of the syringe positioning and decapping member of the instant disclosure.
Figure 12:
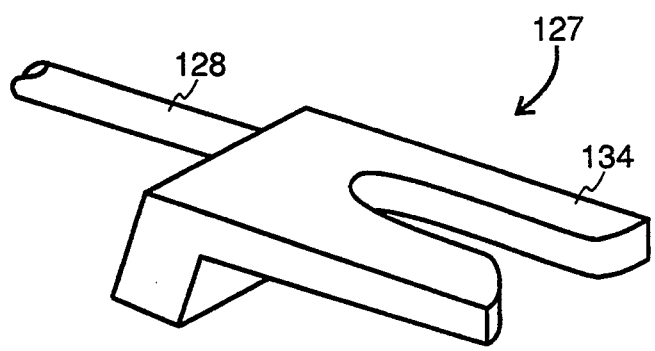
FIG. 12 is an alternate embodiment of the device of FIG. 9.
Figure 10:
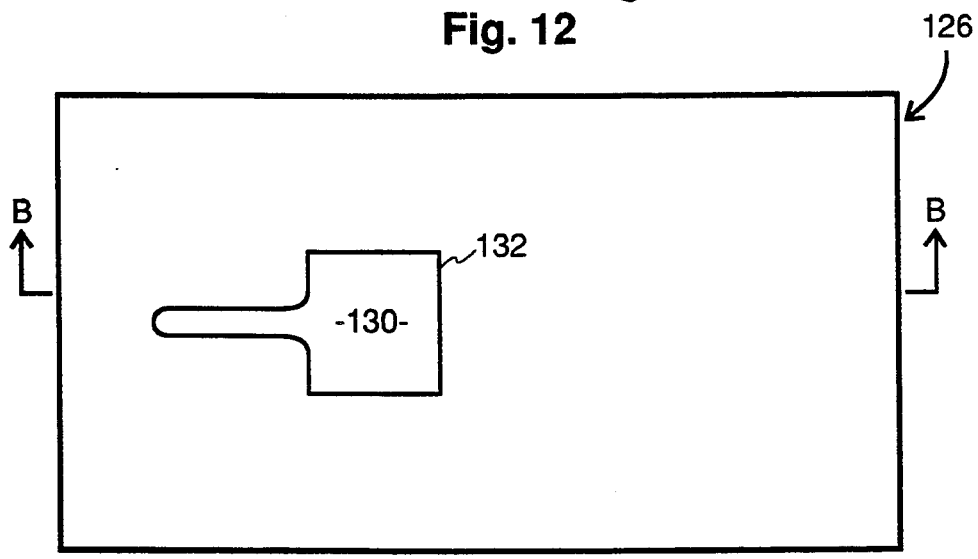
FIG. 10 is a fragmentary perspective view of the syringe cap engaging member of the instant disclosure.
Figure 20:
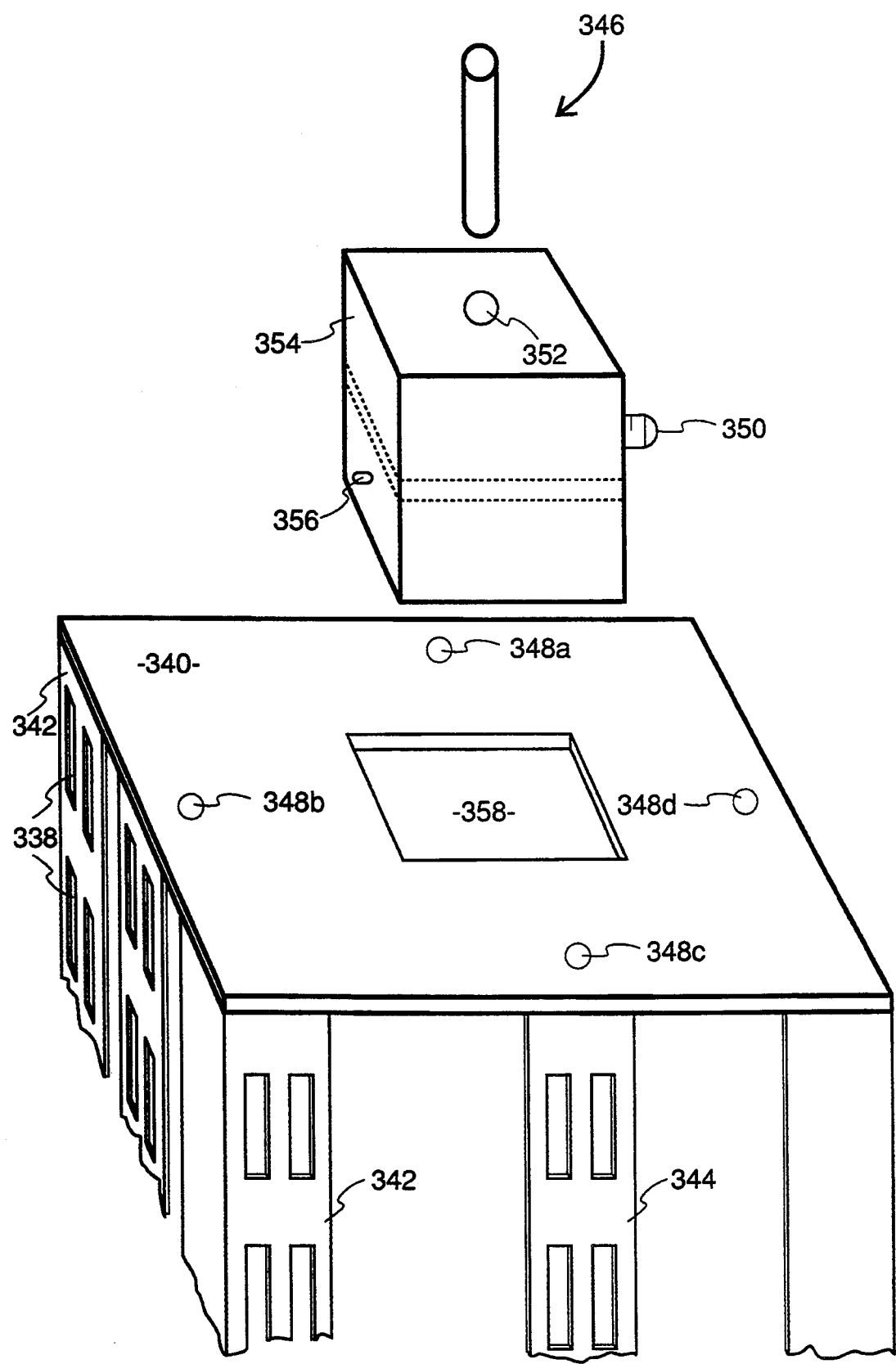
FIG. 20 is an exploded, perspective end view of an alternate embodiment to FIG. 3.

The specimen storage device 334 as shown in FIG. 20 is run by the specimen storage device control panel 106 as illustrated in FIGS. 5 and 8. A cutaway side view of the specimen storage device 334, FIG. 5, provides a clear idea of the placement of the controls. The motor 68 is located on the outside of the panel and is hooked directly into motor gear 56. The motor gear 56 and rotating shaft gear 54 are connected via a belt (not shown) and are standard motor technology well known in the art. The rotating shaft gear 54 drives the rotating shaft 46 which runs through the specimen storage device control panel 106, through the face disc 50 to the specimen storage device rack 36. The face disc 50 is locked to the rotating shaft 46 through use of disc lock 64. The disc lock 64 can be fixed to the face disk 50 by screws 62, or other convenient means. Similarly, the disc lock 64 can be fixed to the rotating shaft 46 by a locking screw. The disc lock 64 and disc lock 62 must firmly lock the face disc 50 to the rotating shaft 46 to prevent slippage between the two members. The shaft 46 and the shaft receiving opening 70, in the face disk 50, are non-circular so as to further prevent relative motion of the shaft 46 and the face disk 50. The positioning of the specimen storage device rack 36 is directly controlled by the face disc 50 and the alignment must be exact to assure that the specimen storage device clips 38 are aligned correctly for placement of the syringe 30 by the robot 2001.

As shown in FIG. 5, the sensor bar 58 is located at the top of the specimen storage device drive housing 104, of the specimen storage device drive unit 106 and consists of four pairs light sensor units. Each unit is aligned opposite one another, with one component being a light emitter and the other being a light sensor. The face disc 50 is positioned within the sensor bar 58 so that the sensors are positioned to read the settings positions of the face disc 50, as described further herein in relation to FIG. 6.

The stop locking bar 60 is used to stop the movement of the specimen storage device 334 and to maintain the steadiness of the specimen storage device 334. It is activated immediately upon the achieving of the correct positioning of the required face of the specimen storage device. The bearings 66a and 66b are preferably sintered bronze which is standard to the industry and protect the rotating shaft 46. Other materials can be used for the bearings 66a and 66b, such as Delryn, Teflon or nylon.

The front positioning of the specimen storage device control panel 106 is illustrated in FIG. 8, with the front of the specimen storage device control panel 106 removed, exposing the face disc 50. The circuit boards 104 are standard to the industry, and therefore the components and schematics are not shown.

Figure 7:
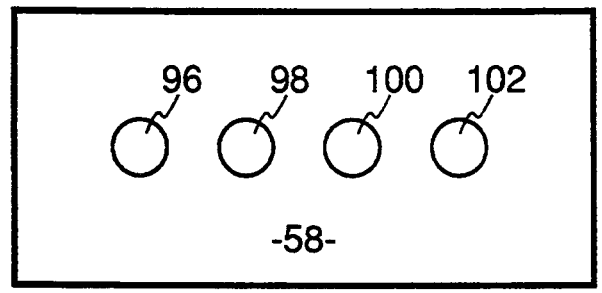
FIG. 7 is a side view of the sensor assembly for use in conjunction with the face disk of FIG. 6.
Figure 6:
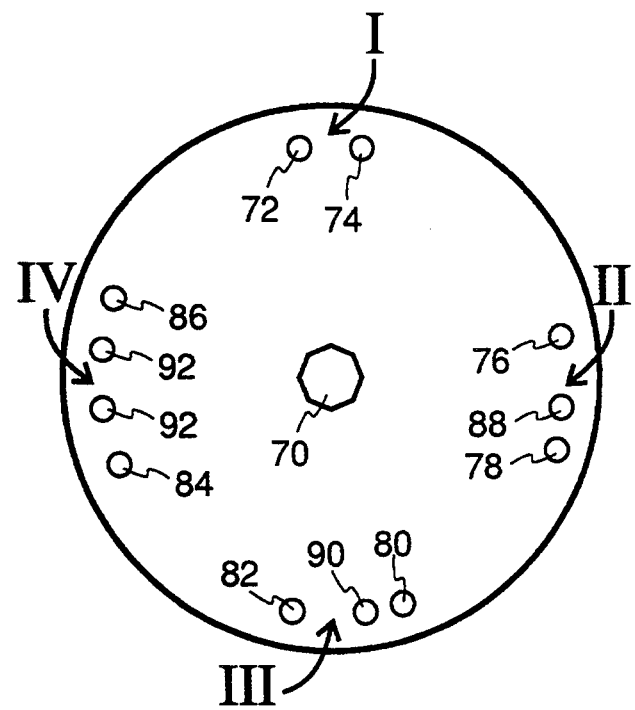
FIG. 6 is a side view of the face disk of FIG. 5.

The face disc 50 is shown in detail in FIG. 6, wherein the placement of the four indicators is illustrated. The indicators are set in sets of four and consist of locations which either have or do not have openings. The outer two indicators of each group serve as stop bits and the interior two indicators serve as position indicators. In group I, locator stop bit 72 and locator stop bit 74 are the two stop bits and the interior has no openings and are read as negatives. In group II a one positive position indicator 88 is read as a positive, leaving the other position to be read as a negative. In group III the positive position indicator 90 reverses the positive and negative readings and in group IV positive position indicator 92 and positive position indicator 94 provide dual positive readings. One half of the sensor bar 58 is shown in FIG. 7 with the stop bit sensor 96, indicator sensor 98, indicator sensor 100 and stop bit sensor 102 positioned to align with corresponding indicators. To assure alignment stop bit sensor 96 and stop bit sensor 102 position to make sensor contact with their counterpart on the opposite section of the sensor bar 58 (not shown). The sensor contact can only be obtained by one of the groups of indicator stop bits pairs, locator stop bit 72 and locator stop bit 74, locator stop bit 76 and locator stop bit 78, locator stop bit 82 and locator stop bit 80 or locator stop bit 86 and locator stop bit 84 being positioned in alignment with stop bit sensor 96 and stop bit sensor 102. When this alignment is obtained the f98a and indicator sensor 100 can read the position indicators and determine which face is exposed. The sensor bar 58 can be purchased commercially under, as for example, through Motorola as optointerrupters or Harris Semiconductors as photon-coupled interrupter modules.

As an alternative to the horizontal sequencing of the sensors stop bit sensor 96, indicator sensor 98, indicator sensor 100 and stop bit sensor 102, the sensors can be aligned in a vertical positioning with the corresponding indicators being realigned accordingly. The face disc 50 are commercially sold by Hewlett Packard and others and are frequently known as optical encoding discs. The method of optointerrupter modules in combination with encoding discs is the embodiment used in the instant disclosure, however there are several methods of transmitting location information to a computer or receiver. This information is known in the prior art, and many of such devices can be substituted, as would be known to one versed in the prior art.

As stated, the rotating shaft 46 must be firmly secured to the specimen storage device rack 36 to allow for proper alignment. The specimen storage device rack 36 of FIGS. 3 and 4 is a square metal or plastic device consisting of a top support rail 42 and a bottom support rail 44 connected to specimen storage device supports 40. The specimen storage device clips 38 are connected in aligned pairs to the top support rail 42 and bottom support rail 44 and dimensioned to receive a syringe 30. The integrity of the specimen storage device rack 36 is maintained by diagonal supports 52a and 52b and connected to the rotating shaft 46 at the center. The stops 48a, 48b, 48c and, 48d are positioned to receive the stop locking bar 60 when it is slid into position.

Once the environment computer has requested an empty specimen storage device clip 38, the robot PC chooses the oldest open position, locates the face on which the empty specimen storage device clip 38 is located, and notifies the environment computer face to locate. The environment computer stops the face disc 50 at the location which causes the correct specimen storage device rack 36 to be positioned with the specified empty specimen storage device clip 38 aligned to allow the robot to insert the syringe 30. Once the specimen storage device rack 36 is positioned, the environment computer opens the door of the specimen storage device 34, the syringe 30 is placed in the specimen storage device clips 38 and the computer signals the door to close. The specimen storage device rack 36 is then rotated a predetermined number of times in order to mix the blood sample thoroughly. Once the number of rotations is obtained the specimen storage device rack 36 is stopped and the syringe 30 removed. The door is then again closed. The specimen storage device 34 door is a standard slide unit which is known in the prior art and can be of a number of configurations. The door is connected to a standard pneumatic opening device which, when the signal is received from the computer opens or closes. The specimen storage device rack 36 is, in the described embodiment, placed in a refrigerator unit which maintains the temperature at a desired temperature.

Figure 11:
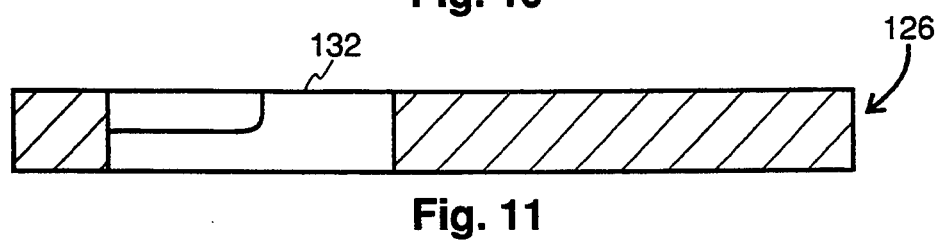
FIG. 11 is a cut away side view of the syringe cap engaging member of FIG. 10.

Once the syringe 30 has been removed from the specimen storage device 34 it is placed in the decapper 120, as shown in FIGS. 9, 10, 11 and 12, for removal of the syringe cap 32. Prior to insertion of the syringe 30 to the decapper 120, the environment computer checks to verify that the pneumatic controller 128 has placed the gripping device 134 in a position to insure that the syringe 30 is placed so that the syringe cap 32 is resting in the base area 130 of the decapper 120. Upon verification of positioning, the robot 2001 is instructed to insert the syringe 30 into the decapping area 122. Sensors within either the decapping area 132 or the gripping device 134 confirm that the syringe cap 32 is positioned to rest on the decapper base 130. At in the receiving station 10, dual sensors can be used to verify that the object being inserted is a syringe 30 and not a misplaced syringe cap 32 or other object. After verification that the syringe 30 is in place on the decapper base 130, the environment computer instructs the pneumatic controller 128 to move in the direction of arrow A to a locked position, thereby locking the syringe cap 32 under the gripping device 134 illustrated in FIGS. 9 and 12. After verification that the syringe cap 32 is locked in place, the robot 2001 removes the syringe 30 and places it in the repositioning area 124, where it releases the syringe 30. Reconfirmation is then made to insure that the cap 32 is left in the decapping area 122 and that the gripping device 126 is still in the locked position. In the preferred embodiment of FIG. 10, the molded gripping device 126 is a single piece device which has been cut through, at cut out area 132, to allow for the syringe cap 32 to set on the decapper base 130. In FIG. 11, a cutaway side view of the molded gripping device 126 is illustrated along line B. The edges of the cut out area 132 have been beveled to allow for a better grip on the syringe cap 32. Either of the two embodiments can be incorporated with equal efficiency, however, this should not in anyway limit the scope of the invention and any method of gripping and retaining the syringe cap 32 can be utilized.

The repositioning area 124 contains no sensors and serves to allow the robot 2001 to release and regrip the syringe 30 at a predetermined level. This is required because in the process of removing the syringe cap 32 the fingers are subject to slide upward on the syringe 30. The regripping process allows the robot PC to know how far the fingers are from the tip of the syringe 30 in order to judge how far to insert the syringe 30 into the analyzer, as described further herein.

Figure 14:
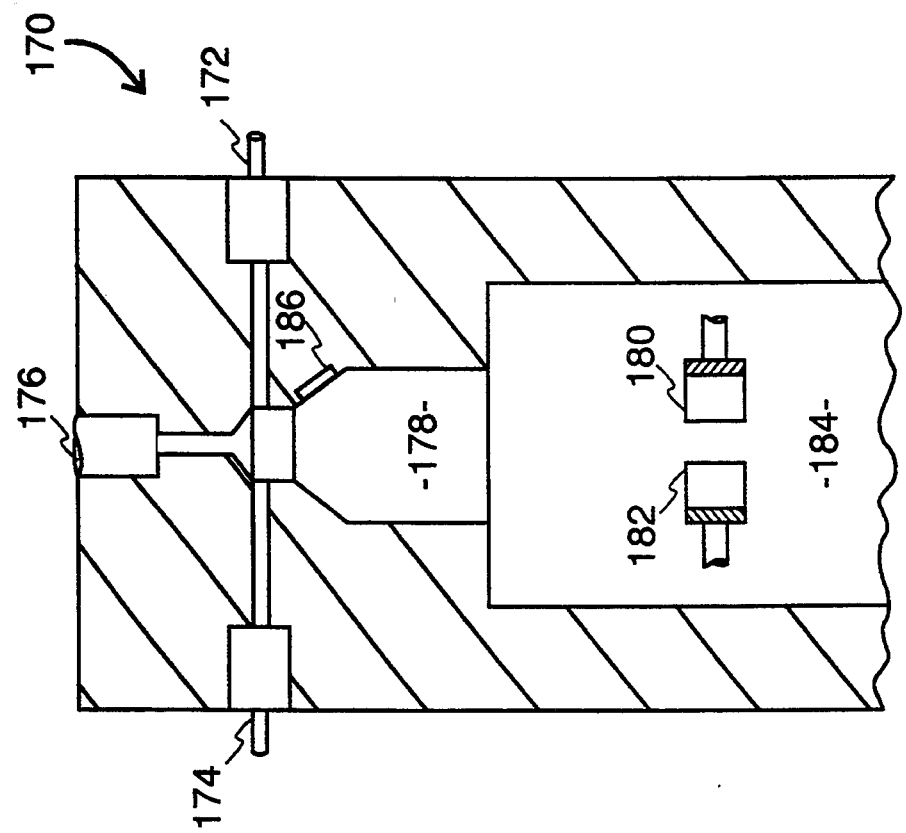
FIG. 14 is a fragmentary, sectional side view of a portion of the air aspirator member of the instant disclosure.
Figure 13:
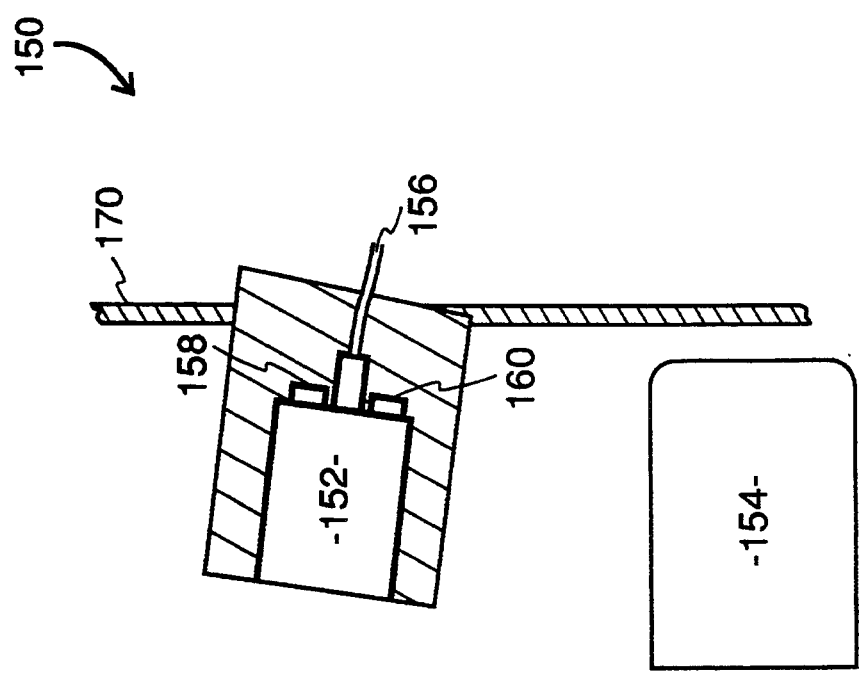
FIG. 13 is a fragmentary side view, partly in section of the analyzer targeting device of the instant disclosure.

Once the robot PC has confirmed that the syringe 30 is gripped properly, the syringe 30 is removed and inserted into the targeting device 150, FIG. 13, which has been attached to the analyzer 170 FIG. 14. The syringe 30 is inserted into the syringe receiving area 152 and held in position by the robot. The sensor 158 and sensor 160 indicate that the syringe 30 is properly placed in the syringe receiving area 152. The probe access area 156 is in contact with the syringe receiving area 152 and when the sensor 158 indicates to the environment computer that placement is secured, the analyzer 170 is activated to withdraw the blood sample. The information is fed into the interface cards and then to the environment computer. The analyzer 170 is of a standard design known in the industry and the targeting device 150 can be adapted to any of these designs. The targeting device 150 is an independent unit which consists of the targeting device 150 and a transmitter 154. The targeting device 150 and transmitter 154 must be electronically attached to one another in a manner to prevent disconnection. Additionally, the targeting device 150 must be in movable proximity to the analyzer 170 to allow for access to the analyzer 170 entrance point for service and cleaning. The targeting device 150 and transmitter 154 can be attached to a base with the targeting device 150 being attached to a pneumatic arm which moves the targeting device 150 either down or to the side. Alternatively the targeting device 150 can be hingeably attached to an arm and require manual removal. The pneumatic arm would allow additional computer control, if desired. The transmitter 154 is equipped with the electronics which feed the sensor results to the environment computer. The transmitter 154 receives the acknowledgment that the syringe 30 is securely in contact with the sensor 158 as well as indications as to whether the targeting device 150 is in position. In order to indicate the positioning of the targeting device 150, there must be sensors and communication between the targeting device 150 and the transmitter 154. When the pneumatic arm is used, the feed back to the transmitter 154 can be though the same channels as the other arm controls. When the transmitter 154 is connected for manual removal, separate controls must be incorporated in the way of sensors or contacts. When the analyzer 170 has completed withdrawal of the samples, notification is given to the environment computer which, in turn, indicates to the robot 2001 to remove the syringe 30 from the targeting device 150.

The robot 2001 then takes the syringe 30 to the air aspirator 250 of FIG. 14 for removal of any air bubbles remaining after the sample is taken. The syringe 30 is inserted into the air aspirator 250 until the end of the syringe 30 is in the syringe tip receiving area 178 and indication of proper placement is given through sensor 186. Once the sensor 186 indicates contact, the environment computer closes the gripping fingers 180 and gripping fingers 182, located in the syringe body receiving area 184, to secure the syringe 30 within the air aspirator 250. The gripping fingers 180 and syringe body receiving area 184 must be padded and a control built in to prevent the gripping fingers 180 and gripping fingers 182 from crushing the syringe 30. This can be done in a number of ways well known to those versed in the art including, pulse magnetics. Once securement is registered, the robot 2001 releases the syringe 30 and grips the syringe 30 plunger. The robot 2001 pushes the plunger upward to expel any air until indicated to stop by the computer. Simultaneous with the robot 2001 pushing the plunger, the vacuum nozzle 176 pulls out the air and a small portion of the sample. The vacuum nozzle 176 is attached to a hose leading to a gathering receptacle. The vacuum device used with the vacuum nozzle 176 is of standard design and known in the prior art. The burper 170 as disclosed herein is not connected to the computer system and therefore does not interact with any of the other peripheral devices. The air withdrawal in the disclosed system works on a timer which is activated by the sensor 186. The vacuum nozzle 176 is activated for a predetermined period of time which will withdraw the air and some blood from the syringe 30. The air aspirator 170 can, alternatively, be equipped with one or more computerized means for indicating that the air has been removed from the syringe 30 if it is connected to the system. Optointerrupters can be placed within the air aspirator 170 level with the vacuum nozzle 176 to provide indication that nonreflective material is passing into the vacuum nozzle 176. Infra red, microswitches or air switches can be used as indicators.

Figure 15:
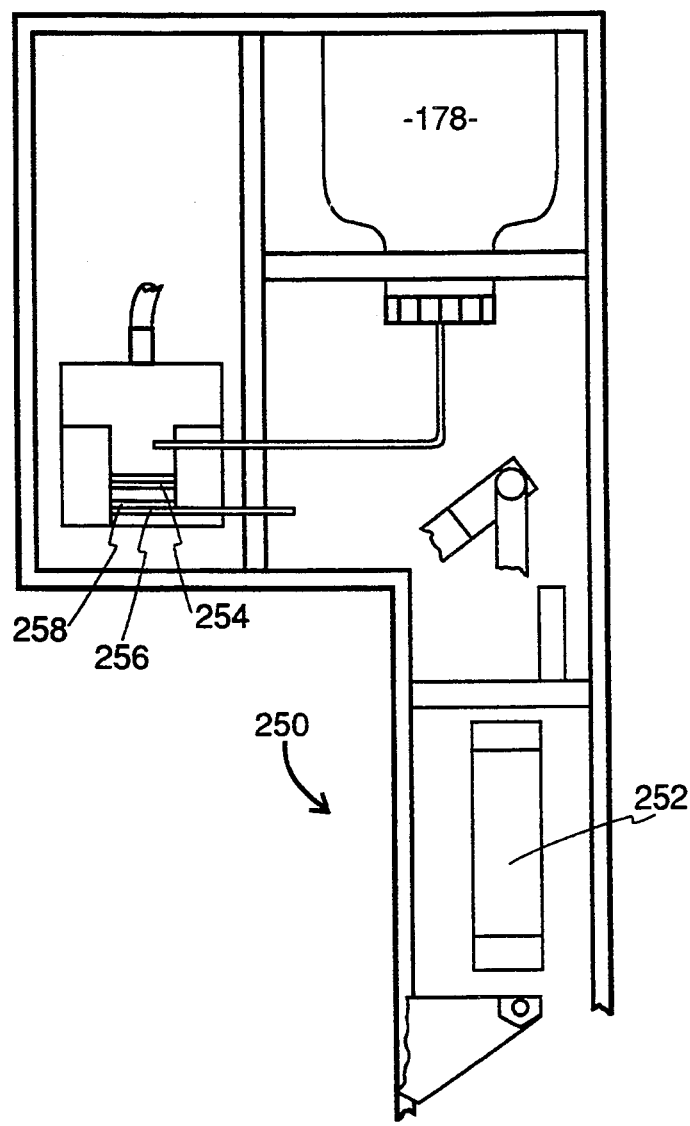
FIG. 15 is a side view of the air aspirator with an alternate gripping device.
Figure 16:
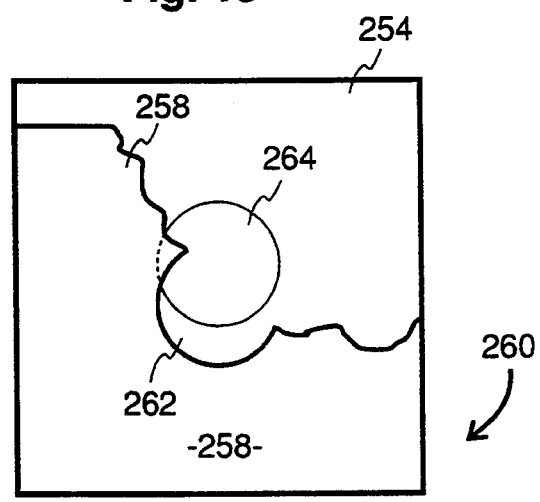
FIG. 16 is the gripping device of FIG. 15.

FIG. 15 illustrates the air aspirator 250 in a complete side view. The pneumatics 252 are used to activate a preferred gripping device 260 for the syringe 30. The gripping device 260 consists of plates 254, 256 and 258. Plate 254 is connected to a device which can slide the plate 254 a small distanced. In the embodiment disclosed herein pneumatics 252 are use, however any device which is known in the prior art can be used. The plates 254, 256 and 258 are placed on top of one another with a hole 262, 264 and 266 (not shown) through the center. When all plates 254, 256 and 258 are in the insert position the holes 262, 264 and 266 are aligned. Once the sensor is activated, the pneumatics 252 move the center plate 254 a small distance to be off center with the remaining plates 256 and 258. This places the holes 262 and 266 still in alignment with the hole 264 being off center, as illustrated in FIG. 16, thereby gripping the syringe 30. The movement of the plates 254, 256 and 258 must be carefully calibrated to prevent the syringe 30 from being crushed. The preferred method is to move the middle plate 254, thereby allowing the syringe 30 to be held in a vertical position by plates 256 and 258.

When either the allotted time is expended or all the air is removed from the syringe 30, depending upon which system is used, the environment computer signals the robot PC to tell the robot 2001 to release the plunger and regrip the syringe 30. Once the robot 2001 has gripped the syringe 30, the signal is sent to the gripping fingers 180 and gripping fingers 182 to release the syringe 30.

Upon removal of the syringe 30 from the air aspirator 170 the cleaning system is activated. The water cleaning nozzle 174 and air cleaning nozzle 172 force water and air into the syringe tip receiving area 178, the air and water being removed by the vacuum nozzle 176. This cleaning action prevents any possible contamination of future specimens as well as clogging of the apparatus.

Once the robot 2001 removes the syringe 30 from the air aspirator 170 it is returned to the decapper 120. The syringe 30 is inserted into the decapper 120 and the decapping process is reversed, thereby reaffixing the syringe cap 32 to the syringe 30. Upon removal of the syringe 30 from the decapper 120, the sensors verify that the syringe cap 32 has been removed with the syringe 30. The syringe 30 is moved to a position over the specimen storage device 34. The initial process for entering the specimen storage device 34 is repeated to allow the robot 2001 to return the syringe 30 to its specimen storage device clip 38.

Figure 17:
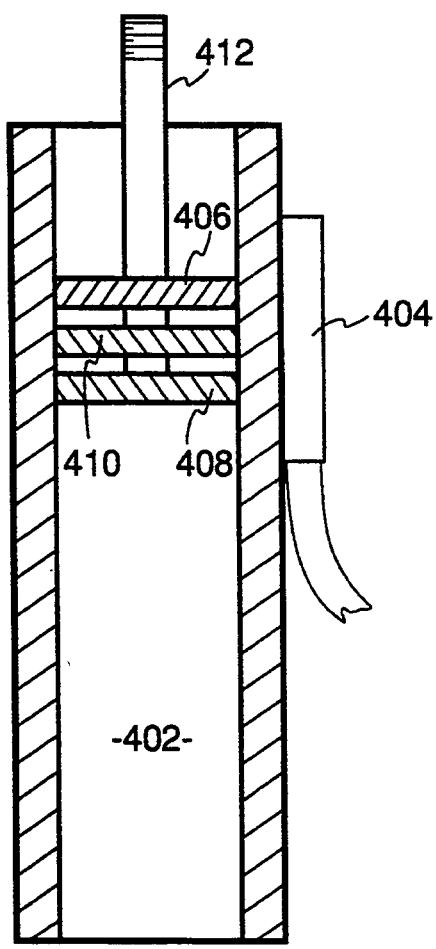
FIG. 17 is a side view the sensor to be used with the pneumatics.

FIG. 17 illustrates a Hall effect sensor for use with the pneumatics in the instant disclosure. Rubber seals 406 and 408 are placed on ether side of magnet 410. When the plunger 412 moves the magnet 410 past the Hall effect sensor 404, the sensor sends a signal which is read by the computer.

Figure 19:
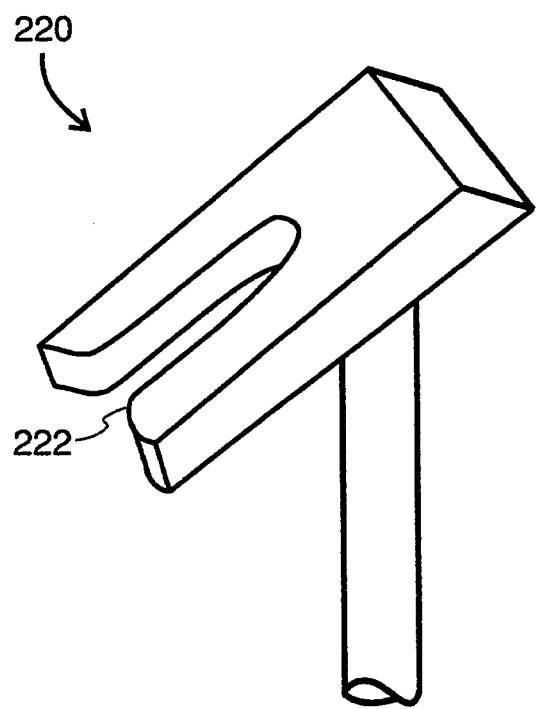
FIG. 19 is a perspective view of the zero point locating device of the instant disclosure.
Figure 18:
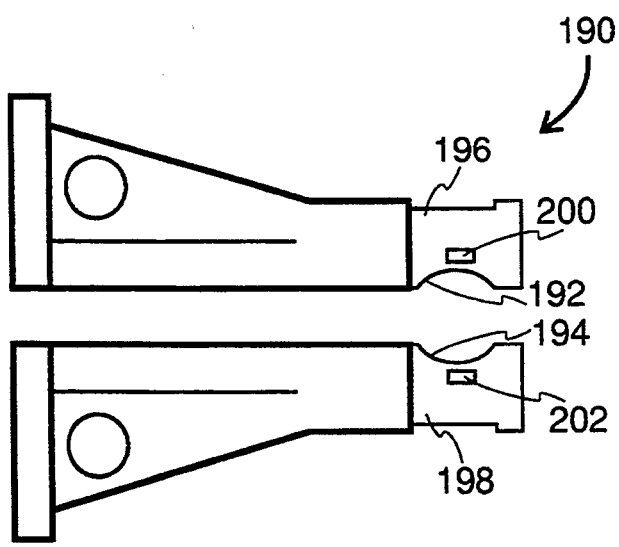
FIG. 18 is a plan view of the robot fingers of the instant disclosure.

The robot arms 190, of FIG. 18, of the robot 2001 is provided with finger 196 and finger 198. The fingers 196 and 198 are equipped with curved syringe grasping region 192 and curved finger 194, respectively, to accommodate the shape of the syringe 30. The robot arms 190 are removable from the robot 2001 and can be changed to correspond to the size of the syringes used. The curved finger 192 and curved finger 194 have been designed to accommodate a syringes up and down one size from the size used herein. The ability to remove the robot arms 190 in the event either larger syringes are used or other materials are to be gripped and moved is critical to the versatility of the disclosure. The finger sensor elements 200 and 202 enable the robot arms 190 to verify that a syringe has been picked up and/or released. In an alternate embodiment, the finger sensor element 200 and finger sensor element 202 are pressure sensitive and can adjust to the size of the object to be gripped as well as prevent breakage FIG. 19 illustrates the zero point locating device 220 which used to verify proper location of the fingers 196 and 198 of the robot 2001. All of the maneuvers of the robot 2001 are based on distances from a starting point, or zero point. As mechanics are used, slight wear can throw the distancing off enough to prevent the robot 2001 from functioning properly. The zero point locating device 220 operates to check the distancing after each completed function, verifying that the arms are properly aligned. After each analytical series, the robot 2001 returns to the zero point locating device 200 and places its robot arms 190 into the arm receiving slot 222. A sensor within the zero point locating device 220 acknowledges the zero point position, thereby reaffirming that the proper alignment has been reached.

FIG. 20 illustrates an alternate embodiment to the mixer 34. The alternate mixer 334 is formed with solid mixer ends 340 replacing diagonal supports 52a and 52b. The solid mixer end 340 is provided with insert 358 in the center into which the block 354 is inserted. The block 354 is provided with shaft insert 352 and a locking nut 350. The shaft 346 is inserted into the shaft insert 352 and locked into position with the locking nut 350. A release pin 356 prevents the block 354 from sliding out of the insert 358. The stops 348a, 348b, 348c, 348d are drilled or molded into the mixer ends 340 to allow for insertion of the stop locking bar 60. The top support rail 342 and the bottom support rail 344 are manufactured with mixer clips 338 as described in FIGS. 3 and 4.

FIG. 21 is a plan view of the robotics table 1000. The sliding door 1002 can be seen in the open position, having been activated to the open position by the User Interaction Station. The mechanically moved by the pneumatics 1004 and connecting rod 1006. Once the syringe 30 is placed in the receiving area 12, the computer is told to activate the pneumatics 1004 to close the door 1002. The door 1002 and corresponding pneumatics 1004 are all commercially available and known to one versed in the prior art. The positioning of the various remaining elements composing the instant disclosure can be seen in proper placement.

Figure 22:
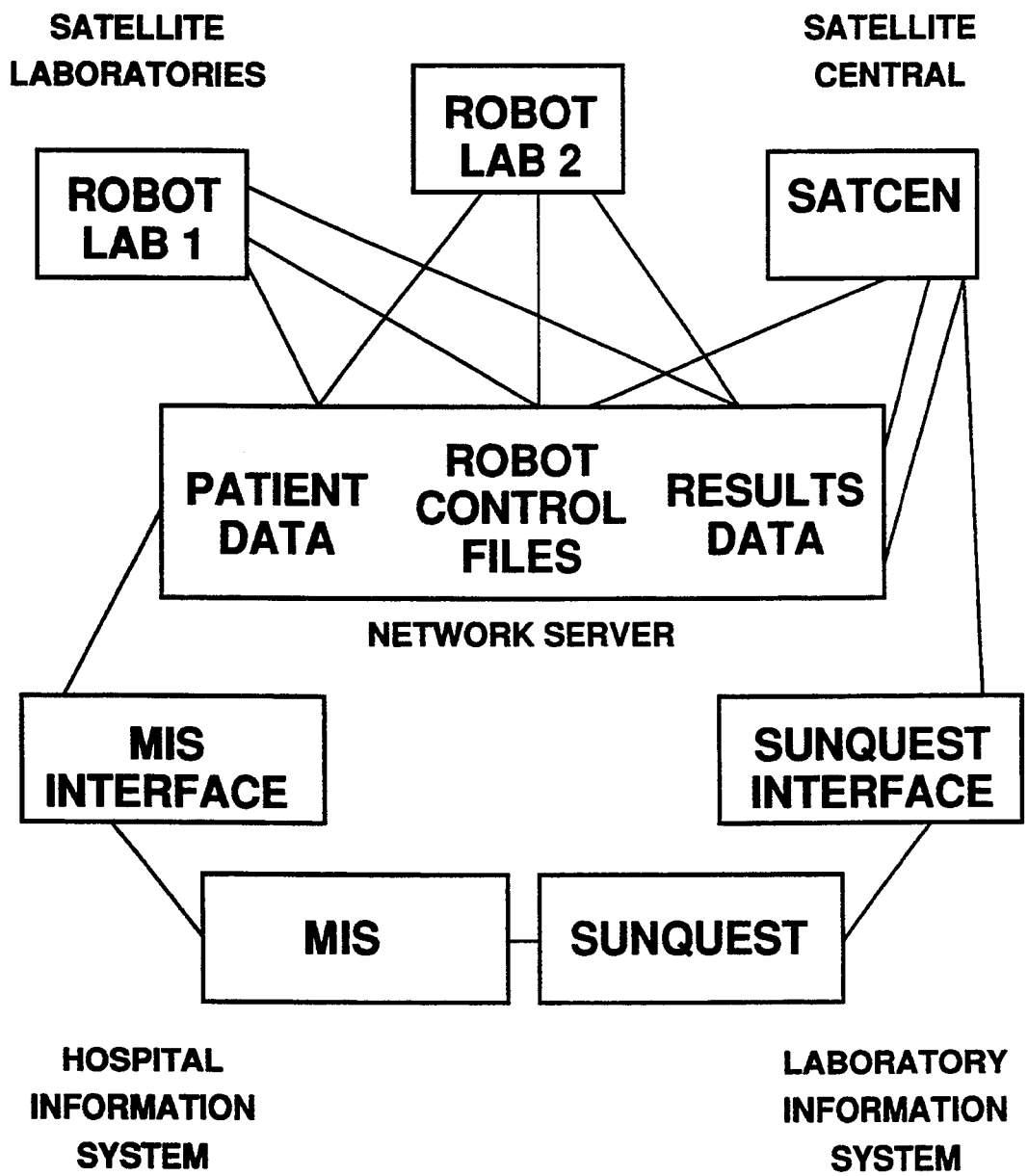
FIG. 22 is a flow diagram of the computer system.

FIG. 22 is a flow diagram of the completed robot laboratory system. Information is entered into SATCEN where it is able to constantly receive information directly from the Results Data area. Inquiries are directed from SATCEN through Robot Control Files to be received in either robot lab 1 or robot lab 2. Information from the hospital information system is fed to the robot labs through the patient data. Once tests are completed at the robot labs, results are sent to SATCEN for analysis. From SATCEN the accepted results are sent to SUNQUEST.

Figure 23:
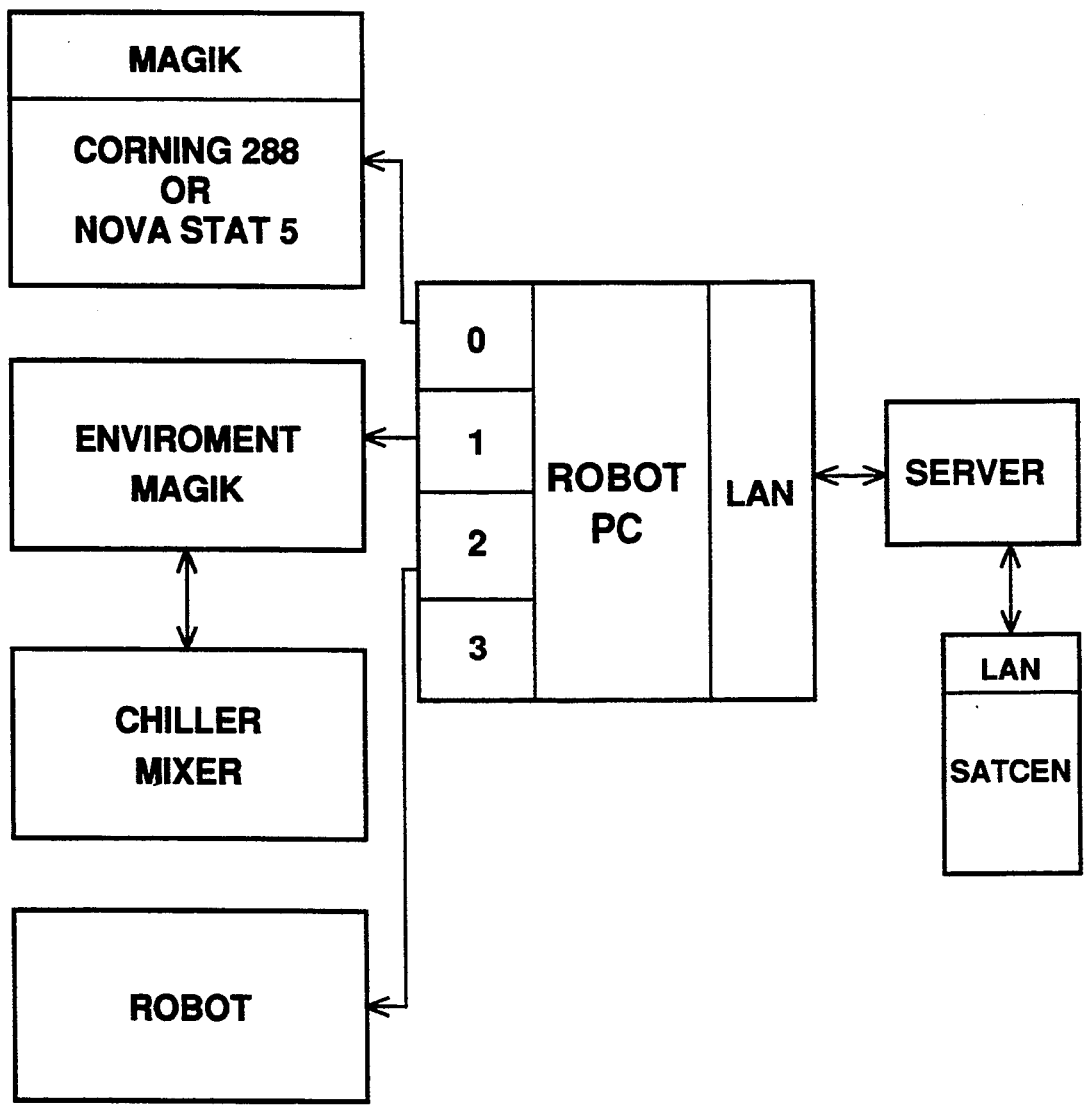
FIG. 23 is a flow diagram of the robot laboratory.

FIG. 23 is a flow diagram of the computer operations of a satellite laboratory operation. Inquires from the Server are fed to the Robot PC. Information is fed back and forth from the Robot PC to the robot and auxiliary software and equipment. Final results are sent to the Server and approved analysis are sent then to SATCEN.

The results received from the analyzer 170 are sent, through the robot PC, to a trained technician in satellite central (SATCEN). The technician reviews the results of the test and makes the decision to either accept the results or request a retest. In the event a retest is requested, a "repeat" order is entered and the robot PC repeats the initial testing. If the test results are unquestionable, the technician enters an order to accept the results, indicating to the robot PC that the sample can be discarded and the patient files updated. In response to an accept order, the robot PC, upon availability, removes the specimen from the specimen storage device 34 and discards it in a biological waste container. In the event there is what appears to be a continued error in the patients testing, the technician can place a failed order on the sample and have the sample held for personal inspection.

The pneumatics with sensors are used in the capper, access door, mixer door, burper lock and the mixer. Two sensors are used on each cylinder, one for sending when the piston is all the way out and one for sensing whether the piston is all the way in. If the piston is in-between sensors, this registers a pending status, thereby allowing the mechanics to catch up to the electronics.

It should be noted that the sensors used in the instant invention can be either optical, Hall effect (for the pneumatics), pressure sensors, or the like.

The computers are constantly checking each of the sensors and other sending devices to check for "yes" signals. Three types of signals are sent from all sending devices; "yes", "no" and "pending". If action is required, a "yes" signal is sent; if the sending device is dormant "no" is sent and if the required action is in process a "pending" signal is sent. Due to the speed of the computers, thousands of checks can be done each second, thereby eliminating any delay between processes. Once a command to proceed from one step to the next is received a confirmation command is requested to insure that all prerequisites have been met before proceeding.

The source code for the program which operates the robot and the peripheral equipment is provide hereinafter.

The pneumatics with sensors are used in the capper, access door, mixer door, burper lock and the mixer. Two sensors are used on each cylinder, one for sending when the piston is all the way out and one for sensing whether the piston is all the way in. If the piston is in-between sensors, this registers a pending status, thereby allowing the mechanics to catch up to the electronics.

It should be noted that the sensors used in the instant invention can be either optical, Hall effect (for the pneumatics), pressure sensors, or the like.

The computers are constantly checking each of the sensors and other sending devices to check for "yes" signals. Three types of signals are sent from all sending devices; "yes", "no" and "pending". If action is required, a "yes" signal is sent; if the sending device is dormant "no" is sent and if the required action is in process a "pending" signal is sent. Due to the speed of the computers, thousands of checks can be done each second, thereby eliminating any delay between processes. Once a command to proceed from one step to the next is received a confirmation command is requested to insure that all prerequisites have been met before proceeding.

The source code for the program which operates the robot and the peripheral equipment is provide hereinafter.

COMPUTER PROGRAMS

```
COMPUTER SOURCE CODE FOR STAND ALONE SYSTEM            #include <dos.h>

/****************************************************   #include <mem.h>
``` program to allow NOVA to run as a STAND ALONE SYSTEM with results saved to Paradox database, Written in Turbo C, compiled with Turbo C. Program name is NOVAUIS.C

**********************************************/

```c
#include <stdio.h>
#include <stdlib.h>
#include <string.h>
#include <conio.h>
#include <fcntl.h>
#include <sys\types.h>
#include <sys\stat.h>
#include "pxengine.h"
#include "nova_scr.h"
#include "boolean.h"
#include "longtime.cf"
#include "structs.c"
#include "defines.c"
#include "novasub.c"

#define INIT      "init"
define MODE      "mode pad"
#define SCALE     "scale 80 24"
define SCREEN_TIMEOUT    180 unsigned char scrn_buf[BUF_SIZE],wr_buf;

static char iobuf1[256];

static char iobuf2[256];

char rd_term[] = {NULL, NULL, NULL, '>', EOT};

#include <ctype.h>
#include <time.h>
#include <io.h>
#include <bios.h>
#include <asynch_1.h>
#include "pxengine.h"
#include "asy_ksm.h"
#include "nova_irq.h"
#include <graphics.h>

TABLEHANDLE results_tblHandle,patient_tblHandle;

main()
{
  int i,handle,pxErr,counter;
  char entry[0x10],key;

cursor_off();

if((handle = open("TCH_SCRN", O_BINARY|O_RDONLY,
  S_IREAD)) == -1)
  {
    perror("driver not installed");
    exit(0);
  }
  close(handle);

if((handle = open("TCH_SCRN", O_BINARY|O_RDWR,
  S_IWRITE)) == -1)
  {
    perror("driver open error");
    exit(0);
```

```c
char wr_term[] = {NULL, NULL, NULL, CR, EOT};

char rob_set[] = {0x09,0x12,NULL};

void interrupt (*old_handle)();

int timeout[] = {NULL,NULL,NULL,25,2};

char MIS_number[10];

int send_Nova_MIS_number = 1,loop,yes=0;

void init_list(),roledsp();

int role(),wrole();

int find_history_number(),sample_conditions();

static int function_choice;

pad_define_conditions(handle);

pad_define_activate(handle);

pad_define_nova_mdo(handle);

pad_define_current_results(handle);

pad_define_previous_results(handle);

pad_define_analyze_view(handle);

/** open communications with the Nova ***/ setmem(scrn_buf,BUF_SIZE,SPACE);

bioscom(0,0xe3,0); /* COM1 set up as 9600,n,8,1 */ old_handle = getvect(COMM_IRQ);

rec_irq_enable();

rts_on();

/******************************************* pxErr = PXInit();

********************************************/

}

/* set up driver functions & load pads */ touch(handle,INIT,entry);

touch(handle,SCALE,entry);

pad_define_logsc(handle);

pad_define_history(handle);

pad_define_history_accept(handle);

pad_define_history_not_found(handle);

pad_define_clear(handle);

pad_define_units(handle);

pad_define_patients(handle);

pad_define_confirm(handle);

getch();

exit(0);

} pxErr = PXTblOpen(PATIENT_DATA_FILE,&patient_tblHandle,0,0-);

if (pxErr)

{ printf("Error opening patfile.db - error: %d\npress any key",pxErr);

getch();

exit(0);

}

/********* send DELETES to Nova to get to READY
FOR ANALYSIS screen ***/
```

```
/******************************************/ pxErr = PXNetInit("h:\\",THREECOMNET,NULL);

/********************************************/ if (pxErr)

{ printf("\n\n\n\n                NOT ON THE
NETWORK, ERROR: %d",pxErr);

exit(0);

} pxErr =
PXTblOpen(RESULTS_FILE,&results_tblHandle,0,0);

if (pxErr)

{ printf("Error opening results.db - error: %d\n
press any key",pxErr);

function_choice = logscrn(handle);

if (function_choice == 12)

{ break;

} if (function_choice != 9)

{ function_choice =
analyze_view(handle);

} loop = 0;
```

```
for(i=0;i<4;i++)

{ delay(100);

outportb(COMM_BASE,DEL);

} outportb(COMM_BASE,'H');

delay(100);

outportb(COMM_BASE,DEL);

delay(2000);

function_choice = 0;

do

{ switch(function_choice)

{ case 0:

case 3:

function_choice =
role(handle,patient_tblHandle);

break;

case 4:

function_choice =
find_history_number(handle,patient_tblHandle);

break;

case 5:

function_choice = mis_entry(handle);

break;
```

```
            break;

case 1:

do

{ function_choice = check_instrument();

} while (function_choice);

if (loop)

{ function_choice = 0;

} else

{ function_choice = 2;

} break;

case 2:

function_choice = wrole(handle);

break;

{ function_choice = 0;

} yes=0;

break;

case 8:

function_choice =
check_status_of_instrument(handle,results_tblHandl-
e);

case 6:

function_choice = sample_conditions(handle);

break;

case 7:

counter = 0;

do

{ function_choice = check_instrument();

counter++;

} while (function_choice);

if (counter == 1)

{ initialize_instrument();

function_choice = 8;

puts("\377\377display/");

} else if (kbhit())

{ key = getch();

}

} while (key != 'q');

shut_down(old_handle);

}

/************************* end main() *******/
```

```
        break;

case 9:

nova_mdo(handle);

function_choice = 0;

break;

case 10:

function_choice =
    view_results(handle,results_tblHandle);

break;

case 11:

results_screen(handle,results_tblHandle);

function_choice = 0;

break;

case 12:

idle_screen(handle);

function_choice = 0;

break;

} /* end switch */ do

{ /* while(x) */
do

{ time(&start_time);
```

```
/************************************************
                            logscrn()
************************************************/ int logscrn (int handle)

/* display logon screen, accept logon code */

{
  char entry[0x10],fld[6];

int i,x=1,count=0,row=3,col=65,length=5;

long start_time,now_time;

function_choice = 1; /* call check_instrument
next, unless tech calls MDO */ load_pic_numbers();

touch(handle,"group all off",entry);

touch(handle,"group 1 on",entry);

puts("\377\377logscr/");

puts("\377\377login/");

textbackground(BLACK);

textcolor(WHITE);

strcpy(fld,"      ");

break;

case '0':

case '1':

case '2':

case '3':
```

```
do

{ /* find first touch screen strike */ touch(handle,MODE,entry);

if (time(&now_time) > (start_time +
SCREEN_TIMEOUT))

{ return(12);

}

} while (entry[0] != 'F');

switch(entry[2])

{ case 'C':

beep(850);

touch(handle,"group all
off",entry);

touch(handle,"group 1 on",entry);

puts("\377\377login/");

textbackground(BLACK);

gotoxy(64,3);

cprintf("           ");

col = col - count;

count = 0;

strcpy (fld,"      ");

break;

case 'E':

beep(800);

for (i=0;i<SIZE;i++)
```

```
      case '4':

case '5':

case '6':

case '7':

case '8':

case '9':

beep(700);

if (count < length)

{ gotoxy(col++,row);

cprintf ("%c",(fld[count++] =
entry[2]));

} else

{ beep(550);

} /* too many input */ break;

} /* end switch */

} while (entry[2] != 'E');

if (count)

{ fld[count] = '\0';

}

/**** add check for tech id to do MDO ********/

/************************************************ analyze_view()
```

```c
{
  if (!strcmp(fld,pic_numbers[i].pic_number))
  {
    x=0;
  }
} /* end for (i=0 ... */ if (x)
{
  touch(handle,"group all off",entry);
  touch(handle,"group 5 on",entry);
  puts("\377\377nopic/");
  gotoxy(65,3);
  cprintf("%s",fld);
}

} while(x);

strcpy(data.pic_number,fld);

if (!strcmp(fld,"1000")) /* code number to get
into the mdo() */
{
  function_choice = 9;
  return(function_choice);
} return(function_choice);

}

/******************* end logscrn() ***********/
```

```c
*************************************************/ analyze_view(int handle)

{
  char entry[0x10];
  int j=0,x=1;
  long start_time,now_time;

touch(handle,"group all off",entry);
  touch(handle,"group 14 on",entry);
  puts("\377\377analview/");

do
  { /* while(x) */
    time(&start_time);
    do
    { /* find first touch screen strike */
      touch(handle,MODE,entry);
      if (time(&now_time) > (start_time +
SCREEN_TIMEOUT))
      {
        return(0);
      }
    } while (entry[0] != 'F');

switch(entry[2])
      {
      case 'A':
          beep(850);
          function_choice = 1;
          x = 0;
          break;
```

```
                beep(800);

function_choice = 10;

x = 0;

break;

} /* end switch */

} while (x);

return(function_choice);

}

/********* end analyze_view() ***********/

/**********************************************
        picinit_list()
**********************************************/
picinit_list ()
/* pic array initalization for reading files */
{
    register int t;

for (t=0;t<SIZE;t++)

{

*pic_numbers[t].pic_number='\0';

}

}

/******* picinit_list() ***************/
```

```
        case 'S':

register int i;

int last;

FILE *fp;

last = 0;

if ((fp=fopen(PIC_NUMBER_FILE,"rb"))==NULL)

{ printf ("cannot open file\n");

return (0);

} picinit_list();

for (i=0,last=0;i<SIZE;i++,last++)

if (fread(&pic_numbers[i],sizeof(struct picnumber),1,fp)!=1)

{ if (feof(fp))

{ fclose(fp);

return (last - 1);

}

}

}

/******* end load_pic_numbers() **********/

/**********************************************
                                    wroledsp()
*****************************************/
void wroledsp (b,e,bar)
/* displays lists of wards in bar menu form */
    int b,e,bar;
```

```c
/********** load_pic_numbers()

*****************/ int load_pic_numbers()

/* load data from the PIC numbers file */

{

{ if (x==bar)

{ textbackground (6);

} gotoxy(5,row++);

cprintf (" %-7s",unit[x].ward);

textbackground (7);

}

}
/*          end wroledsp()    */

/******************************************
            winit_list()
******************************************/
void winit_list ()

{ register int t;

for (t=0;t<SIZE;t++)

{

*unit[t].ward='\0';

}

}
```

```c
{ int x,row=6;

textbackground (7);

for (x=b;x<=e;x++)

register int i;

int last;

FILE *fp;

last = 0;

if ((fp=fopen(filename,"rb"))==NULL)

{ printf ("cannot open file\n");

return (0);

} winit_list();

for (i=0,last=0;i<SIZE;i++,last++)

if (fread(&unit[i],sizeof(struct recc3),1,fp)!=1)

{ if (feof(fp))

{ fclose(fp);

return (last - 1);

}

}

}
/*                        end wload()     */
```

```
/*******************************
          wload()
*******************************/ int wload(filename)
/* load data from the chosen ward demographic file
*/
char filename[32];
{
int j=0,exit=0,freq=0;
long start_time,now_time;

touch(handle,"group all off",entry);

touch(handle,"group 6 on",entry);

puts ("\377\377units/");

recend = wload(UNIT_FILE);

recbgn=0;

wndbgn=0;

ptr=0;

bar=0;

dsplyend = DISP_CNT;

wndend = DISP_CNT;  /* total number of units in
hospital */ textbackground(0);

textcolor(15);

gotoxy(64,3);

cprintf("%s",unit[bar].ward);

wroledsp (recbgn,dsplyend,bar);
```

```
/*********************************************
                wrole()
*********************************************/ int wrole (int handle)
/* routine to read wards and display them */
{
  static int
dsplyend,wndend,recbgn,wndbgn,recend,ptr,bar;
  char entry[0x10];

if ((entry[2] == 'U') || (entry[2] == 'D'))
    {
      textbackground(0);
      gotoxy(64,3);
      cprintf("          ");
    } switch(entry[2])
    {
    case 'D':
        freq = 680;
        if (ptr >= recend) beep(550);
        else
        {
            if (ptr++ >= wndend)
            {
                wndbgn++;
                wndend++;
            }
            bar++;
            wroledsp (wndbgn,wndend,bar);
```

```c
        do
          {
          time(&start_time);
          do
            {
            touch(handle,MODE,entry);
            if (time(&now_time) > (start_time +
SCREEN_TIMEOUT))
              {
              return(0);
              }
            } while (entry[0] != 'R');
                --bar;
                wroledsp (wndbgn,wndend,bar);
            }
          break;

case 'H':
                beep(800);
                function_choice = 4; /* set to
call find_history_#() */
                exit = 1;
                break;

case 'E':
                beep(800);
                strcpy(data.unit,unit[bar].ward);
                function_choice = 3; /* set to call
role() */
                exit = 1;
```

```c
                }
                break;

case 'U':
                freq = 700;
                if (ptr <= 0) beep(550);
                else
                  {
                  if (--ptr <= wndbgn - 1)
                    {
                    --wndbgn;
                    --wndend;
                    }
                  }
        return(function_choice);

}
/************* end wrole() ****************/

/*******************************************
                roledsp()
********************************************/
void roledsp (b,e,recend,bar)
/* displays lists of patients in bar menu form */
        int b,e,recend,bar;
        {
        int x,count=0,row=6;
        highvideo ();
        textbackground (7);

for (x = b; x <= e; x++)
```

```c
      break;

} /* end switch */ if (freq)

{ sound(freq);

textbackground(0);

textcolor(15);

gotoxy(64,3);

cprintf("%s",unit[bar].ward);

delay(200);

nosound();

freq = 0;

}

} while (!exit);

/*********************************************
                role()
*********************************************/
int role (int handle,TABLEHANDLE patient_tblHandle)
/* routine to read *** ward (unit) *** patients and
display them */
{
  static int
dsplyend,wndend,recbgn=0,wndbgn=0,recend,ptr=0,bar=0;

int o,p,patients_in_unit=0,pxErr,exit=0,freq=0;
  char
entry[0x10],*prt_o1,*prt_o2,*prt_p1,*prt_p2,*temp=NULL;

{
        if (x==bar)
        {
          textbackground (6);
        }
        if(count++ > recend - 1)
        {
          break;
        }
        gotoxy(5,row++);
        cprintf (" %-20s          %-10s
",pat_rec[x].nme,pat_rec[x].id);
        textbackground (7);
      }
    }
/******** end roledsp() ********/ do
    {
      if(pxErr =
PXSrchFld(patient_tblHandle,recHandle,FIELDUNIT,
            SEARCHNEXT) == PXSUCCESS)
      {
        PXRecGet(patient_tblHandle,recHandle);

PXGetAlpha(recHandle,FIELDPATIENTNAME,21,pat_rec[p-
atients_in_unit].nme);

PXGetAlpha(recHandle,FIELDHISTORYNUMBER,11,pat_rec-
[patients_in_unit].id);
        patients_in_unit++;
      }
```

```c
long start_time,now_time;

RECORDHANDLE recHandle;

PXRecBufOpen(patient_tblHandle, &recHandle);
    PXPutAlpha(recHandle,FIELDUNIT,data.unit);

if(pxErr =
PXSrchFld(patient_tblHandle,recHandle,FIELDUNIT,
            SEARCHFIRST) == PXSUCCESS)
    {
        PXRecGet(patient_tblHandle,recHandle);

PXGetAlpha(recHandle,FIELDPATIENTNAME,21,pat_rec[p-
atients_in_unit].nme);

PXGetAlpha(recHandle,FIELDHISTORYNUMBER,11,pat_rec-
[patients_in_unit].id);
        patients_in_unit++;
    } cprintf(" UNIT: %s ",data.unit);
    strcpy(data.unit,"");
    strcpy(pat_rec[bar].nme,"                    ");
    function_choice = 2;
} else

{

/************* sort the patient's name in as-
cending order *****************/ for (o=0;o<(patients_in_unit-1);o++)
```

```c
    } while(pxErr);

PXRecBufClose(recHandle);

ptr = 0;
    bar = 0;
    recbgn = 0;
    wndbgn = 0;
    recend = patients_in_unit;
    dsplyend = WD_CNT;
    wndend = WD_CNT;

if (!patients_in_unit)
    {
        puts ("\377\377nopatient/");
        touch(handle,"group all off",entry);
        touch(handle,"group 5 on",entry);
        gotoxy(58,14);
        textbackground(BLUE);
        textbackground(BLUE);
        cprintf(" UNIT: %s ",data.unit);
        textcolor(15);
        textbackground(0);
        gotoxy(56,3);
        cprintf("%-20s",pat_rec[bar].nme);
        roledsp(recbgn,dsplyend,recend,bar);
    } do
    {
```

```c
{
    prt_o1 = pat_rec[o].nme;

prt_o2 = pat_rec[o].id;

for (p=o+1;p<patients_in_unit;p++)

{
        prt_p1 = pat_rec[p].nme;

prt_p2 = pat_rec[p].id;

if (strcmp(prt_p1,prt_o1) < 0)

{
            strcpy(temp,prt_o1);

strcpy(prt_o1,prt_p1);

strcpy(prt_p1,temp);

strcpy(temp,prt_o2);

strcpy(prt_o2,prt_p2);

strcpy(prt_p2,temp);

} /* end if (strcmp... */
    } /* end for (p=o+1... */
} /* end for (o=0  ... */

/* end sort
names */
    touch(handle,"group all off",entry);

touch(handle,"group 7 on",entry);

puts("\377\377patients/");

gotoxy(58,14);

else
                    {
                        if(ptr++ > wndend -
1)
                        {
                            wndbgn++;

wndend++;

time(&start_time);

do
    {
        touch(handle,MODE,entry);

if (time(&now_time) > (start_time +
SCREEN_TIMEOUT))
        {
            return(0);
        }
    } while (entry[0] != 'R');

if ((entry[2] == 'U') || (entry[2] == 'D'))
    {
        textbackground(0);

gotoxy(56,3);

cprintf("                    ");
    } switch(entry[2])
    {
        case 'D':

freq = 680;

if (ptr >= recend - 1)
beep(550);

strcpy
(data.history_number,pat_rec[bar].id);

function_choice = 5; /* set to
call mis_entry() */ exit = 1;

break;
```

```c
            }
            bar++ ;
            roledsp
(wndbgn,wndend,recend,bar);
        }
        break;

case 'U':
        freq = 700;
        if (ptr <= 0) beep(550);
        else
        {
            if (--ptr <= wndbgn
- 1)
            {
                --wndbgn;
                --wndend;
            }
            --bar;
            roledsp
(wndbgn,wndend,recend,bar);
        }
        break;

case 'E':
        beep(800);
        strcpy
(data.patient_name,pat_rec[bar].nme);

/*******************************************
            find_history_number()
```

```c
        case 'C':
        case 'X':
            beep(800);
            function_choice = 2; /* set to
call wrole() */
            exit = 1;
            break;

} /* end switch */ if (freq)
        {
            sound(freq);
            textbackground(0);
            textcolor(15);
            gotoxy(56,3);
            cprintf("%-20s",pat_rec[bar].nme);
            delay(200);
            nosound();
            freq = 0;
        }

} while (!exit);

return (function_choice);

}
/******** end role() ********/ switch(entry[2])
    {
        case 'C': /* clear the display input */
```

```c
/***********************************************/
int find_history_number(int handle,TABLEHANDLE
patient_tblHandle)
{
  RECORDHANDLE recHandle;
  int
j=0,exit=0,count=0,row=3,col=64,length=10,pxErr;
  char entry[0x10],fld[11];
  long start_time,now_time;

touch(handle,"group all off",entry);
  touch(handle,"group 2 on",entry);
  puts("\377\377history/");

textbackground(0);
  textcolor(15);

do
  { /* number 1 */
    do
    { /* number 2 */
      time(&start_time);
      do
      {
        touch(handle,MODE,entry);
        if (time(&now_time) > (start_time + SCREEN_TIMEOUT))
        {
          return(0);
        }
      } while (entry[0] != 'F');
```

```c
      beep(850);
      count=0;
      col=64;
      textbackground(BLACK);
      gotoxy(56,row);
      cprintf("           ");
      strcpy(fld,"          ");
      break;

case 'S': /* clear the display input */
      beep(750);
          touch(handle,"group all off",entry);
      touch(handle,"group 2 on",entry);
      puts("\377\377history/");
      textbackground(BLACK);
      count=0;
      col=64;
      strcpy(fld,"          ");
      break;

case 'X':
      beep(800);
      entry[2] = 'E';
      function_choice = 2; /* set to call wrole() */
      exit = 1;
      break;

case 'A':
      beep(800);
      entry[2] = 'E';
      function_choice = 5; /* set to call
```

```
                exit = 1;

break;

case 'E':

beep(800);

break;

case '0':
        case '1':
        case '2':
        case '3':
        case '4':
        case '5':
        case '6':
        case '7':
        case '8':
        case '9':

beep(700);

if (count < length)

{ gotoxy(col++,row);

cprintf("%c",fld[count++] =
entry[2]);

} /* end if (count... */ else

{ beep(550);

} break;

} /* end switch */
```

```
            mis_entry() */ return(function_choice);

} fld[count]='\0';

PXRecBufOpen(patient_tblHandle, &recHandle);

PXPutAlpha(recHandle,FIELDHISTORYNUMBER,fld);

pxErr =
PXSrchFld(patient_tblHandle,recHandle,FIELDHISTORY-
NUMBER,SEARCHFIRST);

if (!pxErr)

{

PXRecGet(patient_tblHandle,recHandle);

PXGetAlpha(recHandle,FIELDPATIENTNAME,21,data.pati-
ent_name);

PXGetAlpha(recHandle,FIELDHISTORYNUMBER,11,data.hi-
story_number);

PXGetAlpha(recHandle,FIELDUNIT,8,data.unit);

}

PXRecBufClose(recHandle);

if (!pxErr)

{ touch(handle,"group all off",entry);

touch(handle,"group 3 on",entry);

puts("\377\377keypad2/");

textbackground(BLACK);
```

```c
} while (entry[2] != 'E');   /* do while */ if (exit)

{ cprintf(" %s ",data.patient_name);

gotoxy(20,10);

cprintf(" %s ",data.unit);

} if (pxErr)

{ touch(handle,"group all off",entry);

touch(handle,"group 4 on",entry);

puts("\377\377nohistory/");

textbackground(BLACK);

gotoxy(64,3);

cprintf("%s",fld);

}

} while (!exit);   /* do while */ return(function_choice);

}
/*                        end find_history_number()
*/

/*****************************************************
                    mis_entry()
*****************************************************/ gotoxy(64,3);

cprintf("%s",data.history_number);

textbackground(BLUE);

gotoxy(20,8);

strcpy(fld,"              ");

textbackground(0);

textcolor(15);

touch(handle,"group all off",entry);

touch(handle,"group 1 on",entry);

puts("\377\377 mislog/");

do

{ time(&start_time);

do

{ touch(handle,MODE,entry);

if (time(&now_time) > (start_time +
SCREEN_TIMEOUT))

{ return(0);

}

} while(entry[0] != 'F');

switch(entry[2])

{ case 'C':

/* clear calculator display */ beep(850);
```

```c
int mis_entry(int handle)

{

RECORDHANDLE recHandle;

TABLEHANDLE tblHandle;

char temp_MIS_number[10],entry[0x10],fld[11];

int pxErr,x=1,count=0,row=3,column=64,length=10;

long assign_MIS_number,start_time,now_time;

/* accept entry as MIS id */ beep(800);

function_choice = 6; /* set to call sample_conditions() */ break;

case '0':

case '1':

case '2':

case '3':

case '4':

case '5':

case '6':

case '7':

case '8':

case '9':

beep(700);

if (count++ < length)

{ gotoxy(column++,row);

cprintf("%c",entry[2]);

}
        else count = 0;

column = 64;

gotoxy(56,row);

cprintf("                ");

strcpy(fld,"          ");

break;

case 'E':

{ do

{ pxErr = PXTblOpen(MIS_NUMBER_FILE,&tblHandle,0,0);

if (!pxErr)
            { /* recnum.db database table ready of access */
                PXRecBufOpen(tblHandle, &recHandle);

PXRecFirst(tblHandle);

PXRecGet(tblHandle,recHandle);

PXGetAlpha(recHandle,FIELDMISNUMBER,11,MIS_number);

strcpy(temp_MIS_number,MIS_number);

assign_MIS_number = atol(MIS_number);

assign_MIS_number++;

ltoa(assign_MIS_number,MIS_number,10);

PXPutAlpha(recHandle,FIELDMISNUMBER,MIS_number);

PXRecUpdate(tblHandle,recHandle);

PXRecBufClose(recHandle);

PXTblClose(tblHandle);

strcpy(MIS_number,temp_MIS_number);
```

```
            {
                beep(550);
            }
            break;
        } /* end switch */

} while (entry[2] != 'E');

/************ for AACC */
    count = 0;

if (!count)
    } while (x);

} if (count)
    {
        strcpy(MIS_number,fld); /* save MIS number in a safe place */
    } return(function_choice);

} /*                              end mis_entry()  */

/**********************************************
              sample_conditions()

**********************************************/
```

```
        x = 0;
    } /* end if (!pxErr) */ if (pxErr)
    { /* recnum.db database table in use, wait 2 seconds and try again */
        PXTblClose(tblHandle);
        delay(2000);
    }

/***********check uisdata.db for dups of entered MIS number !!!!! ***/ cprintf("%s",data.patient_name);
    gotoxy(21,8);
    cprintf("%s",data.history_number);
    gotoxy(21,9);
    cprintf("%s",MIS_number);
    gotoxy(21,10);
    cprintf("%s",data.unit);

gotoxy (6,13);
    cprintf ("Patient temperature:    37.0 C");
    strcpy(data.temp,"37.0");
    gotoxy (6,15);
    cprintf ("Patient FiO2 (in %%):    RA  %%");
    strcpy(data.fio2,"RA");
    gotoxy (6,17);
    cprintf ("Arterial or venous:    arterial");
    strcpy(data.sample_type,"A");

do
```

```c
int sample_conditions(int handle)

{ /* handles test and patient parameter (temp,
hemo) selection */ int stop = 1;

char entry[0x10];

long start_time,now_time;

touch(handle,"group all off",entry);

touch(handle,"group 9 on",entry);

puts ("\377\377tests1/");

highvideo();

textcolor(15);

textbackground(1);

gotoxy(21,7);

{ case 'V':

beep(800);

gotoxy (29,17);

if (!strcmp(data.sample_type,"A"))

{ cprintf ("venous ");

strcpy(data.sample_type,"V");
                }
            else

{ cprintf ("arterial");

strcpy(data.sample_type,"A");

}

{ time(&start_time);

do

{ touch(handle,MODE,entry);

if (time(&now_time) > (start_time + SCREEN_TIMEOUT))

{
            return(0);

}

} while (entry[0] != 'F');

textbackground(BLUE);

textcolor(WHITE);

switch(entry[2])

puts ("\377\377tests2/");

puts ("\377\377tests9/");

puts ("\377\377tests10/");
/*******************************************/ break;

case 'C':

beep(850);

gotoxy(21,7);

cprintf("%s",data.patient_name);

gotoxy(21,8);

cprintf("%s",data.history_number);

gotoxy(21,9);

cprintf("%s",MIS_number);

gotoxy(21,10);
```

```
                break;

case 'T':
                beep(800);
/*************************************
                calcpd (13,handle);
                touch(handle,"group all off",entry);
                touch(handle,"group 9 on",entry);
                puts ("\377\377tests2/");
                puts ("\377\377tests9/");
                puts ("\377\377tests10/");
**************************************/
                break;

case 'H':
                beep(800);
/*************************************
                calcpd (15,handle);
                touch(handle,"group all off",entry);
                touch(handle,"group 9 on",entry);

} while (entry[2] != 'E');

/******* confirmation screen ***********/
        touch(handle,"group all off",entry);
        touch(handle,"group 8 on",entry);
        puts ("\377\377confirm/");

gotoxy(21,7);
        cprintf("%s",data.patient_name);
        gotoxy(21,8);
```

```
                cprintf("%s",data.unit);
                gotoxy (6,13);
                cprintf ("Patient temperature:    37.0 C");
                strcpy (data.temp,"37.0");
                gotoxy (6,15);
                cprintf ("Patient FiO2 (in %%):    RA    %%");
                strcpy (data.fio2,"RA");
                gotoxy (6,17);
                cprintf ("Arterial or venous:    arterial");
                strcpy (data.sample_type,"A");
                textbackground(BLACK);
                gotoxy(56,3);
                cprintf("                    ");
                break;

case 'E':
                beep(800);
                break;

} /* end switch */

} do
    {
        time(&start_time);
        do
        {
            touch(handle,MODE,entry);
            if (time(&now_time) > (start_time +
SCREEN_TIMEOUT))
            {
```

```
cprintf("%s",data.history_number);

gotoxy(21,9);

cprintf("%s",MIS_number);

gotoxy(21,10);

cprintf("%s",data.unit);

gotoxy (6,13);

cprintf ("Patient temperature:    %s
C",data.temp);

gotoxy (6,15);

cprintf ("Patient FiO2 (in %%):    %s
%%",data.fio2);

if (!strcmp(data.sample_type,"A"))

{ gotoxy (6,17);

cprintf ("Arterial or venous:
arterial");

} else

{ gotoxy (6,17);

cprintf ("Arterial or venous:    venous
");

return(function_choice);

} /*                       end
sample_conditions()                */
```

```
    return(0);

}

} while (entry[0] != 'F');

switch(entry[2])

{ case 'X':

beep(800);

function_choice = 0; /* set to call
logsc() */ stop = 0;

break;

case 'E':

beep(800);

puts("\377\377keyoff/");

puts("\377\377covercon/");

function_choice = 7; /* set to call
check_instrument() */ stop = 0;

break;

}

} while(stop);

touch(handle,MODE,entry);

if (time(&now_time) > (start_time +
SCREEN_TIMEOUT))

{ return(0);

}

} while (entry[0] != 'F');
```

```
/*************************************************
                    calcpd()
*************************************************/ calcpd(int row,int handle)

/* calculator entry for patient temperature and hemoglobin in test screen */

{ char entry[0x10],fld[6];

int col=29,length=4,display_window=64,count=0;

long start_time,now_time;

touch(handle,"group all off",entry);

touch(handle,"group 1 on",entry);

puts ("\377\377keypad/");

puts ("\377\377keypad9/");

puts ("\377\377keypad10/");

gotoxy(col,row);

textbackground(BLACK);

cprintf ("__._");

strcpy(fld,NULL);

do

{ time(&start_time);

do

{ case '0':

case '1':

case '2':
```

```
        switch(entry[2])

{ case 'C':

/* clear input */ beep(850);

count = 0;

col = 29;

strcpy(fld,NULL);

gotoxy(col,row);

cprintf("__._");

display_window = 64;

textcolor(WHITE);

textbackground(BLACK);

gotoxy(display_window,3);

cprintf("            ");

break;

case 'E':

/* enter */ beep(800);

display_window = 64;

textcolor(WHITE);

textbackground(BLACK);

gotoxy(display_window,3);

cprintf("            ");

break;

} textbackground(BLACK);

gotoxy(display_window++,3);
```

```
            case '3':
            case '4':
            case '5':
            case '6':
            case '7':
            case '8':
            case '9':
                /* valid input */
                beep(700);
                if (count < length)
                {
                  if (col == 31)
                  {
                    col++;
                  }
                  gotoxy(1,1);
                  textcolor(WHITE);
                  textbackground(BLUE);
                  cprintf("%d",col);
                  textcolor(WHITE);
                  textbackground(BLACK);
                  gotoxy (col++,row);
                  cprintf ("%c",entry[2]);

if (display_window ==
66)
                  {
gotoxy(display_window++,3);
                    cprintf(".");
                    fld[2] = PERIOD;
```

```
                    cprintf("%c",fld[count++] =
                    entry[2]);
                  } /* end if (count++ < length)
                  */ else
                {
                  beep(600);
                } /* too many inputs */
                break;
            } /* end switch */

} while(entry[2] != 'E');

if (count)
        {
          fld[count] = '\0';
        } if (row == 13)
        {
          if (!strcmp(fld,NULL))
          {
            strcpy(data.temp,"37.0");
            textbackground(BLUE);
            gotoxy(29,row);
            cprintf("37.0");
          }
          else
          {
            strcpy(data.temp,fld);
```

```c
                count++;

} if (row == 15)

{ if (!strcmp(fld,NULL))

{ strcpy(data.fio2,"RA");

textbackground(BLUE);

gotoxy(29,row);

cprintf("RA ");

} else

{ strcpy(data.fio2,fld);

}

}

}
/********** end calcpd() **********************
            check_instrument()
*******************************/
check_instrument()
{ if ((!strstr(scrn_buf,NOVA_RFA) == NULL) |
      (!strstr(scrn_buf,"SEQUENCE ABORT") == NULL))
  {
   return(0);
  }
```

```c
  } loop++;

if (!strstr(scrn_buf,NOVA_GCIP) == NULL)

{ nova_display();

return(1);

} /* end if (!strstr(scrn_buf,"Gas Cal I in
Progress") */ if (!strstr(scrn_buf,"Gas Cal in Progress") ==
NULL)

{ nova_display();

return(1);

} /* end if (!strstr(scrn_buf,"Gas Cal in
Progress") */ if (!strstr(scrn_buf,NOVA_AGCIP) == NULL)

{ nova_display();

return(1);

} /* end if (!strstr(scrn_buf,"Auto_Cal in
Progress") */ if (!strstr(scrn_buf,NOVA_FCIP) == NULL)

{ nova_display();

return(1);

} /* end if (!strstr(scrn_buf,"Full Cal in
Progress") */
```

```
if (!loop)
{
    puts("\377\377display/");
}

} /* end if (!strstr(scrn_buf,"SEQUENCE ABORTED")
*/ return(function_choice);

}
/****** end check_instrument() *********/

/*************************************************
            initialize_instrument()
*************************************************/
initialize_instrument()
{ outportb(COMM_BASE,'A'); /* send Nova an 'A' to
extend probe */
    delay(100);
    delay(16000); /* wait for the Nova probe to ex-
tend */ outportb(COMM_BASE,'A'); /* send an 'A' to Nova
to aspirate sample */
    delay(6000);
    data.abort_flag = 0;
    send_Nova_MIS_number = 1;
```

```
    if (!strstr(scrn_buf,NOVA_SA) == NULL)
    {
        nova_display();
        return(1);
    {
        register i=0,j=0;
        char history_number[10];

function_choice = 8;
        gotoxy(1,1);
        cprintf("in check: %d ",yes++);

if (!strstr(scrn_buf,"Press CLEAR to exit.") ==
NULL)
        { /* wait for instrument washout and clear Nova
screen to READY FOR ANALYSIS */
            gotoxy(7,14);
            cprintf("Wash done");
            delay(100);
            outportb(COMM_BASE,DEL);
            delay(1000);
            function_choice = 0;
        }

/* DO NOT display the patient results *
        if (strstr(scrn_buf,"Acc. #") == NULL)
        {
        *************************/
            nova_display();
        /* } */
```

} /**** end initialize_instrument() *******/

/*********************************************
check_status_of_instrument()
**************************************************/
check_status_of_instrument(int handle,TABLEHANDLE results_tblHandle)

/* PATIENT DATA screen displayed, sample in instrument OK */ if (!strstr(scrn_buf,NOVA_PD) == NULL)
{
  puts("\377\377done/");
  if (send_Nova_MIS_number)
  {
    for (j=0;j<9;j++)
    {
      outportb(COMM_BASE,MIS_number[j]);
      delay(100);
    }
    outportb(COMM_BASE,CR);
    delay(100);
    strcpy(history_number,data.history_number);
    for (j=0;j<9;j++)
    {
      outportb(COMM_BASE,history_number[j]);
      delay(100);
    }
    outportb(COMM_BASE,CR);

/************************* ANALYZE ******/ if (!strstr(scrn_buf,"Analysis in Progress") == NULL)
  {
    puts("\377\377done/");
    return(8);
  } /* end if (!strstr(scrn_buf,"Analysis in Progress") */
  return(8);
} /* end if (!strstr(scrn_buf,"88 FLOW RATE SLOW") */ if (!strstr(scrn_buf,"9C INSUFFICIENT SAMP") == NULL)
{
  puts("\377\377error/");
  return(8);
} /* end if (!strstr(scrn_buf,"9C INSUFFICIENT SAMP") */ if (!strstr(scrn_buf,NOVA_SA) == NULL)
{
  puts("\377\377error/");
  return(8);
} /* end if (!strstr(scrn_buf,"SEQUENCE ABORTED") */

/********* CALIBRATIONS ******************/

```c
    delay(100);

outportb(COMM_BASE,DEL);

send_Nova_MIS_number = 0;

} /* end if (send_Nova_MIS_number) */ function_choice = 8;

} /* end if (!strstr(scrn_buf,"PATIENT DATA") ==
NULL) */

/**** SAMPLE ERRORS ******************/ if (!strstr(scrn_buf,"88 FLOW RATE SLOW") == NULL)
{ puts("\377\377error/");

return(0);

} /* end if (!strstr(scrn_buf,"Gas Cal in
Progress") */ if (!strstr(scrn_buf,NOVA_AGCIP) == NULL)
{ return(0);

} /* end if (!strstr(scrn_buf,"Auto_Cal in
Progress") */ if (!strstr(scrn_buf,NOVA_FCIP) == NULL)
{ return(0);

} /* end if (!strstr(scrn_buf,"Full Cal in
Progress") */ if ((!strstr(scrn_buf,NOVA_RFA) == NULL) |
```

```c
if (!strstr(scrn_buf,NOVA_GCIP) == NULL)

{ if (!send_Nova_MIS_number)

{ outportb(COMM_BASE,'D');

} return(0);

} /* end if (!strstr(scrn_buf,"Gas Cal I in

Progress") */ if (!strstr(scrn_buf,"Gas Cal in Progress") ==

NULL)

{ if (!send_Nova_MIS_number)

{ delay(3000);

get_results_from_screen_buffer();

put_results_into_database(results_tblHandle); /* put results into the results.db table */ send_Nova_MIS_number = 1;

} function_choice = 8;

} /* end if (!strstr(scrn_buf,"RESULTS READY") */ return(function_choice);

} /*                           end
check_status_of_instrument()              */

/*********************************************
```

```c
    (!strstr(scrn_buf,"SEQUENCE ABORT") == NULL))

{ return(0);

} if (!strstr(scrn_buf,"PATIENT RESULTS at") ==

NULL)

{ /* "RESULTS READY" */

/* get sample results from the screen buffer send by the Nova, must get one character at a time from a certain position in the screen buffer */

/* MIS number from Nova, starts at character 52 from the clear screen character send by the Nova at the start of each new screen */

}

/* pH, starts at character 237 to 242 */ j=0;

for (i=238;i<243;i++)

{ data.ph[j++] = *(scrn_buf+i);

}

/* PCO, starts at character 279 to 283 */ j=0;

for (i=280;i<284;i++)

{ data.pco2[j++] = *(scrn_buf+i);
```

```c
  get_results_from_screen_buffer

*****************************************/ get_results_from_screen_buffer()

{ int j,i;

j=0;

for (i=53;i<61;i++)

{ data.mis_number[j++] = *(scrn_buf+i);

}

/* BP, starts at character 121 to 126 */ j=0;

for (i=122;i<127;i++)

{ data.bp[j++] = *(scrn_buf+i);

}

/* K, starts at character 452 to 455 */ j=0;

for (i=453;i<456;i++)

{ data.k[j++] = *(scrn_buf+i);

}

/* Cl, starts at character 494 to 498 */ j=0;

for (i=494;i<499;i++)

{ data.cl[j++] = *(scrn_buf+i);
```

```c
}

/* PO, starts at character 321 to 326 */ j=0;

for (i=322;i<327;i++)

{ data.po2[j++] = *(scrn_buf+i);

}

/* Hct, starts at character 366 to 368 */ j=0;

for (i=366;i<369;i++)

{ data.hct[j++] = *(scrn_buf+i);

}

/* Na, starts at character 407 to 412 */ j=0;

for (i=408;i<413;i++)

{ data.na[j++] = *(scrn_buf+i);

put_results_into_database(TABLEHANDLE results_tblHandle)

{ long current_time;

RECORDHANDLE recHandle;

strcpy(data.device_location,"NOVA");

PXRecBufOpen(results_tblHandle,&recHandle);
```

```c
}

/* Ca, starts at character 538 to 542 */ j=0;

for (i=539;i<543;i++)

{ data.ca[j++] = *(scrn_buf+i);

}

/* Glu, starts at character 580 to 583 */ j=0;

for (i=580;i<584;i++)

{ data.gluc[j++] = *(scrn_buf+i);

}

}

/********************************************* put_results_into_database()

*********************************************/

PXPutAlpha(recHandle,FIELDTYPE,data.sample_type);
  PXPutAlpha(recHandle,FIELDFIO2,data.fio2);

PXPutAlpha(recHandle,FIELDDEVICELOCATION,data.device_location);
  PXPutAlpha(recHandle,FIELDSTATUS,"DONE");
  PXRecAppend(results_tblHandle,recHandle);
  PXRecBufClose(recHandle);
```

```
PXPutAlpha(recHandle,FIELDPATIENT,data.patient_nam-
e);

PXPutAlpha(recHandle,FIELDHISTORY,data.history_num-
ber);

PXPutAlpha(recHandle,FIELDMISNUMBER,data.mis_numbe-
r);

PXPutAlpha(recHandle,FIELDPICNUMBER,data.pic_numbe-
r);
        PXPutAlpha(recHandle,FIELDBP,data.bp);
        PXPutAlpha(recHandle,FIELDPH,data.ph);
        PXPutAlpha(recHandle,FIELDPCO,data.pco2);
        PXPutAlpha(recHandle,FIELDPO,data.po2);
        PXPutAlpha(recHandle,FIELDHCT,data.hct);
        PXPutAlpha(recHandle,FIELDNA,data.na);
        PXPutAlpha(recHandle,FIELDK,data.k);
        PXPutAlpha(recHandle,FIELDCL,data.cl);
        PXPutAlpha(recHandle,FIELDCA,data.ca);
        PXPutAlpha(recHandle,FIELDGLU,data.gluc);

PXPutAlpha(recHandle,FIELDPATIENTTEMP,data.temp);
        time(¤t_time);
        PXPutLong(recHandle,FIELDTIME,current_time);

switch(entry[2])
    { case '0':

beep(700);
```

```
}
/****** end put_results_into_database() **********/

/***********************************************
                nova_mdo()
***********************************************/
nova_mdo(int handle)
{
  int i,x = 1;
  char entry[0x10];
  long start_time,now_time;

touch(handle,"group all off",entry);
  touch(handle,"group 11 on",entry);
  puts("\377\377nova_mdo/");

do
  {
    time(&start_time);
    do
    {
      nova_display();
      touch(handle,MODE,entry);
    } while (entry[0] != 'F');

outportb(COMM_BASE,'4'); /* send
Nova an '4' */
        delay(100);
        break;

case '5':
```

```c
            outportb(COMM_BASE,'0'); /* send
Nova an '0' */ delay(100);

break;

case '1':

beep(700);

outportb(COMM_BASE,'1'); /* send
Nova an '1' */ delay(100);

break;

case '2':

beep(700);

outportb(COMM_BASE,'2'); /* send
Nova an '2' */ delay(100);

break;

case '3':

beep(700);

outportb(COMM_BASE,'3'); /* send
Nova an '3' */ delay(100);

break;

case '4':

beep(700);

outportb(COMM_BASE,'9'); /* send
Nova an '9' */ beep(700);

outportb(COMM_BASE,'5'); /* send Nova an
'5' */ delay(100);

break;

case '6':

beep(700);

outportb(COMM_BASE,'6'); /* send Nova an
'6' */ delay(100);

break;

case '7':

beep(700);

outportb(COMM_BASE,'7'); /* send Nova an
'7' */ delay(100);

break;

case '8':

beep(700);

outportb(COMM_BASE,'8'); /* send Nova an
'8' */ delay(100);

break;

case '9':

beep(700);

outportb(COMM_BASE,DEL); /* send Nova an
DEL for CLEAR */
```

```
            delay(100);

break;

case 'A':

beep(700);

outportb(COMM_BASE,'A'); /* send Nova an 'A' */ delay(100);

break;

case 'D':

beep(700);

outportb(COMM_BASE,'D'); /* send Nova an 'D' */ delay(100);

break;

case 'E':

beep(700);

outportb(COMM_BASE,CR); /* send Nova an CR for ENTER */ delay(100);

break;

case 'S':

beep(700);

outportb(COMM_BASE,'S'); /* send Nova an 'S' */ delay(100);

break;

case 'R':
```

```
            delay(100);

break;

case 'H':

beep(700);

outportb(COMM_BASE,'H'); /* send Nova an 'H' */ delay(100);

break;

case 'C':

beep(700);

outportb(COMM_BASE,'C'); /* send Nova an 'C' */ delay(100);

break;

case 'X':

beep(700);

for(i=0;i<4;i++)
            {
              delay(100);
              outportb(COMM_BASE,DEL);
            }
            delay(1000);
            x=0;
            break;
    }
} while (x);

}
```

```c
    beep(700);

/*******************************************
                beep()
********************************************/
beep(int freq)
{
 sound(freq);
 delay(75);
 nosound();
}

/*******************************************
              cursor_off()
********************************************/
cursor_off()
{
 union REGS xr;

xr.h.ah = 1;
 xr.h.ch = 0x20;
 xr.h.cl = 0;
 int86(0x10,&xr,&xr);
}

/*******************************************
                touch
********************************************/
touch(int handle, char *str, char *inbuf)
{
 char string[0x20], term[2] = {0x0d, NULL};

strcat(string, term);

if(write(handle, string, strlen(string)) == -1)
 {
  perror("write|");
  close(handle);
  exit(0);
 } if(read(handle, inbuf, 0x20) == -1)
 {
  perror("read|");
  close(handle);
  exit(0);
 } while (*pt++ != 0x0d);
 *pt = NULL;

if (inbuf[0] == 'E')
 {
  printf("ERROR - %s\n", inbuf);
 }

} /*                         touch
*/

/*******************************************
            interrupt function
********************************************/
```

```c
    char *pt;

pt = inbuf;

strcpy(string, str);

switch(flag)
{
 case NEW_STR:
    {
        temp[0] = temp[1];

temp[1] = scrn_buf[in_cnt];

switch(scrn_buf[in_cnt++] =
inportb(COMM_BASE))
        {
          case NULL:
            scrn_buf[--in_cnt] = temp[1];
            scrn_buf[--in_cnt] = temp[0];
            flag = NEW_CMD;
            break;

case CLR_SCRN:
            /* clear screen */
            setmem(scrn_buf, BUF_SIZE, SPACE);
            flag = NEW_CMD;
            break;
        }
        break;
    } void interrupt irq_func()
{
    static in_cnt = 0, flag = NEW_CMD;
    static unsigned char temp[3];
    break;

case X_AXIS:
        in_cnt += inportb(COMM_BASE);
        flag++;
        break;

case SKIP_ATTR:
        scrn_buf[in_cnt] = inportb(COMM_BASE);
        flag = 0;
        break;

case NEW_CMD:
        if(inportb(COMM_BASE) == VERT_TAB) flag = COM-
MAND;
        break;
    }
    outportb(PIC_EOI, 0x20);
}

/*************************************************
                    nova_display()
*************************************************/
nova_display()
{
```

```c
    case COMMAND:
        if(inportb(COMM_BASE) != 'C') { flag =
NEW_CMD;}
        else {flag++;}
        break;

case Y_AXIS:
        in_cnt = inportb(COMM_BASE) * WIDTH;
        flag++;
    if (!(*scrn_str & 0x80))
    {
     putch(*(scrn_str++));
    }
    else
    {
       temp[0] = (*scrn_str & 0x03) << 2; /* clear up-
per nibble */
       temp[1] = (*scrn_str & 0x30) >> 4; /* get rev
video and underline */
       temp[0] |= temp[1];
       textcolor(temp[0] + 7);
       putch(' ');
       scrn_str++;
    }
    window(1,1,80,24);
    }

/*****************************************
                view_results()
*****************************************/
```

```c
    unsigned char *scrn_str;
    int temp[2];

textbackground(BLUE);
    scrn_buf[(BUF_SIZE)] = NULL;
    window(5,6,47,25);
    scrn_str = &scrn_buf[45]; /* offset of screen */ while (*scrn_str)

textbackground(BLUE);
    textcolor(WHITE);

do
    { /* number 1 */
      do
      { /* number 2 */
        time(&start_time);
        do
        {
          touch(handle,MODE,entry);
          if (time(&now_time) > (start_time +
SCREEN_TIMEOUT))
          {
            return(0);
          }
        } while (entry[0] != 'F');

switch(entry[2])
        {
          case 'C': /* clear the display input */
```

```c
view_results(int handle,TABLEHANDLE
results_tblHandle)
{
    RECORDHANDLE recHandle;
    RECORDNUMBER recNumber=0;
    int exit=0,count=0,row=3,col=64,length=10,pxErr;
    int temp_recNumber;
    char entry[0x10],fld[11];
    long start_time,now_time;

touch(handle,"group all off",entry);
    touch(handle,"group 2 on",entry);
    puts("\377\377patresul/");

puts("\377\377patresul/");
            count=0;
            col=64;
            fld[0] = '\0';
            strcpy(fld,"          ");
            break;

case 'X':
            beep(800);
            entry[2] = 'E';
            function_choice = 0; /* set to call
logon() */
            exit = 1;
            break;

case 'A':
            beep(800);
            entry[2] = 'E';

beep(850);
            count=0;
            col=64;
            textbackground(BLACK);
            gotoxy(56,row);
            cprintf("              ");
            fld[0] = '\0';
            break;

case 'S': /* clear the display input */
            beep(750);
                touch(handle,"group all off",entry);
            touch(handle,"group 2 on",entry);
        case '9':
            beep(700);
            if (count < length)
            {
                gotoxy(col++,row);
                textbackground(BLACK);
                cprintf("%c",fld[count++] = entry[2]);
            } /* end if (count... */
            else
            {
                beep(550);
            }
            break;
        } /* end switch */

} while (entry[2] != 'E');  /* do while */ if (exit)
```

```c
            function_choice = 11;

exit = 1;

break;

case 'E':

beep(800);

break;

case '0':

case '1':

case '2':

case '3':

case '4':

case '5':

case '6':

case '7':

case '8':

PXGetAlpha(recHandle,FIELDSTATUS,7,data.status);

if (!strcmp(data.status,"ACCEPT"))

{ temp_recNumber = recNumber;

}

} /* end SEARCHFIRST */ do

{ if (pxErr =

PXSrchFld(results_tblHandle,recHandle,FIELDHISTORY,

SEARCHNEXT) == PXSUCCESS)

{
          { return(function_choice);

} fld[count]='\0';

temp_recNumber = 0;

PXRecBufOpen(results_tblHandle, &recHandle);

PXPutAlpha(recHandle,FIELDHISTORY,fld);

if (pxErr =

PXSrchFld(results_tblHandle,recHandle,FIELDHISTORY,

SEARCHFIRST) == PXSUCCESS)

{

PXRecNum(results_tblHandle,&recNumber);

PXRecGet(results_tblHandle,recHandle);

cprintf("%s",fld);

PXRecBufClose(recHandle);

} if (temp_recNumber)

{

PXRecGoto(results_tblHandle,temp_recNumber);

PXRecGet(results_tblHandle,recHandle);

PXGetAlpha(recHandle,FIELDPATIENT,21,data.patient_-
        name);

PXGetAlpha(recHandle,FIELDHISTORY,11,data.history_-
        number);
```

```
PXRecNum(results_tblHandle,&recNumber);

PXRecGet(results_tblHandle,recHandle);

PXGetAlpha(recHandle,FIELDSTATUS,7,data.status);

if (!strcmp(data.status,"ACCEPT"))

{ temp_recNumber = recNumber;

}

} /* end SEARCHNEXT */

} while (pxErr);

if (!temp_recNumber)

{ touch(handle,"group all off",entry);

touch(handle,"group 4 on",entry);

puts("\377\377noresult/");

textbackground(BLACK);

gotoxy(64,3);

PXGetAlpha(recHandle,FIELDFIO2,6,data.fio2);

PXGetAlpha(recHandle,FIELDDEVICELOCATION,6,data.device_location);

PXRecBufClose(recHandle);

touch(handle,"group all off",entry);

touch(handle,"group 3 on",entry);

puts("\377\377accept/");

textbackground(BLACK);

gotoxy(64,3);
```

```
PXGetAlpha(recHandle,FIELDMISNUMBER,11,data.mis_number);

PXGetAlpha(recHandle,FIELDPICNUMBER,6,data.pic_number);

PXGetAlpha(recHandle,FIELDBP,6,data.bp);

PXGetAlpha(recHandle,FIELDPATIENTTEMP,6,data.temp);

PXGetAlpha(recHandle,FIELDPH,7,data.ph);

PXGetAlpha(recHandle,FIELDPCO,6,data.pco2);

PXGetAlpha(recHandle,FIELDPO,6,data.po2);

PXGetAlpha(recHandle,FIELDHCT,5,data.hct);

PXGetAlpha(recHandle,FIELDNA,6,data.na);

PXGetAlpha(recHandle,FIELDK,5,data.k);

PXGetAlpha(recHandle,FIELDCL,6,data.cl);

PXGetAlpha(recHandle,FIELDCA,6,data.ca);

PXGetAlpha(recHandle,FIELDGLU,6,data.gluc);

PXGetLong(recHandle,FIELDTIME,&data.time);

PXGetAlpha(recHandle,FIELDTYPE,3,data.sample_type);

display_results()

{ gotoxy(10,7);

cprintf("%s",data.patient_name);

gotoxy(40,7);

cprintf("%s",data.mis_number);

gotoxy(56,7);

cprintf("%s",data.pic_number);

gotoxy(71,7);

cprintf("%s",data.string_time);
```

```c
        cprintf("%s",data.history_number);

textbackground(BLUE);

gotoxy(20,8);

cprintf("%s",data.patient_name);

gotoxy(20,10);

cprintf("%s",data.mis_number);

long_time_to_string(&data.time,data.string_time);

gotoxy(20,12);

cprintf("%s",data.string_time);

}

} while (!exit);  /* do while */ return(function_choice);

}
/*                 end find_history_number()
*/

/************************************************** display_results()

*************************************************/ cprintf("%s",data.temp);

gotoxy(32,19);

cprintf("%s",data.gluc);

gotoxy(67,19);

cprintf("%s",data.fio2);

}
        gotoxy(20,8);

cprintf("%s",data.history_number);

gotoxy(40,8);

cprintf("%s",data.sample_type);

gotoxy(71,8);

cprintf("%s",data.device_location);

gotoxy(32,11);

cprintf("%s",data.ph);

gotoxy(32,12);

cprintf("%s",data.pco2);

gotoxy(32,13);

cprintf("%s",data.po2);

gotoxy(32,14);

cprintf("%s",data.hct);

gotoxy(32,15);

cprintf("%s",data.na);

gotoxy(32,16);

cprintf("%s",data.k);

gotoxy(32,17);

cprintf("%s",data.cl);

gotoxy(32,18);

cprintf("%s",data.ca);

gotoxy(67,18);

{ return(0);

}

} while (entry[0] != 'F');

switch(entry[2])

{
```

```c
/*******************************************
            results_screen()
*******************************************/
results_screen(int handle,TABLEHANDLE
results_tblHandle)
{
  char entry[0x10];
  int  x=1;
  long start_time,now_time;

touch(handle,"group all off",entry);
  touch(handle,"group 12 on",entry);
  puts ("\377\377results/");

textcolor(BLACK);
  textbackground(LIGHTGRAY);

display_results();

do
  {
    time(&start_time);
    do
    { /* find first touch screen strike */
      touch(handle,MODE,entry);
      if (time(&now_time) > (start_time +
SCREEN_TIMEOUT))
      strcpy(temp.device_location,data.device_location);
        strcpy(temp.ph,data.ph);
        strcpy(temp.pco2,data.pco2);
      case 'F':
        beep(700);
        function_choice = 0;
        x = 0;
        break;

case 'R':
        break;

case 'Y':
        beep(700);
        nova_print();
        function_choice = 0;
        x = 0;
        break;

case 'P':
        beep(800);

strcpy(temp.patient_name,data.patient_name);
        strcpy(temp.mis_number,data.mis_number);
        strcpy(temp.pic_number,data.pic_number);

strcpy(temp.string_time,data.string_time);

strcpy(temp.history_number,data.history_number);

strcpy(temp.sample_type,data.sample_type);
        strcpy(data.device_location,temp.device_location);
        strcpy(data.ph,temp.ph);
        strcpy(data.pco2,temp.pco2);
```

```c
        strcpy(temp.po2,data.po2);

strcpy(temp.hct,data.hct);

strcpy(temp.na,data.na);

strcpy(temp.k,data.k);

strcpy(temp.cl,data.cl);

strcpy(temp.ca,data.ca);

strcpy(temp.temp,data.temp);

strcpy(temp.gluc,data.gluc);

strcpy(temp.fio2,data.fio2);

display_previous_results(handle,results_tblHandle);

/********************************* touch(handle,"group all off",entry);

touch(handle,"group 12 on",entry);

************************/ puts ("\377\377results/");

strcpy(data.patient_name,temp.patient_name);

strcpy(data.mis_number,temp.mis_number);

strcpy(data.pic_number,temp.pic_number);

strcpy(data.string_time,temp.string_time);

strcpy(data.history_number,temp.history_number);

strcpy(data.sample_type,temp.sample_type);
```

```c
        strcpy(data.po2,temp.po2);

strcpy(data.hct,temp.hct);

strcpy(data.na,temp.na);

strcpy(data.k,temp.k);

strcpy(data.cl,temp.cl);

strcpy(data.ca,temp.ca);

strcpy(data.temp,temp.temp);

strcpy(data.gluc,temp.gluc);

strcpy(data.fio2,temp.fio2);

display_results();

break;

} /* end switch */

} while (x);

return(function_choice);

}

/*****************************************
        display_previous_results()
*****************************************/
display_previous_results(int handle,TABLEHANDLE
results_tblHandle)
{
  int
pxErr,x=1,y=1,i,j,maximum_records,row=12,entry[0x1-
0];
```

```c
        int t=1;
        long start_time,now_time;
        RECORDHANDLE recHandle;
        RECORDNUMBER recNumber;

puts ("\377\377previous/");
        textbackground(LIGHTGRAY);
        textcolor(BLACK);

gotoxy(10,7);
        cprintf("%s",data.patient_name);
        gotoxy(40,7);
        cprintf("%s",data.mis_number);
        gotoxy(56,7);
        cprintf("%s",data.pic_number);
        gotoxy(71,7);
        cprintf("%s",data.string_time);
        gotoxy(20,8);
        cprintf("%s",data.history_number);
        gotoxy(40,8);
        cprintf("%s",data.sample_type);
        gotoxy(71,8);
        cprintf("%s",data.device_location);

gotoxy(3,10);
        cprintf("%s",data.ph);
        gotoxy(10,10);
        cprintf("%s",data.pco2);
        gotoxy(16,10);
        cprintf("%s",data.po2);

gotoxy(35,10);
        cprintf("%s",data.k);
        gotoxy(40,10);
        cprintf("%s",data.cl);
        gotoxy(46,10);
        cprintf("%s",data.ca);
        gotoxy(52,10);
        cprintf("%s",data.gluc);
        gotoxy(59,10);
        cprintf("%s",data.string_time);
        gotoxy(69,10);
        cprintf("%s",data.mis_number);

i = 0;
            PXRecBufOpen(results_tblHandle,&recHandle);

PXPutAlpha(recHandle,FIELDHISTORY,data.history_num-
        ber);

if
        (PXSrchFld(results_tblHandle,recHandle,FIELDHISTOR-
        Y,

SEARCHFIRST) == PXSUCCESS)
            {
                PXRecGet(results_tblHandle,recHandle);

PXGetAlpha(recHandle,FIELDSTATUS,7,data.status);

if (!strcmp(data.status,"ACCEPT"))
                {
                    PXRecNum(results_tblHandle,&recNumber);
```

```
gotoxy(23,10);

cprintf("%s",data.hct);

gotoxy(28,10);

cprintf("%s",data.na);

do

{ if (pxErr =
PXSrchFld(results_tblHandle,recHandle,FIELDHISTORY,
            SEARCHNEXT) == PXSUCCESS)
    {
            PXRecGet(results_tblHandle,recHandle);

PXGetAlpha(recHandle,FIELDSTATUS,7,data.status);

if (!strcmp(data.status,"ACCEPT"))
            {

PXRecNum(results_tblHandle,&recNumber);
                record[i++].record_number = recNumber;
            }
    }
} while (pxErr);

i = i - 1;

if ((i-9) <= 0)

{ maximum_records = 0;

} else

{
```

```
                record[i++].record_number = recNumber;
        }
    }

PXRecGet(results_tblHandle,recHandle);

PXGetAlpha(recHandle,FIELDMISNUMBER,11,data.mis_number);

PXGetAlpha(recHandle,FIELDPH,7,data.ph);

PXGetAlpha(recHandle,FIELDPCO,6,data.pco2);

PXGetAlpha(recHandle,FIELDPO,6,data.po2);

PXGetAlpha(recHandle,FIELDHCT,5,data.hct);

PXGetAlpha(recHandle,FIELDNA,6,data.na);

PXGetAlpha(recHandle,FIELDK,5,data.k);

PXGetAlpha(recHandle,FIELDCL,6,data.cl);

PXGetAlpha(recHandle,FIELDCA,6,data.ca);

PXGetAlpha(recHandle,FIELDGLU,6,data.gluc);

PXGetLong(recHandle,FIELDTIME,&data.time);

long_time_to_string(&data.time,data.string_time);

gotoxy(3,row);

cprintf("%-s",data.ph);

gotoxy(10,row);

cprintf("%-s",data.pco2);

gotoxy(16,row);

cprintf("%-s",data.po2);

gotoxy(23,row);

cprintf("%s",data.hct);
```

```c
      maximum_records = (i-9);
} for (j=(i-1);j>=maximum_records;j--)

{

PXRecGoto(results_tblHandle,record[j].record_number);

gotoxy(52,row);

cprintf("%s",data.gluc);

gotoxy(59,row);

cprintf("%s",data.string_time);

gotoxy(69,row++);

cprintf("%s",data.mis_number);

}

PXRecBufClose(recHandle);
/*******************************
   NOT WORKING
touch(handle,"group all off",entry);

touch(handle,"group 13 on",entry);

do

{ time(&start_time);

do

{ /* find first touch screen strike */ touch(handle,MODE,entry);

if (time(&now_time) > (start_time + SCREEN_TIMEOUT))

{
       gotoxy(28,row);

cprintf("%s",data.na);

gotoxy(35,row);

cprintf("%s",data.k);

gotoxy(40,row);

cprintf("%s",data.cl);

gotoxy(46,row);

cprintf("%s",data.ca);

} while(t);
/***********************************************/ delay(12000);

}

/***********************************************
                    idle_screen()
***********************************************/
idle_screen(int handle)

{ char entry[0x10];

touch(handle,"group all off",entry);

touch(handle,"group 10 on",entry);

puts("\377\377blank/");

textbackground(BLACK);

do

{ /* find first touch screen strike */ scrn_save();
```

```
    return(0);
}
} while (entry[0] != 'F');

switch(entry[2])

{ case 'C':

beep(700);

t=0;

} /* end switch */

}
}

/******* end program ********************/

SOURCE CODE FOR ROBOT PROGRAM

TO RUN WITH SAMPLE HANDLING PROGRAM

/**********************************************

ROBOT UIS PROGRAM (ROB_UIS.C) TO RUN WITH

SAMPLE HANDLING program (SAMHAND.C) to allow NOVA to run with the robot system with patient data saved to Paradox database, Nova communications on COM1, touch screen on COM2.

Written in Turbo C, compiled with Turbo C.

/***********************************************/ include <stdlib.h> include <ctype.h>
```

```
        touch(handle,MODE,entry);

} while (entry[0] != 'F');

switch(entry[2])

{ case 'C': /* clear the display input */ beep(700);

break;

default:

break;

define FIELDSTATUS         1 define FIELDRECEIVETIME    4 define FIELDUNIT           1 define FIELDPATIENTNAME    2 define FIELDHISTORYNUMBER  3 define FIELDPATIENT        1 define FIELDHISTORY        2 define FIELDMISNUMBER      3 define FIELDPICNUMBER      4 define FIELDTIME           5 define FIELDPATIENTTEMP    6 define FIELDTYPE           7 define FIELDFIO2           8 define FIELDSAMPLESTATUS   9 define INIT     "init"

define MODE     "mode pad"
```

```c
#include <stdio.h>
#include <conio.h>
#include <dos.h>
#include <string.h>
#include <time.h>
#include <graphics.h>
#include <fcntl.h>
#include <sys\types.h>
#include <sys\stat.h>
#include "pxengine.h"
#include "boolean.h"

#define SIZEHISTORYNUM      10
#define SIZEPATIENTNAME     20
#define SIZEUNIT            7
#define PATIENT_DATA_FILE   "c:\\satcen\\patfile.db"
#define UNIT_FILE           "d:\\tc\\unitfile.dat"
#define PIC_NUMBER_FILE     "d:\\tc\\picfile.dat"
#define MIS_NUMBER_FILE     "c:\\satcen\\recnum.db"

/*********************************************/

/*********************************************/
/* files to be used on robot station's PC */
#define PATIENT_DATA_FILE   "h:\\db\\patfile.db"
#define UNIT_FILE           "c:\\rob_uis\\unitfile.dat"
#define PIC_NUMBER_FILE     "c:\\rob_uis\\picfile.dat"
#define MIS_NUMBER_FILE     "c:\\rob_uis\\recnum.db"
/*********************************************/ define SCALE       "scale 80 24"

/*********************************************/
/* files to be used on the network */
#define UISDATA_FILE        "h:\\db\\uisdata.db"
/*********************************************/

/*************************************
#define UISDATA_FILE
"c:\\satcen\\uisdata.db"
*********************************************/
/*********************************************/
files to be used on Bill's PC */

{
    char unit[7];
    char patient_name[21];
    char history_number[10];
    char temp[5];
    char mis_number[10];
    char pic_number[6];
    char sample_type[2];
    char bp[6];
    long time;
    char fio2[6];
    char new_sample[4];
} UIS_data;

struct recc3
{
    char ward[7];
```

```c
#define SIZE       50
#define TD         1
#define DISP_CNT   16   /* max number displayed on screen at a time */
#define WD_CNT     16
#define PERIOD     '.'
define SCREEN_TIMEOUT  180 struct demog
{
  char nme[21];
  char id[10];
  char loc[7];
} pat_rec[SIZE];

struct data main()
{
  int handle,new_sample,pxErr,function_choice=0,screen_displayed=1;
  char inbuf[0xff],key;

cursor_off();

if((handle = open("TCH_SCRN", O_BINARY|O_RDONLY, S_IREAD)) == -1)
  {
    perror("driver not installed");
```

```c
} unit[SIZE];

struct picnumber
{
  char pic_number[6];
} pic_numbers[SIZE];

char MIS_number[10];

void init_list(),roledsp();

int role(),wrole();

int find_history_number(),sample_conditions();

TABLEHANDLE
uis_tblHandle,patient_tblHandle,storage_tblHandle;

/* redefine stack size */
extern unsigned _stklen = 0x2000;

pad_define_confirm(handle);
pad_define_conditions(handle);
pad_define_activate(handle);

/*****************************************
  pxErr = PXInit();
*****************************************/

/*****************************************/
  pxErr = PXNetInit("h:\\",THREECOMNET,NULL);
/*****************************************/ if (pxErr)
```

```c
  exit(0);

} close(handle);

if((handle = open("TCH_SCRN", O_BINARY|O_RDWR,

S_IWRITE)) == -1)

{ perror("driver open error");

exit(0);

}

/* set up driver functions & load pads */ touch(handle, INIT, inbuf);

touch(handle, SCALE, inbuf);

pad_define_logsc(handle);

pad_define_history(handle);

pad_define_history_accept(handle);

pad_define_history_not_found(handle);

pad_define_clear(handle);

pad_define_units(handle);

pad_define_patients(handle);

printf("Error opening uisdata.db - error: %d\n press any key",pxErr);

getch();

exit(0);

} do

{ switch(function_choice)

{
```

```c
{ printf("\n\n\n\n NOT ON THE NETWORK, ERROR:

%d",pxErr);

exit(0);

} pxErr =

PXTblOpen(PATIENT_DATA_FILE,&patient_tblHandle,0,0-

);

if (pxErr)

{ printf("Error opening patfile.db - error: %d\n press any key",pxErr);

getch();

exit(0);

} pxErr =

PXTblOpen(UISDATA_FILE,&uis_tblHandle,0,0);

if (pxErr)

{ case 6:

do

{ new_sample = check_uisdata_for_new_sample(uis_tblHandle);

if (new_sample) /* a new sample has NOT been picked up by the robot */

{
```

```c
        case 0:
                function_choice = logscrn(handle);
                break;

case 1:
                function_choice = wrole(handle);
                break;

case 2:
                function_choice =
role(handle,patient_tblHandle);
                break;

case 3:
                function_choice =
find_history_number(handle,patient_tblHandle);
                break;

case 4:
                function_choice = mis_entry(handle);
                break;

case 5:
                function_choice =
sample_conditions(handle);
                break;
        }
        } while (key != 'q');

PXTblClose(patient_tblHandle);
PXTblClose(uis_tblHandle);
                if (screen_displayed)
                {
                puts("\377\377processi/");
                screen_displayed = 0;
                }
                delay(2000);
                }
                } while (new_sample);
                function_choice = 7;
                break;

case 7:
                put_UIS_data_into_database(uis_tblHandle);
                function_choice = 0;
                break;

case 8:
                idle_screen(handle);
                function_choice = 0;
                break;

} /* end switch */ if (kbhit())
        {
        key = getch();
        {
        time(&start_time);
        do
        { /* find first touch screen strike */
        touch(handle,MODE,entry);
```

```c
/******* end main() **************/
}

/***************************************** logscrn()

*****************************************/ int logscrn (int handle)
/* display logon screen, accept logon code */
{
  char entry[0x10],fld[6];

int i,x=1,count=0,row=3,col=65,length=5;

long start_time,now_time;

load_pic_numbers();

touch(handle,"group all off",entry);

touch(handle,"group 1 on",entry);

puts("\377\377logscr/");

puts("\377\377login/");

textbackground(BLACK);

textcolor(WHITE);

strcpy(fld,"     ");

do

{ /* while(x) */ do case '4':

if (time(&now_time) > (start_time +

SCREEN_TIMEOUT))

{ return(8);

}

} while (entry[0] != 'F');

switch(entry[2])

{
      case 'C':

beep(850);

touch(handle,"group all off",entry);

touch(handle,"group 1 on",entry);

puts("\377\377login/");

textbackground(BLACK);

gotoxy(64,3);

cprintf("         ");

col = col - count;

count = 0;

strcpy (fld,"     ");

break;

case 'E':

beep(800);

break;

case '0':
      case '1':
      case '2':
      case '3':
```

```
        case '5':

case '6':

case '7':

case '8':

case '9':

beep(700);

if (count < length)

{ gotoxy(col++,row);

cprintf ("%c",(fld[count++] =
entry[2]));

} else

{ beep(550);

} /* too many input */ break;

} /* end switch */

} while (entry[2] != 'E');

if (count)

{ fld[count] = '\0';

} for (i=0;i<SIZE;i++)

{ if (!strcmp(fld,pic_numbers[i].pic_number))

{
```

```
            if (x)

{ touch(handle,"group all off",entry);

touch(handle,"group 5 on",entry);

puts("\377\377nopic/");

gotoxy(65,3);

cprintf("%s",fld);

}

} while(x);

strcpy(UIS_data.pic_number,fld);

return(1);

}

/************* end logscrn() **************/

/****************************************** picinit_list()

*******************************/ picinit_list ()

/* pic array initalization for reading files */

{ register int t;

for (t=0;t<SIZE;t++)

{

*pic_numbers[t].pic_number='\0';

}

}

/********* picinit_list() ************/
```

```c
        x=0;

}

} /* end for (i=0 ... */

/* load data from the PIC numbers file */

{ register int i;

int last;

FILE *fp;

last = 0;

if ((fp=fopen(PIC_NUMBER_FILE,"rb"))==NULL)

{ printf ("cannot open file\n");

return (0);

} picinit_list();

for (i=0,last=0;i<SIZE;i++,last++)

if (fread(&pic_numbers[i],sizeof(struct picnumber),1,fp)!=1)

{ if (feof(fp))

{ fclose(fp);

return (last - 1);

}

}

}

/******************** end load_pic_numbers()
******/

/******************************

/** load_pic_numbers() *****/ int load_pic_numbers()

textbackground(7);

for (x=b;x<=e;x++)

{ if (x==bar)

{ textbackground (6);

} gotoxy(5,row++);

cprintf(" %-7s",unit[x].ward);

textbackground(7);

}

}

/*                              end wroledsp()
*/

/********************************* winit_list()

*******************************/ void winit_list ()

{ register int t;

for (t=0;t<SIZE;t++)

{

*unit[t].ward='\0';

}
```

```
wroledsp()

*******************************/ void wroledsp (b,e,bar)

/* displays lists of wards in bar menu form */ int b,e,bar;

{ int x,row=6;

/* load data from the chosen ward demographic file
*/ char filename[32];

{ register int i;

int last;

FILE *fp;

last = 0;

if ((fp=fopen(filename,"rb"))==NULL)

{ printf ("cannot open file\n");

return (0);

} winit_list();

for (i=0,last=0;i<SIZE;i++,last++)

if (fread(&unit[i],sizeof(struct recc3),1,fp)!=1)

{ if (feof(fp))

{ fclose(fp);

return (last - 1);

}

}
```

```
}

/*******************************
    wload()
*******************************/ int wload(filename)

{ static int dsplyend;

static int wndend,recbgn,wndbgn,recend,ptr,bar;

char entry[0x10];

int function_choice,exit=0,freq=0;

long start_time,now_time;

touch(handle,"group all off",entry);

touch(handle,"group 6 on",entry);

puts ("\377\377units/");

recend = wload(UNIT_FILE);

recbgn=0;

wndbgn=0;

ptr=0;

bar=0;

dsplyend = DISP_CNT;

wndend = DISP_CNT;  /* total number of units in hospital */ textbackground(0);

textcolor(15);

gotoxy(64,3);
```

```
}
/*                          end wload()
*/

/******************************
            wrole()
******************************/
int wrole (int handle)
/* routine to read wards and display them */
    {
      return(0);
    }
  } while (entry[0] != 'F');

if ((entry[2] == 'U') || (entry[2] == 'D'))
  {
    textbackground(0);
    gotoxy(64,3);
    cprintf("         ");
  } switch(entry[2])
    {
    case 'D':
        freq = 680;
        if (ptr >= recend) beep(550);
        else
        {
            if (ptr++ >= wndend)
```

```
        cprintf("%s",unit[bar].ward);
        wroledsp (recbgn,dsplyend,bar);

do
        {
          time(&start_time);
          do
          {
            touch(handle,MODE,entry);
            if (time(&now_time) > (start_time +
SCREEN_TIMEOUT))
            {
                --wndbgn;
                --wndend;
            }
            --bar;
            wroledsp (wndbgn,wndend,bar);
          }
        break;

case 'H':
        beep(800);
        function_choice = 3; /* set to call
find_history_#() */
        exit = 1;
        break;

case 'E':
        beep(800);
        strcpy(UIS_data.unit,unit[bar].ward);
        function_choice = 2;
```

```
        {
            wndbgn++;
            wndend++;
        }
        bar++;
        wroledsp (wndbgn,wndend,bar);
    }
    break;

case 'U':
    freq = 700;
    if (ptr <= 0) beep(550);
    else
    {
        if (--ptr <= wndbgn - 1)
}

} while (!exit);

return(function_choice);

}
/*********** end wrole() ******/

/*****************************
        roledsp()
*****************************/
void roledsp (b,e,recend,bar)
/* displays lists of patients in bar menu form */
    int b,e,recend,bar;
```

```
        exit = 1;
        break;
        } /*
end switch */ if (freq)
        {
            sound(freq);
            textbackground(0);
            textcolor(15);
            gotoxy(64,3);
            cprintf("%s",unit[bar].ward);
            delay(200);
            nosound();
            freq = 0;
        }
    }
}
/******** end roledsp() ******/

/*****************************
        role()
*****************************/
int role (int handle,TABLEHANDLE patient_tblHandle)
/* routine to read *** ward (unit) *** patients and
display them */
{
    static int
dsplyend,wndend,recbgn=0,wndbgn=0,recend,ptr=0,bar=0;

int o,p,patients_in_unit=0,pxErr,exit=0;
```

```
{
    int x,count=0,row=6;
    highvideo ();
    textbackground (7);

for (x = b; x <= e; x++)
    {
        if (x==bar)
        {
            textbackground (6);
        }
        if(count++ > recend - 1)
        {
            break;
        }
        gotoxy(5,row++);
        cprintf (" %-20s           %-10s
",pat_rec[x].nme,pat_rec[x].id);
        textbackground (7);
PXGetAlpha(recHandle,FIELDHISTORYNUMBER,11,pat_rec-
[patients_in_unit].id);
        patients_in_unit++;
    } do
    {
        if(pxErr =
PXSrchFld(patient_tblHandle,recHandle,FIELDUNIT,
             SEARCHNEXT) == PXSUCCESS)
        {
            PXRecGet(patient_tblHandle,recHandle);
```

```
    long start_time,now_time;
    char
entry[0x10],*prt_o1,*prt_o2,*prt_p1,*prt_p2,*temp=-
NULL;
    int function_choice,freq=0;
    RECORDHANDLE recHandle;

PXRecBufOpen(patient_tblHandle, &recHandle);
    PXPutAlpha(recHandle,FIELDUNIT,UIS_data.unit);

if(pxErr =
PXSrchFld(patient_tblHandle,recHandle,FIELDUNIT,
             SEARCHFIRST) == PXSUCCESS)
    {
        PXRecGet(patient_tblHandle,recHandle);

PXGetAlpha(recHandle,FIELDPATIENTNAME,21,pat_rec[p-
atients_in_unit].nme);
        {
            touch(handle,"group all off",entry);
            touch(handle,"group 5 on",entry);
            puts ("\377\377nopatient/");
            gotoxy(58,14);
            textbackground(BLUE);
            cprintf(" UNIT: %s ",UIS_data.unit);
            strcpy(UIS_data.unit,"");
            strcpy(pat_rec[bar].nme,"              ");
            textbackground(BLACK);
        }
    }
    else
```

```
PXGetAlpha(recHandle,FIELDPATIENTNAME,21,pat_rec[p-
atients_in_unit].nme);

PXGetAlpha(recHandle,FIELDHISTORYNUMBER,11,pat_rec-
[patients_in_unit].id);

patients_in_unit++;

}

} while(pxErr);

PXRecBufClose(recHandle);

ptr = 0;

bar = 0;

recbgn = 0;

wndbgn = 0;

recend = patients_in_unit;

dsplyend = WD_CNT;

wndend = WD_CNT;

if (!patients_in_unit)

/* end sort names*/ touch(handle,"group all off",entry);

touch(handle,"group 7 on",entry);

puts("\377\377patients/");

gotoxy(58,14);

textbackground(BLUE);

cprintf(" UNIT: %s ",UIS_data.unit);

textcolor(WHITE);

textbackground(BLACK);
```

```
{

/******** sort the patient's name in ascending order ********/ for (o=0;o<(patients_in_unit-1);o++)

{ prt_o1 = pat_rec[o].nme;

prt_o2 = pat_rec[o].id;

for (p=o+1;p<patients_in_unit;p++)

{ prt_p1 = pat_rec[p].nme;

prt_p2 = pat_rec[p].id;

if (strcmp(prt_p1,prt_o1) < 0)

{ strcpy(temp,prt_o1);

strcpy(prt_o1,prt_p1);

strcpy(prt_p1,temp);

strcpy(temp,prt_o2);

strcpy(prt_o2,prt_p2);

strcpy(prt_p2,temp);

} /* end if (strcmp... */

} /* end for (p=o+1... */

} /* end for (o=0 ... */

{ case 'D':

freq = 680;

if (ptr >= recend - 1)

beep(550);

else

{ if(ptr++ > wndend - 1)

{
```

```
    gotoxy(56,3);

cprintf("%-20s",pat_rec[bar].nme);

roledsp(recbgn,dsplyend,recend,bar);

} do

{ time(&start_time);

do

{ touch(handle,MODE,entry);

if (time(&now_time) > (start_time +
SCREEN_TIMEOUT))

{ return(0);

}

} while (entry[0] != 'F');

if ((entry[2] == 'U') || (entry[2] == 'D'))

{ textbackground(0);

gotoxy(56,3);

cprintf("                    ");

} switch(entry[2])

beep(800);

strcpy
(UIS_data.patient_name,pat_rec[bar].nme);

strcpy
(UIS_data.history_number,pat_rec[bar].id);
```

```
                        wndbgn++;

wndend++;

} bar++ ;

roledsp
(wndbgn,wndend,recend,bar);

} break;

case 'U':

freq = 700;

if (ptr <= 0) beep(550);

else

{ if (--ptr <= wndbgn - 1)

{

--wndbgn;

--wndend;

}

--bar;

roledsp
(wndbgn,wndend,recend,bar);

} break;

case 'E':

}
/****** end role() ************/
```

```
                function_choice = 4; /*
set to call mis_entry() */ exit = 1;

break;

case 'C':

case 'X':

beep(800);

function_choice = 1; /*
set to call wrole() */ exit = 1;

break;

} /* end switch */ if (freq)
    {
      sound(freq);
      textbackground(0);
      textcolor(15);
      gotoxy(56,3);
      cprintf("%-20s",pat_rec[bar].nme);
      delay(200);
      nosound();
      freq = 0;
    }

} while (!exit);

return (function_choice);

}
```

```
/******************************
            find_history_number()
******************************/ int find_history_number(int handle,TABLEHANDLE patient_tblHandle)

{

RECORDHANDLE recHandle;

int exit=0,count=0,row=3,col=64,length=10,pxErr;

long start_time,now_time;

char entry[0x10],function_choice,fld[11];

touch(handle,"group all off",entry);

touch(handle,"group 2 on",entry);

puts("\377\377history/");

textbackground(0);

textcolor(15);

do

{ /* number 1 */ do

{ /* number 2 */ time(&start_time);

do

{ touch(handle,MODE,entry);

if (time(&now_time) > (start_time + SCREEN_TIMEOUT))

{ return(0);

function_choice = 4; /* set to call
```

```c
} while (entry[0] != 'F');

switch(entry[2])

{ case 'C': /* clear the display input */ beep(850);

count=0;

col=64;

gotoxy(56,row);

cprintf("              ");

strcpy(fld,"         ");

break;

case 'S': /* clear the display input */ beep(750);

touch(handle,"group all off",entry);

touch(handle,"group 2 on",entry);

puts("\377\377history/");

count=0;

col=64;

strcpy(fld,"         ");

break;

case 'X':

beep(800);

entry[2] = 'E';

function_choice = 1; /* set to call
wrote() */ exit = 1;

break;

case 'A':

mis_entry() */ exit = 1;

break;

case 'E':

beep(800);

break;

case '0':

case '1':

case '2':

case '3':

case '4':

case '5':

case '6':

case '7':

case '8':

case '9':

beep(700);

if (count < length)

{ gotoxy(col++,row);

cprintf("%c",fld[count++] = entry[2]);

} /* end if (count... */ else

{ beep(550);

} break;

} /* end switch */

} while (entry[2] != 'E');  /* do while */
```

```
          beep(800);

entry[2] = 'E';
{
 return(function_choice);
} fld[count]='\0';

PXRecBufOpen(patient_tblHandle, &recHandle);
   PXPutAlpha(recHandle,FIELDMISNUMBER,fld);
   pxErr =
PXSrchFld(patient_tblHandle,recHandle,FIELDMISNUMB-
ER,SEARCHFIRST);

if (!pxErr)
   {
      PXRecGet(patient_tblHandle,recHandle);

PXGetAlpha(recHandle,FIELDPATIENTNAME,21,UIS_data.-
patient_name);

PXGetAlpha(recHandle,FIELDHISTORYNUMBER,11,UIS_dat-
a.history_number);

PXGetAlpha(recHandle,FIELDUNIT,8,UIS_data.unit);
   }

PXRecBufClose(recHandle);

if (!pxErr)

{
```

```
          if (exit)

textbackground(BLUE);

gotoxy(20,8);

cprintf(" %s ",UIS_data.patient_name);

gotoxy(20,10);

cprintf(" %s ",UIS_data.unit);

} if (pxErr)

{ touch(handle,"group all off",entry);

touch(handle,"group 4 on",entry);

puts("\377\377nohistory/");

textbackground(BLACK);

gotoxy(64,3);

cprintf("%s",fld);

}

} while (!exit);   /* do while */ return(function_choice);

}
   /*                            end find_history_number()
   */

/******************************* mis_entry()

*******************************/
```

```c
touch(handle,"group all off",entry);
touch(handle,"group 3 on",entry);
puts("\377\377keypad2/");
textbackground(BLACK);
gotoxy(64,3);
cprintf("%s",UIS_data.history_number);
int pxErr,x=1,row=3,column=64,length=10;
long assign_MIS_number,start_time,now_time;
static int count=0;

strcpy(fld,"          ");

textbackground(0);
textcolor(15);

touch(handle,"group all off",entry);
touch(handle,"group 1 on",entry);
puts("\377\377mislog/");

do
{
 time(&start_time);
 do
 {
  touch(handle,MODE,entry);
  if (time(&now_time) > (start_time +
SCREEN_TIMEOUT))
  {
   return(0);
  }
 } while(entry[0] != 'F');
```

```c
int mis_entry(int handle)
{
RECORDHANDLE recHandle;
TABLEHANDLE tblHandle;
int function_choice;
char temp_MIS_number[10],entry[0x10],fld[11];
        strcpy(fld,"          ");
        break;

case 'E':
        /* accept entry as MIS id */
        beep(800);
        function_choice = 5;
        break;

case '0':
    case '1':
    case '2':
    case '3':
    case '4':
    case '5':
    case '6':
    case '7':
    case '8':
    case '9':
        beep(700);
        if (count++ < length)
        {
         gotoxy(column++,row);
         cprintf("%c",entry[2]);
/**************************************
```

```c
        switch(entry[2])
        {
            case 'C':
                /* clear calculator display */
                beep(850);
                count = 0;
                column = 64;
                gotoxy(56,row);
                cprintf("                ");
        } /* end switch */

} while (entry[2] != 'E');
    /*******************************
    for AACC meeting
    *******************************/
    count=0;

if (!count)
    {
    do
    {
      pxErr =
    PXTblOpen(MIS_NUMBER_FILE,&tblHandle,0,0);

if (!pxErr)
        { /* recnum.db database table ready of access */
          PXRecBufOpen(tblHandle, &recHandle);
          PXRecFirst(tblHandle);
          PXRecGet(tblHandle,recHandle);

PXGetAlpha(recHandle,FIELDMISNUMBER,11,MIS_number);
``` removed for use at AACC meeting, defaults to assigned MIS number

```c
            cprintf("%c",(fld[count++] = entry[2]));
    /*******************************/
        }
        else
        {
          beep(550);
        }
        break;
    if (pxErr)
    { /* storage.db database table in use, wait 2
    seconds and try again */
      PXTblClose(tblHandle);
      delay(2000);
    }
    /**************check uisdata.db for dups of entered MIS number !!!!! *****/

} while (x);

} if (count)
    {
    strcpy(MIS_number,fld); /* save MIS number in a
    safe place */
    } return(function_choice);

} /*                    end mis_entry()
```

```
strcpy(temp_MIS_number,MIS_number);

assign_MIS_number = atol(MIS_number);

assign_MIS_number++;

ltoa(assign_MIS_number,MIS_number,10);

PXPutAlpha(recHandle,FIELDMISNUMBER,MIS_number);

PXRecUpdate(tblHandle,recHandle);

PXRecBufClose(recHandle);

PXTblClose(tblHandle);

strcpy(MIS_number,temp_MIS_number);

x = 0;

} /* end if (!pxErr) */ touch(handle,"group all off",entry);

touch(handle,"group 9 on",entry);

puts ("\377\377tests1/");

textcolor(WHITE);

textbackground(BLUE);

gotoxy(21,7);

cprintf("%s",UIS_data.patient_name);

gotoxy(21,8);

cprintf("%s",UIS_data.history_number);

gotoxy(21,9);

cprintf("%s",MIS_number);

gotoxy(21,10);

cprintf("%s",UIS_data.unit);

gotoxy (6,13);

cprintf ("Patient temperature:   37.0 C");
```

```
*/

/******************************* sample_conditions()

*******************************/ int sample_conditions(int handle)

{ /* handles test and patient parameter (temp, hemo) selection */ int function_choice,exit=1;

long start_time,now_time;

char entry[0x10];

{ return(0);

}

} while (entry[0] != 'F');

textbackground(BLUE);

textcolor(WHITE);

switch(entry[2])

{ case 'V':

beep(800);

gotoxy (29,17);

if (!strcmp(UIS_data.sample_type,"A"))

{ cprintf ("venous ");

strcpy(UIS_data.sample_type,"V");

}
```

```c
    strcpy(UIS_data.temp,"37.0");

gotoxy (6,15);

cprintf ("Patient FiO2 (in %%):    RA    %%");

strcpy(UIS_data.fio2,"RA");

gotoxy (6,17);

cprintf ("Arterial or venous:    arterial");

strcpy(UIS_data.sample_type,"A");

do

{ time(&start_time);

do

{ touch(handle,MODE,entry);

if (time(&now_time) > (start_time +
SCREEN_TIMEOUT))

*************************/
      break;

case 'H':

beep(800);

/***************************** calcpd (15,handle);

touch(handle,"group all off",entry);

touch(handle,"group 9 on",entry);

puts ("\377\377tests2/");

puts ("\377\377tests9/");

puts ("\377\377tests10/");

*****************************/ break;

else

{ cprintf ("arterial");

strcpy(UIS_data.sample_type,"A");

} break;

case 'T':

beep(800);

/*********************** calcpd (13,handle);

touch(handle,"group all off",entry);

touch(handle,"group 9 on",entry);

puts ("\377\377tests2/");

puts ("\377\377tests9/");

puts ("\377\377tests10/");

cprintf ("Arterial or venous:
arterial");

strcpy (UIS_data.sample_type,"A");

textbackground(BLACK);

gotoxy(58,3);

cprintf("                    ");

break;

case 'A':

beep(800);

break;

} /* end switch */

} while (entry[2] != 'A');
```

```c
        case 'C':

beep(850);

gotoxy(21,7);

cprintf("%s",UIS_data.patient_name);

gotoxy(21,8);

cprintf("%s",UIS_data.history_number);

gotoxy(21,9);

cprintf("%s",MIS_number);

gotoxy(21,10);

cprintf("%s",UIS_data.unit);

gotoxy (6,13);

cprintf ("Patient temperature:    37.0
C");

strcpy (UIS_data.temp,"37.0");

gotoxy (6,15);

cprintf ("Patient FiO2 (in %%):    RA
%%");

strcpy (UIS_data.fio2,"RA");

gotoxy (6,17);

cprintf ("Patient temperature:    %s
C",UIS_data.temp);

gotoxy (6,15);

cprintf ("Patient FiO2 (in %%):    %s
%%",UIS_data.fio2);

if (!strcmp(UIS_data.sample_type,"A"))
            {
                gotoxy (6,17);

cprintf ("Arterial or venous:
arterial");
            }

/* confirmation screen **/ touch(handle,"group all off",entry);

touch(handle,"group 8 on",entry);

puts ("\377\377confirm/");

textcolor(WHITE);

textbackground(BLUE);

gotoxy(21,7);

cprintf("%s",UIS_data.patient_name);

gotoxy(21,8);

cprintf("%s",UIS_data.history_number);

gotoxy(21,9);

cprintf("%s",MIS_number);

gotoxy(21,10);

cprintf("%s",UIS_data.unit);

gotoxy (6,13);

beep(800);

function_choice = 0; /* set to call
logsc() */ exit = 0;

break;

case 'E':

beep(800);

function_choice = 6; /* set to call
UIS_data_into_Paradox() */ exit = 0;

break;
```

```
        else

{ gotoxy (6,17);

cprintf ("Arterial or venous:    venous
");

} do

{ time(&start_time);

do

{ touch(handle,MODE,entry);

if (time(&now_time) > (start_time +
SCREEN_TIMEOUT))

{ return(0);

}

} while (entry[0] != 'F');

switch(entry[2])

{ case 'X':

touch(handle,"group 1 on",entry);

puts ("\377\377keypad/");

puts ("\377\377keypad9/");

puts ("\377\377keypad10/");

gotoxy(col,row);

textbackground(BLACK);
```

```
        }

} while(exit);

return(function_choice);

} /*                          end
sample_conditions()                    */

/*****************************
        calcpd()
*****************************/ calcpd(int row,int handle)

/* calculator entry for patient temperature and hemoglobin in test screen */

{ char entry[0x10],fld[6];

int col=29,length=4,display_window=64;

static int count=0;

long start_time,now_time;

touch(handle,"group all off",entry);

textcolor(WHITE);

textbackground(BLACK);

gotoxy(display_window,3);

cprintf("                   ");

break;

case 'E':

/* enter */
```

```
cprintf ("__._");
strcpy(fld,NULL);

do

{ time(&start_time);
 do

{ touch(handle,MODE,entry);

if (time(&now_time) > (start_time +
SCREEN_TIMEOUT))

{ return(0);

}

} while (entry[0] != 'F');

switch(entry[2])

{ case 'C':

/* clear input */ beep(850);

count = 0;

col = 29;

strcpy(fld,NULL);

gotoxy(col,row);

cprintf("__._");

display_window = 64;

textbackground(BLUE);

gotoxy(1,1);

cprintf("%d",col);

textcolor(WHITE);

beep(800);

display_window = 64;

textcolor(WHITE);

textbackground(BLACK);

gotoxy(display_window,3);

cprintf("              ");

break;

case '0':
         case '1':
         case '2':
         case '3':
         case '4':
         case '5':
         case '6':
         case '7':
         case '8':
         case '9':

/* valid input */ beep(700);

if (count < length)

{ if (col == 31)

{ col++;

} textcolor(BLUE);

if (count)

{ fld[count] = '\0';
```

```
                textbackground(BLACK);              } gotoxy (col++,row);

cprintf ("%c",entry[2]);            if (row == 13)

{ if (display_window ==               if (!strcmp(fld,NULL))
66)
                                                    { strcpy(UIS_data.temp,"37.0");

{                                 textbackground(BLUE);

gotoxy(display_window++,3);                           gotoxy(29,row);

cprintf(".");                     cprintf("37.0");

fld[2] = PERIOD;                } count++;                        else

}                               { textbackground(BLACK);            strcpy(UIS_data.temp,fld);

} gotoxy(display_window++,3);                         } cprintf("%c",fld[count++] = entry[2]);              if (row == 15)

} /* end if (count++ <     {
length) */
                                                    if (!strcmp(fld,NULL))

{ strcpy(UIS_data.fio2,"RA");

else                              textbackground(BLUE);

{                                 gotoxy(29,row);

beep(600);                    cprintf("RA ");

} /* too many inputs */        } break;                          else

} /* end switch */                  { strcpy(UIS_data.fio2,fld);

} while(entry[2] != 'E');                   }

} touch(handle,"group all off",entry);          }
```

```
}

/******** end calcpd() *******/

/*****************************/
/*
check_uisdata_for_new_sample()
*/
/*****************************/
check_uisdata_for_new_sample(TABLEHANDLE
uis_tblHandle)
{
  RECORDHANDLE recHandle;
  int new_sample=0,pxErr;

/* uisdata.db database table ready of access */
    pxErr = PXRecBufOpen(uis_tblHandle, &recHandle);
    /* set up a record handle (recHandle) and the
record
        transfer buffer (PXRecBufOpen) */

PXRecLast(uis_tblHandle);
    PXRecGet(uis_tblHandle,recHandle);

PXGetAlpha(recHandle,FIELDSAMPLESTATUS,4,UIS_data.-
new_sample);

if (!strcmp(UIS_data.new_sample,"NEW"))
    {
      new_sample = 1;
    }
```

```
        return(new_sample);

}

/*******************************
                        put_UIS_data_into_database()
*******************************/
put_UIS_data_into_database(TABLEHANDLE
uis_tblHandle)
{
  int pxErr;
  long current_time;
  RECORDHANDLE recHandle;

strcpy(UIS_data.mis_number,MIS_number);

PXRecBufOpen(uis_tblHandle,&recHandle);

PXPutAlpha(recHandle,FIELDPATIENT,UIS_data.patient-
_name);

PXPutAlpha(recHandle,FIELDHISTORY,UIS_data.history-
_number);

PXPutAlpha(recHandle,FIELDMISNUMBER,UIS_data.mis_n-
umber);

PXPutAlpha(recHandle,FIELDPICNUMBER,UIS_data.pic_n-
umber);

time(¤t_time);

PXPutLong(recHandle,FIELDTIME,current_time);
```

```c
    PXRecBufClose(recHandle);

PXPutAlpha(recHandle,FIELDTYPE,UIS_data.sample_type);

PXPutAlpha(recHandle,FIELDFIO2,UIS_data.fio2);

PXPutAlpha(recHandle,FIELDSAMPLESTATUS,"NEW");
    PXRecAppend(uis_tblHandle,recHandle);
    PXRecBufClose(recHandle);

}
/******************************************
   end put_results_into_database() /
/******************************
        idle_screen()
******************************/
idle_screen(int handle)
{
 char entry[0x10];

touch(handle,"group all off",entry);
  touch(handle,"group 10 on",entry);
  puts("\377\377blank/");
  textbackground(BLACK);

do
           { /* find first touch screen strike */
```

```c
    PXPutAlpha(recHandle,FIELDPATIENTTEMP,UIS_data.temp);

case 'C': /* clear the display input */
          beep(700);
          break;
       } /* end switch */
}

/******************************
       scrn_save()
******************************/
scrn_save()
{
 static long last_ti;
 long ti;
 int rand_x,rand_y;
 int status_colors[] =
 {LIGHTRED,YELLOW,LIGHTGREEN,LIGHTCYAN,
          LIGHTBLUE,LIGHTMAGENTA,WHITE};

if (time(&ti) > last_ti + 1)
  {
  time(&last_ti);
  window(1,1,80,25);
  clrscr();
  rand_x = random(40) + 1;
  rand_y = random(23) + 1;
  gotoxy(rand_x,rand_y);
  textcolor(status_colors[rand_x%5]);
  cprintf("**** TOUCH SCREEN TO ACTIVATE SYSTEM
```

```
    scrn_save();

touch(handle,MODE,entry);

} while (entry[0] != 'F');

switch(entry[2])

{

/***************************** beep()

*****************************/ beep(int freq)

{ sound(freq);

delay(75);

nosound();

}

/******* cursor_off()**************/ cursor_off()

{ union REGS xr;

xr.h.ah = 1;

xr.h.ch = 0x20;

xr.h.cl = 0;

int86(0x10,&xr,&xr);

}

/***************************** touch

*****************************/
```

```
  ***");

}

} if(write(handle, string, strlen(string)) == -1)

{ perror("write|");

close(handle);

exit(0);

} if(read(handle, inbuf, 0x20) == -1)

{ perror("read|");

close(handle);

exit(0);

} while (*pt++ != 0x0d);

*pt = NULL;

if (inbuf[0] == 'E')

{ printf("ERROR - %s\n", inbuf);

}

} /*                          touch
*/
```

```
touch(int handle, char *str, char *inbuf)

{ char string[0x20], term[2] = {0x0d, NULL};

char *pt;

pt = inbuf;

strcpy(string, str);

strcat(string, term);

"pad 1 71 5 78 8 3", "pad 1 53 9 6012
4",

"pad 1 62 9 69 12 5", "pad 1 71 97812
6",

"pad 1 53 13 60 16 7", "pad 1 62 1369
16 8",

"pad 1 71 13 78 16 9", "pad 1 62
17 69 20 0",

"pad 1 53 17 60 20 C", "pad 1 71
17 78 23 E");

char ibuf[0xff];

int loop;

for (loop = 0; loop <= 11; loop++)

{ touch(handle, pads[loop], ibuf);

}

}

/*******************************
```

```
/******************************* pad_define_logsc

*******************************/ pad_define_logsc(int handle)

{

/* logsc targets */ char *pads[] = {"pad 1 53 5 60 8 1", "pad 1 62 5
69 8 2",

"pad 2 53 13 60 16 7", "pad 2 62
13 69 16 8",

"pad 2 71 13 78 16 9", "pad 2 62
17 69 20 0",

"pad 2 53 17 60 20 C", "pad 2 71
17 78 23 E",

"pad 2 53 21 60 24 X" };

char ibuf[0xff];

int loop;

for (loop = 0; loop <= 12; loop++)

{ touch(handle, pads[loop], ibuf);

}

}

/******************************* pad_define_history_accept

*******************************/
```

```
/******************************
pad_define_history
******************************/
pad_define_history(int handle)
{
    /* history number search targets */
    char *pads[] = {"pad 2 53 5 60 8 1", "pad 2 62 5 69 8 2",
                    "pad 2 71 5 78 8 3", "pad 2 53 9 60 12 4",
                    "pad 2 62 9 69 12 5", "pad 2 71 9 78 12 6",
                    }

}

/******************************
    pad_define_history_not_found
******************************/
pad_define_history_not_found(int handle)
{
    /* accept history number targets */
    char *pads[] = {"pad 4 27 19 45 23 S", "pad 4 53 21 60 24 X"};

char ibuf[0xff];
    int loop;
```

```
pad_define_history_accept(int handle)
{
    /* accept history number targets */
    char *pads[] = {"pad 3 5 19 23 23 A", "pad 3 27 19 45 23 S",
                    "pad 3 53 21 60 24 X"};

char ibuf[0xff];
    int loop;

for (loop = 0; loop <= 2; loop++)
    {
        touch(handle, pads[loop], ibuf);
        touch(handle, pads[0], ibuf);
    }
}

/******************************
    pad_define_units
******************************/
pad_define_units(int handle)
{
    /* units targets */
    char *pads[] = {"pad 6 53 5 60 8 U", "pad 6 53 21 60 24 D",
                    "pad 6 57 11 75 15 H", "pad 6 71 17 78 24 E"};

char ibuf[0xff];
    int loop;

for (loop = 0; loop <= 3; loop++)
```

```c
for (loop = 0; loop <= 1; loop++)

{ touch(handle, pads[loop], ibuf);

}

}
```

/******************************
        pad_define_clear
******************************/

```c
pad_define_clear(int handle)

{

/* logsc targets */ char *pads[] = {"pad 5 53 17 60 20 C"};

char ibuf[0xff];

"pad 7 62 21 69 24 X"};

char ibuf[0xff];

int loop;

for (loop = 0; loop <= 4; loop++)

{ touch(handle, pads[loop], ibuf);

}

}
```

/******************************
        pad_define_confirm

```c
{ touch(handle, pads[loop], ibuf);

}

}
```

/******************************
     pad_define_patients
******************************/

```c
pad_define_patients(int handle)

{

/* units targets */ char *pads[] = {"pad 7 53 5 60 8 U", "pad 7 53 21 60 24 D",

"pad 7 53 17 60 20 C", "pad 7 71 17 78 24 E", pad_define_conditions
******************************/ pad_define_conditions(int handle)

{

/* sample conditions targets */ char *pads[] = {"pad 9 1 21 16 24 T", "pad 9 18 21 34 24 H",

"pad 9 53 17 60 20 C", "pad 9 71 17 78 24 A",

"pad 9 36 21 52 24 V"};

char ibuf[0xff];

int loop;
```

```
/*******************************/ pad_define_confirm(int handle)

{

/* confirm targets */ char *pads[] = {"pad 8 53 21 60 24 X", "pad 8 71 17 78 24 E"};

char ibuf[0xff];

int loop;

for (loop = 0; loop <= 1; loop++)

{ touch(handle, pads[loop], ibuf);

}

}

/*******************************
/****** end program **********/

SOURCE CODE FOR PROGRAM FOR SATELLITE CENTRAL
    TO CHECK THE ROBOT LABORATORY RESULTS
/***********************************

SATELLITE CENTRAL (SATCEN.C) using Paradox as the
database and getting results from the server on
drive h:. Stores the number of results in a Paradox
database called recnum.db and compares that number
with the number of records currently in the
results.db database. Written with Turbo C, ver-
sion 2.0 and Paradox Engine, compiled on an IBM 80
```

```
for (loop = 0; loop <= 4; loop++)

{ touch(handle, pads[loop], ibuf);

}

}

/*******************************
      pad_define_activate
*******************************/ pad_define_activate(int handle)

{

/* logsc targets */ char *pads[] = {"pad 10 0 0 80 24 C"};

char ibuf[0xff];

touch(handle, pads[0], ibuf);

} define FIELDPATIENTTEMP    6
define FIELDPH             7
#define FIELDPCO            8
#define FIELDPO             9
#define FIELDHCT           10
#define FIELDNA            11
#define FIELDK             12
#define FIELDCL            13
#define FIELDCA            14
#define FIELDGLU           15
#define FIELDTIME          16
#define FIELDTYPE          17
```

```c
#include <stdio.h>
#include <stdlib.h>
#include <conio.h>
#include <string.h>
#include <sys\types.h>
#include <sys\stat.h>
#include <fcntl.h>
#include <pxengine.h>
#include <dos.h>
#include "boolean.h"
#include "longtime.cf"

#define FIELDRECORDNUMBER    1    /* number of
results stored in recnum.db */
#define FIELDSTATUS          1    /* sample status
in storage.db */
#define FIELDPATIENT         1
#define FIELDHISTORY         2
#define FIELDMISNUMBER       3
#define FIELDPICNUMBER       4
#define FIELDBP              5
```

```c
struct record_number
{
 int record_number;
} record[20];

struct results
{
```

```c
#define FIELDFIO2            18
#define FIELDDEVICELOCATION  19
define FIELDRESULTSTATUS    20 define INIT      "init"
define MODE      "mode pad"
#define GROUP     "group 1 on"
#define NOGROUP   "group 1 off"
#define SCALE     "scale 80 24"
#define STATUS    "status scale"
```

```c
/****************************/
#define RESULTS_FILE        "h:\\db\\results.db"
#define RECORD_NUMBER_FILE  "c:\\satcen\\recnum.db"
#define STORAGE_FILE        "h:\\db\\storage.db"
/****************************/

/***************************
#define RESULTS_FILE        "d:\\tc\\results.db"
#define RECORD_NUMBER_FILE  "c:\\satcen\\recnum.db"
#define STORAGE_FILE        "d:\\tc\\storage.db"
****************************/ char temp[5];
    char mis_number[10];
    char pic_number[6];
    char ph[7];
    char pco2[6];
    char po2[6];
    char hct[5];
    char na[6];
```

```c
    char patient_name[21];

char history_number[11];

char mis_number[11];

char pic_number[6];

char bp[6];

char temp[6];

char ph[7];

char pco2[6];

char po2[6];

char hct[5];

char na[6];

char k[5];

char cl[6];

char ca[6];

char gluc[6];

long time;

char string_time[9];

char sample_type[3];

char fio2[6];

char device_location[6];

char status[7];
} results_data;

struct data

{ char patient_name[21];

char history_number[10];

TABLEHANDLE storage_tblHandle,results_tblHandle,record_number_- tblHandle;

RECORDNUMBER previous_recNumber;

char k[5];

char cl[6];

char ca[6];

char gluc[6];

char string_time[9];

char sample_type[3];

char fio2[6];

char device_location[6];

int abort_flag;

char status[7];
} data;

struct previous

{ char ph[7];

char pco2[6];

char po2[6];

char hct[5];

char na[6];

char k[5];

char cl[6];

char ca[6];

char gluc[6];
} previous_data;

exit(0);

}

/* set up driver functions & load pads */
```

```c
/* redefine stack size */
extern unsigned _stklen = 0x2000;

/****************************/
/*         main             */
/****************************/ main()
{
 int next_record_to_get,pxErr,sample_status,new_record=0,handle;
 short record_number_in_recnum;
 char entry[0x10];
 RECORDHANDLE recHandle;
 RECORDNUMBER nRecs_results;

if((handle = open("TCH_SCRN", O_BINARY|O_RDONLY, S_IREAD)) == -1)
 {
  perror("driver not installed");
  exit(0);
 }
 close(handle);

if((handle = open("TCH_SCRN", O_BINARY|O_RDWR, S_IWRITE)) == -1)
 {
  perror("driver open error");

touch(handle, INIT,entry);
  touch(handle, SCALE,entry);
  pad_define_current_results(handle);
  pad_define_current_results_nova(handle);
  pad_define_previous_results(handle);
  pad_define_previous_key_results(handle);

/*************************************************
 pxErr = PXInit();
**********************************************/

/****************************/
 pxErr = PXNetInit("h:\\",THREECOMNET,NULL);
/****************************/ if (pxErr)
 {
  printf("\n\n\n\n                    NOT ON THE NETWORK");
  printf("\n\n                    press any key");
  getch();
  exit(0);
 } pxErr = PXTblOpen(RESULTS_FILE,&results_tblHandle,0,0);
 if (pxErr)
 {
  printf("Error opening results.db - error: %d\n press any key ",pxErr);
```

```
    getch();

exit(0);

} pxErr =
PXTblOpen(STORAGE_FILE,&storage_tblHandle,0,0);

if (pxErr)

{ printf("Error opening storage.db - error: %d\n
press any key ",pxErr);

getch();

exit(0);

} cursor_off();

do

{

PXNetTblRefresh(results_tblHandle);

PXTblNRecs(results_tblHandle,&nRecs_results);

pxErr =
PXTblOpen(RECORD_NUMBER_FILE,&record_number_tblHan-
dle,0,0);

if (pxErr)

{ printf("Error opening recnum.db - error: %d\n
press any key ",pxErr);

getch();

exit(0);

}
```

```
PXGetShort(recHandle,FIELDRECORDNUMBER,&record_num-
ber_in_recnum);

if (record_number_in_recnum < nRecs_results)

{ next_record_to_get = record_number_in_recnum
+ 1;

PXPutShort(recHandle,FIELDRECORDNUMBER,next_record-
_to_get);

PXRecUpdate(record_number_tblHandle,recHandle);

new_record = 1;

}

PXRecBufClose(recHandle);

PXTblClose(record_number_tblHandle);

if (new_record)

{ get_results(next_record_to_get,results_tblHandle);

sample_status = results_screen(handle);

change_sample_status(sample_status,storage_tblHand-
le,results_tblHandle);

textbackground(BLACK);

new_record = 0;

}
```

```
PXRecBufOpen(record_number_tblHandle,&recHandle);

PXRecGet(record_number_tblHandle,recHandle);

close(handle);

PXTblClose(results_tblHandle);

PXTblClose(storage_tblHandle);

PXExit();

}
/******   end main()  *****/

/******************************
      get_results()
******************************/
get_results(int next_record_to_get,TABLEHANDLE results_tblHandle)

{ int pxErr;

char current_results_mis_number[10];

RECORDHANDLE recHandle;

PXRecBufOpen(results_tblHandle,&recHandle);

PXRecGoto(results_tblHandle,next_record_to_get);

PXRecGet(results_tblHandle,recHandle);

PXGetAlpha(recHandle,FIELDPATIENT,21,results_data.- patient_name);
```

```
            idle_screen();

} while (!kbhit());

PXGetAlpha(recHandle,FIELDPICNUMBER,6,results_data-

.pic_number);

PXGetAlpha(recHandle,FIELDBP,6,results_data.bp);

PXGetAlpha(recHandle,FIELDPATIENTTEMP,6,results_data.temp);

PXGetAlpha(recHandle,FIELDPH,7,results_data.ph);

PXGetAlpha(recHandle,FIELDPCO,6,results_data.pco2);

PXGetAlpha(recHandle,FIELDPO,6,results_data.po2);

PXGetAlpha(recHandle,FIELDHCT,5,results_data.hct);

PXGetAlpha(recHandle,FIELDNA,6,results_data.na);

PXGetAlpha(recHandle,FIELDK,5,results_data.k);

PXGetAlpha(recHandle,FIELDCL,6,results_data.cl);

PXGetAlpha(recHandle,FIELDCA,6,results_data.ca);

PXGetAlpha(recHandle,FIELDGLU,6,results_data.gluc);

PXGetLong(recHandle,FIELDTIME,&results_data.time);

PXGetAlpha(recHandle,FIELDTYPE,3,results_data.sample_type);

PXGetAlpha(recHandle,FIELDFIO2,6,results_data.fio2-
```

```c
PXGetAlpha(recHandle,FIELDHISTORY,11,results_data.-
history_number);

PXGetAlpha(recHandle,FIELDMISNUMBER,11,results_dat-
a.mis_number);

long_time_to_string(&results_data.time,results_dat-
a.string_time);

if (!strcmp(results_data.sample_type,"R"))
    {
        PXRecBufOpen(results_tblHandle,&recHandle);

strcpy(current_results_mis_number,results_data.mis-
_number);

strcpy(data.mis_number,results_data.mis_number);

do
        {
            PXRecPrev(results_tblHandle);
            PXRecGet(results_tblHandle,recHandle);

PXGetAlpha(recHandle,FIELDMISNUMBER,11,results_dat-
a.mis_number);

} while
(strcmp(current_results_mis_number,results_data.mi-
s_number));

PXRecNum(results_tblHandle,&previous_recNumber);
```

```c
);

PXGetAlpha(recHandle,FIELDDEVICELOCATION,6,results-
_data.device_location);

PXRecBufClose(recHandle);

PXGetAlpha(recHandle,FIELDNA,6,previous_data.na);
    PXGetAlpha(recHandle,FIELDK,5,previous_data.k);

PXGetAlpha(recHandle,FIELDCL,6,previous_data.cl);

PXGetAlpha(recHandle,FIELDCA,6,previous_data.ca);

PXGetAlpha(recHandle,FIELDGLU,6,previous_data.gluc-
);

PXRecBufClose(recHandle);
    } /* end if
(!strcmp(results_data.sample_type,"R")) */

} /*                       end get_results
*/

/*******************************
            results_screen()
*******************************/
results_screen(int handle)
{
char entry[0x10];
int sample_status = 0;
```

```c
PXGetAlpha(recHandle,FIELDPH,7,previous_data.ph);

PXGetAlpha(recHandle,FIELDPCO,6,previous_data.pco2);

PXGetAlpha(recHandle,FIELDPO,6,previous_data.po2);

PXGetAlpha(recHandle,FIELDHCT,5,previous_data.hct);

touch(handle,"group all off",entry);
touch(handle,"group 1 on",entry);
} textcolor(BLACK);
textbackground(WHITE);
display_results();
print_results();

if (!strcmp(results_data.sample_type,"R"))
{
display_current_sample_previous_results();
touch(handle,"group 4 on",entry);
} do
{
  do
  { /* find first touch screen strike */
    touch(handle,MODE,entry);
  } while (entry[0] != 'F');

if (!strcmp(results_data.device_location,"NOVA"))
  {
    puts ("\377\377satcen2/");
    touch(handle,"group all off",entry);
    touch(handle,"group 2 on",entry);
  }
  else
  {
    puts ("\377\377satcen1/");
          beep(700);
          sample_status = 3;
          break;

case 'A': /* FAIL this result, but ACCEPT previous result that was a RERUN */
          beep(600);
          sample_status = 4;
          break;

case 'P': /* display previous ACCEPTed results for this history number */
          beep(800);

strcpy(data.patient_name,results_data.patient_name);

strcpy(data.mis_number,results_data.mis_number);

strcpy(data.pic_number,results_data.pic_number);

strcpy(data.string_time,results_data.string_time);
```

```c
switch(entry[2])
{
    case 'F': /* FAIL this result */
        beep(700);
        sample_status = 1;
        break;

case 'R': /* RERUN this result */
        beep(700);
        sample_status = 2;
        break;

case 'Y': /* ACCEPT this result */
            strcpy(data.k,results_data.k);
            strcpy(data.cl,results_data.cl);
            strcpy(data.ca,results_data.ca);
            strcpy(data.temp,results_data.temp);
            strcpy(data.gluc,results_data.gluc);
            strcpy(data.fio2,results_data.fio2);

puts ("\377\377previous/");

display_previous_results(handle,results_tblHandle);

if
(!strcmp(results_data.device_location,"NOVA"))
                {
                puts ("\377\377satcen2/");
                touch(handle,"group all
off",entry);

strcpy(data.history_number,results_data.history_number);

strcpy(data.sample_type,results_data.sample_type);

strcpy(data.device_location,results_data.device_location);
                strcpy(data.ph,results_data.ph);
                strcpy(data.pco2,results_data.pco2);
                strcpy(data.po2,results_data.po2);
                strcpy(data.hct,results_data.hct);
                strcpy(data.na,results_data.na);
                } strcpy(results_data.patient_name,data.patient_name);

strcpy(results_data.mis_number,data.mis_number);

strcpy(results_data.pic_number,data.pic_number);

strcpy(results_data.string_time,data.string_time);

strcpy(results_data.history_number,data.history_number);

strcpy(results_data.sample_type,data.sample_type);

strcpy(results_data.device_location,data.device_location);
```

```
                touch(handle,"group 2 on",entry);

} else

{ puts ("\377\377satcen1/");

touch(handle,"group all
off",entry);

touch(handle,"group 1 on",entry);

if
(!strcmp(results_data.sample_type,"R"))

{ display_current_sample_previous_results();

touch(handle,"group 4
on",entry);

}

} /* end switch */

} while (!sample_status);

return(sample_status);

}

/******* display_results()  *******/ display_results()

{ gotoxy(10,7);

cprintf("%s",results_data.patient_name);
```

```
    strcpy(results_data.ph,data.ph);

strcpy(results_data.pco2,data.pco2);

strcpy(results_data.po2,data.po2);

strcpy(results_data.hct,data.hct);

strcpy(results_data.na,data.na);

strcpy(results_data.k,data.k);

strcpy(results_data.cl,data.cl);

strcpy(results_data.ca,data.ca);

strcpy(results_data.temp,data.temp);

strcpy(results_data.gluc,data.gluc);

strcpy(results_data.fio2,data.fio2);

textcolor(BLACK);

display_results();

break;

gotoxy(32,15);

cprintf("%s",results_data.na);

gotoxy(32,16);

cprintf("%s",results_data.k);

gotoxy(32,17);

cprintf("%s",results_data.cl);

gotoxy(32,18);

cprintf("%s",results_data.ca);

gotoxy(67,18);

cprintf("%s",results_data.temp);

gotoxy(32,19);

cprintf("%s",results_data.gluc);

gotoxy(67,19);

cprintf("%s",results_data.fio2);
```

```c
gotoxy(40,7);

cprintf("%s",results_data.mis_number);

gotoxy(56,7);

cprintf("%s",results_data.pic_number);

gotoxy(71,7);

cprintf("%s",results_data.string_time);

gotoxy(20,8);

cprintf("%s",results_data.history_number);

gotoxy(40,8);

cprintf("%s",results_data.sample_type);

gotoxy(71,8);

cprintf("%s",results_data.device_location);

gotoxy(32,11);

cprintf("%s",results_data.ph);

gotoxy(32,12);

cprintf("%s",results_data.pco2);

gotoxy(32,13);

cprintf("%s",results_data.po2);

gotoxy(32,14);

cprintf("%s",results_data.hct);

gotoxy(47,15);

cprintf("%s",previous_data.na);

gotoxy(47,16);

cprintf("%s",previous_data.k);

gotoxy(47,17);

cprintf("%s",previous_data.cl);

gotoxy(47,18);

cprintf("%s",previous_data.ca);

gotoxy(47,19);

cprintf("%s",previous_data.gluc);

}

/*************************************
display_current_sample_previous_results(), for RERUNs
*************************************/ display_current_sample_previous_results()

{ textcolor(LIGHTBLUE);

textbackground(LIGHTGRAY);

gotoxy(45,10);

cprintf("PREVIOUS RESULTS");

gotoxy(47,11);

cprintf("%s",previous_data.ph);

gotoxy(47,12);

cprintf("%s",previous_data.pco2);

gotoxy(47,13);

cprintf("%s",previous_data.po2);

gotoxy(47,14);

cprintf("%s",previous_data.hct);

gotoxy(40,8);

cprintf("%s",results_data.sample_type);

gotoxy(71,8);

cprintf("%s",results_data.device_location);

gotoxy(3,10);

cprintf("%s",results_data.ph);

gotoxy(10,10);

cprintf("%s",results_data.pco2);

gotoxy(16,10);
```

```c
puts("\377\377preresul/");

}

/*** display_previous_results() ********/ display_previous_results(int handle,TABLEHANDLE results_tblHandle)

{ int pxErr,i,j,maximum_records,row=12,entry[0x10];

RECORDHANDLE recHandle;

RECORDNUMBER recNumber;

textbackground(LIGHTGRAY);

textcolor(BLACK);

gotoxy(10,7);

cprintf("%s",results_data.patient_name);

gotoxy(40,7);

cprintf("%s",results_data.mis_number);

gotoxy(56,7);

cprintf("%s",results_data.pic_number);

gotoxy(71,7);

cprintf("%s",results_data.string_time);

gotoxy(20,8);

cprintf("%s",results_data.history_number);

if
  (PXSrchFld(results_tblHandle,recHandle,FIELDHISTORY,

SEARCHFIRST) == PXSUCCESS)

{

PXRecGet(results_tblHandle,recHandle);

cprintf("%s",results_data.po2);

gotoxy(23,10);

cprintf("%s",results_data.hct);

gotoxy(28,10);

cprintf("%s",results_data.na);

gotoxy(35,10);

cprintf("%s",results_data.k);

gotoxy(40,10);

cprintf("%s",results_data.cl);

gotoxy(46,10);

cprintf("%s",results_data.ca);

gotoxy(52,10);

cprintf("%s",results_data.gluc);

gotoxy(59,10);

cprintf("%s",results_data.string_time);

gotoxy(69,10);

cprintf("%s",results_data.mis_number);

i = 0;

PXRecBufOpen(results_tblHandle,&recHandle);

PXPutAlpha(recHandle,FIELDHISTORY,results_data.history_number);

PXRecNum(results_tblHandle,&recNumber);
            record[i++].record_number = recNumber;
    }
}
```

```
PXGetAlpha(recHandle,FIELDRESULTSTATUS,7,results_d-
ata.status);

if
(!strcmp(results_data.status,"ACCEPT"))

{

PXRecNum(results_tblHandle,&recNumber);

record[i++].record_number = recNum-
ber;

}
    } do
    {
    if (pxErr =
PXSrchFld(results_tblHandle,recHandle,FIELDHISTORY,

SEARCHNEXT) == PXSUCCESS)

{

PXRecGet(results_tblHandle,recHandle);

PXGetAlpha(recHandle,FIELDRESULTSTATUS,7,results_d-
ata.status);

if
(!strcmp(results_data.status,"ACCEPT"))

{

PXGetAlpha(recHandle,FIELDK,5,results_data.k);

PXGetAlpha(recHandle,FIELDCL,6,results_data.cl);
```

```
    } while (pxErr);

if ((i-9) <= 0)
    {
      maximum_records = 0;
    }
    else
    {
      maximum_records = (i-9);
    } for (j=(i-1);j>=maximum_records;j--)
    {

PXRecGoto(results_tblHandle,record[j].record_numbe-
r);

PXRecGet(results_tblHandle,recHandle);

PXGetAlpha(recHandle,FIELDMISNUMBER,11,results_dat-
a.mis_number);

PXGetAlpha(recHandle,FIELDPH,7,results_data.ph);

PXGetAlpha(recHandle,FIELDPCO,6,results_data.pco2);

PXGetAlpha(recHandle,FIELDPO,6,results_data.po2);

PXGetAlpha(recHandle,FIELDHCT,5,results_data.hct);

PXGetAlpha(recHandle,FIELDNA,6,results_data.na);

PXRecBufClose(recHandle);
```

```c
PXGetAlpha(recHandle,FIELDCA,6,results_data.ca);

PXGetAlpha(recHandle,FIELDGLU,6,results_data.gluc);

PXGetLong(recHandle,FIELDTIME,&results_data.time);

long_time_to_string(&results_data.time,results_data.string_time);

gotoxy(3,row);
    cprintf("%-s",results_data.ph);
    gotoxy(10,row);
    cprintf("%-s",results_data.pco2);
    gotoxy(16,row);
    cprintf("%-s",results_data.po2);
    gotoxy(23,row);
    cprintf("%s",results_data.hct);
    gotoxy(28,row);
    cprintf("%s",results_data.na);
    gotoxy(35,row);
    cprintf("%s",results_data.k);
    gotoxy(40,row);
    cprintf("%s",results_data.cl);
    gotoxy(46,row);
    cprintf("%s",results_data.ca);
    gotoxy(52,row);
    cprintf("%s",results_data.gluc);
    gotoxy(59,row);
    cprintf("%s",results_data.string_time);
    gotoxy(69,row++);

/***************************************
    touch(handle,"group all off",entry);
    touch(handle,"group 3 on",entry);

do
    {
      do
      { /* find first touch screen strike */
        touch(handle,MODE,entry);
      } while (entry[0] != 'F');

switch(entry[2])
      {
        case 'C':
          beep(700);

} /* end switch */

} while(entry[2] != 'C');
****************************************/
    delay(15000);

}

/****** change_sample_status()*********/
change_sample_status(int sample_status,TABLEHANDLE storage_tblHandle,
                     TABLEHANDLE results_tblHandle)
{
int pxErr;
```

```
      cprintf("%s",results_data.mis_number);

} if (!strcmp(results_data.device_location,"ROBOT"))

{ /* change STATUS in storage.db if results from a robot lab */

PXRecBufOpen(storage_tblHandle,&recHandle);

PXPutAlpha(recHandle,FIELDMISNUMBER,results_data.m- is_number);

if (pxErr =

PXSrchFld(storage_tblHandle,recHandle,FIELDMISNUMB-

ER,

SEARCHFIRST) == PXSUCCESS)

{

PXRecGet(storage_tblHandle,recHandle);

switch(sample_status)

{ case 1:

/* change status code STAT/PENDING to

ERROR */

PXPutAlpha(recHandle,FIELDSTATUS,"ERROR");

break;

case 2:

/* change status code STAT/PENDING to
```

```
         RECORDHANDLE recHandle;

RECORDNUMBER CurrentRecordNumber,LastRecordNumber;

case 4:

/* change status code REPEAT to DIS-

CARD */

PXPutAlpha(recHandle,FIELDSTATUS,"DISCARD");

break;

} /* end switch */

PXRecUpdate(storage_tblHandle,recHandle);

} /* end SEARCHFIRST */

PXRecBufClose(recHandle);

} /* end if (strcmp(results_data.device_location,"ROBOT")) */

/*********** set result status (ACCEPT, FAIL,

RERUN) in results.db *********/

PXRecBufOpen(results_tblHandle,&recHandle);

PXPutAlpha(recHandle,FIELDMISNUMBER,results_data.m- is_number);

if
```

```
REPEAT */                              (PXSrchFld(results_tblHandle,recHandle,FIELDMISNUM-
                                       BER,
PXPutAlpha(recHandle,FIELDSTATUS,"REPEAT");
                                               SEARCHFIRST) == PXSUCCESS)
        break;
                                       {
    case 3:
                                       PXRecNum(results_tblHandle,&LastRecordNumber);
        PXRecGet(results_tblHandle,recHandle);
                                               break;

PXGetAlpha(recHandle,FIELDRESULTSTATUS,6,data.stat-    } /* end switch */
us);
                                       } /* end if (!strcmp(data.status,"DONE"))
                                       */ if (!strcmp(data.status,"DONE"))

{ /* if first mis number found is DONE, change status code */                  else switch(sample_status)          { /* if first find of mis number is not DONE, con-
                                       tinue search */
        { case 1:                            do

/* change result status code to    { /* search until a DONE is found for mis number
FAIL */                                */ if

PXPutAlpha(recHandle,FIELDRESULTSTATUS,"FAIL");    (PXSrchFld(results_tblHandle,recHandle,FIELDMISNUM-
                                                   BER, PXRecUpdate(results_tblHandle,recHandle);              SEARCHNEXT) == PXSUCCESS)

break;                             { case 2:                            PXRecNum(results_tblHandle,&CurrentRecordNumber);

/* change result status code to    PXRecGet(results_tblHandle,recHandle);
RERUN */

PXGetAlpha(recHandle,FIELDRESULTSTATUS,6,data.stat-
PXPutAlpha(recHandle,FIELDRESULTSTATUS,"RERUN");   us);

PXRecUpdate(results_tblHandle,recHandle);          if (!strcmp(data.status,"RERUN"))
```

```c
        break;

case 3:
        /* change result status code to
ACCEPT */

PXPutAlpha(recHandle,FIELDRESULTSTATUS,"ACCEPT");

PXRecUpdate(results_tblHandle,recHandle);

case 1:
        /* change result status code to FAIL*/

PXPutAlpha(recHandle,FIELDRESULTSTATUS,"FAIL");

PXRecUpdate(results_tblHandle,recHandle);

PXRecGoto(results_tblHandle,LastRecordNumber);

PXPutAlpha(recHandle,FIELDRESULTSTATUS,"FAIL");

PXRecUpdate(results_tblHandle,recHandle);
        break;

case 2:
        /* change result status code to
RERUN */

PXPutAlpha(recHandle,FIELDRESULTSTATUS,"RERUN");

PXRecUpdate(results_tblHandle,recHandle);

{

PXRecNum(results_tblHandle,&LastRecordNumber);
        }
    }
} while (strcmp(data.status,"DONE"));

switch(sample_status)
{

PXRecUpdate(results_tblHandle,recHandle);

PXRecGoto(results_tblHandle,LastRecordNumber);

PXRecGet(results_tblHandle,recHandle);

PXPutAlpha(recHandle,FIELDRESULTSTATUS,"FAIL");

PXRecUpdate(results_tblHandle,recHandle);

break;

case 4:
        /* change previous result status code
to ACCEPT */

PXPutAlpha(recHandle,FIELDRESULTSTATUS,"FAIL");

PXRecUpdate(results_tblHandle,recHandle);

PXRecGoto(results_tblHandle,LastRecordNumber);

PXRecGet(results_tblHandle,recHandle);
```

```c
PXRecGoto(results_tblHandle,LastRecordNumber);

PXPutAlpha(recHandle,FIELDRESULTSTATUS,"FAIL");

PXRecUpdate(results_tblHandle,recHandle);

break;

case 3:

/* change result status code to
ACCEPT */

PXPutAlpha(recHandle,FIELDRESULTSTATUS,"ACCEPT");

PXRecBufClose(recHandle);

} /*              end
change_sample_status()          */

/****** idle screen() *********/
idle_screen()

{ int random_row,random_column,random_color;

delay(500);

clrscr();

randomize();

random_row = random(60);

random_column = random(23);

random_color = random(16);

PXPutAlpha(recHandle,FIELDRESULTSTATUS,"ACCEPT");

PXRecUpdate(results_tblHandle,recHandle);

break;

} /* end switch */

} /* end else */

} /* end if
(PXSrchFld(results_tblHandle,recHandle,FIELDMISNUM-

BER */ cursor_off()

{ union REGS xr;

xr .h.ah = 1;

xr .h.ch = 0x20;

xr .h.cl = 0;

int86(0x10,&xr,&xr);

}

/********** touch *******/
touch(int handle, char *str, char *inbuf)

{ char string[0x20], term[2] = {0x0d, NULL};

char *pt;

pt = inbuf;

strcpy(string, str);
```

```c
  if (random_color < 9)
  {
    if (random_color < 7)
    {
      random_color = random_color + 9;
    }
    else
    {
      random_color = random_color + 7;
    }
  }
  gotoxy(random_row,random_column);
  textcolor(random_color);
  cprintf("*** SYSTEM IDLE ***",random_color);
} if (inbuf[0] == 'E')
  {
    printf("ERROR - %s\n", inbuf);
  }

} /*                    touch
*/

/****** pad_define_current_results **********/
pad_define_current_results(int handle)
{
/* satcen1 targets */
  char *pads[] = {"pad 1 0 0 19 3 P", "pad 1 64 22
80 24 F",
```

```c
    strcat(string, term);

if(write(handle, string, strlen(string)) == -1)
    {
      perror("write|");
      close(handle);
      exit(0);
    } if(read(handle, inbuf, 0x20) == -1)
    {
      perror("read|");
      close(handle);
      exit(0);
    } while (*pt++ != 0x0d);
    *pt = NULL;

touch(handle, pads[0], ibuf);

}

/***** pad_define_current_results_nova *******/
pad_define_current_results_nova(int handle)
{
/* satcen1 targets */
  char *pads[] = {"pad 2 0 0 19 3 P", "pad 2 64 22
80 24 F",
          "pad 2 0 22 14 24 Y"};

char ibuf[0xff];
  int loop;
```

"pad 1 0 22 14 24 Y", "pad 1 31 22 46 24 R");

```c
char ibuf[0xff];
int loop;

for (loop = 0; loop < 4; loop++)
{
  touch(handle, pads[loop], ibuf);
}

}
```

/*** pad_define_previous_key_results ****/
```c
pad_define_previous_key_results(int handle)
{
/* satcen1 targets */
char *pads[] = {"pad 4 55 11 74 14 A"};

char ibuf[0xff];
```
/****** beep() ******************/
```c
beep(int freq)
{
  sound(freq);
  delay(75);
  nosound();
}
```

/*******************************
       print_results()
*******************************/

```c
for (loop = 0; loop < 3; loop++)
{
  touch(handle, pads[loop], ibuf);
}

}
```

/*****************************
pad_define_previous_results
****************************/
```c
pad_define_previous_results(int handle)
{
/* satcen1 targets */
char *pads[] = {"pad 3 59 0 80 3 C"};

char ibuf[0xff];

touch(handle, pads[0], ibuf);
}
```

```c
fprintf (pr,"      ANALYSIS TIME: %s\n",results_data.string_time);
fprintf (pr,"      PIC NUMBER: %s\n",results_data.pic_number);
fprintf (pr,"      LOCATION: %s\n\n",results_data.device_location);
fprintf (pr,"            pH: %s\n",results_data.ph);
fprintf (pr,"          PCO2: %s mmHg\n",results_data.pco2);
fprintf (pr,"           PO2: %s
```

```c
print_results()

{

FILE *pr;

pr = fopen ("PRN","w");

printer_status();

fprintf(pr,"%c%c%c",0x1B,0x43,0x00,0x0B);/* paper length to 11" */ fprintf
(pr,"------------------------------------------------------------\n\n");

if (!strcmp(results_data.sample_type,"R"))

{ fprintf(pr,"            **** REPEATED RESULTS ****\n\n");

} fprintf (pr,"   PATIENT NAME: %s\n",results_data.patient_name);

fprintf (pr,"   HISTORY NUMBER: %s\n",results_data.history_number);

fprintf (pr,"   MIS NUMBER: %s\n",results_data.mis_number);

/*  check the status of the printer, display errors
        if a problem, error codes only for an Okidata
        Microline 192 Plus printer.
    ****************************/ printer_status()

{ int printer_status=1;
```

```c
                mmHg\n",results_data.po2);

fprintf (pr,"             hct: %s %\n",results_data.hct);

fprintf (pr,"             Na: %s mmol/L\n",results_data.na);

fprintf (pr,"             K: %s mmol/L\n",results_data.k);

fprintf (pr,"             Cl: %s mmol/L\n",results_data.cl);

fprintf (pr,"             Ca++: %s mg/dl\n",results_data.ca);

fprintf (pr,"             Glucose: %s mg/dl\n",results_data.gluc);

fprintf
(pr,"------------------------------------------------------------\n\n");

fprintf (pr,"\n\n\n\n\n\n");

fclose (pr);

}

/***************************** break;

}

} /* end switch */

} /* end while */ gotoxy(24,3);

cprintf("
```

```
textbackground(BLACK);

textcolor(LIGHTRED + BLINK);

while (printer_status != 144)

{ printer_status = biosprint(2,' ',0);

switch (printer_status)

{ case 0:

{ gotoxy(24,3);

cprintf(" Printer off line, press
SELECT on printer.");

break;

} case 40:

{ gotoxy(24,3);

cprintf(" Printer out of paper, add
paper.");

break;

} case 72:

{ gotoxy(24,3);

cprintf(" Printer is off, turn
printer on.");
```

```
");

} /* end printer_status() function */

/******  end program   ********************/
```

What is claimed is:

1. A method of analyzing a plurality of sample specimens, each contained within a syringe using a computerized robotic system having:

at least one computer, said at least one computer having a database capable of receiving information from sensors, transmitting information to a power means within said system, maintaining and transmitting test data to a remote second location based on an input from an analytical instrument within said system;

a specimen receiving station, said specimen receiving station having a syringe receiving area and a plurality of sensors within said syringe receiving area, said sensors indicating the presence or lack of presence of a syringe in said syringe receiving area;

a refrigerated, specimen storage unit, said specimen storage unit having;
- a specimen holding area, said specimen holding area having a plurality of specimen holding means being recessed from a table surface,
- each of said plurality of specimen holding means having an individual identification code registered within said database,
- said plurality of specimen holding means being rotatable at a rate and for a length of time which is determined by said computer, said rotation commencing at the time of placing a first sample specimen syringe into one of said plurality of specimen holding means,
- said refrigerated specimen storage unit maintaining an essentially constant, preset temperature for a period of time, a plurality of syringes, each of said plurality of syringes having a syringe cap and containing a substance to be analyzed, each syringe being given a syringe identification code within said database to trace said syringe from receipt in said specimen receiving station to disposal, decapping means, said decapping means comprising:
- a decapping area, said decapping area having a plurality of sensors, said sensors recognizing the presence or lack of presence of a syringe and syringe cap,
- a cap receiving area, said cap receiving area being dimensioned to receive a syringe,
- a gripping device, said gripping device being dimensioned to receive a narrow portion of said syringe cap and being moved by a power source,
- power means, said power means moving said gripping device in response to commands from said computer, an analytical instrument, said analytical instrument having:
- syringe analysis means,
- sensor means, said sensor means being proximate said syringe analysis means to indicate the presence or lack of presence of a syringe, a robot, said robot having
- a movable arm and
- at least one pair of specimen gripping means, said at least one pair of specimen gripping means being attached to said movable arm and having sensors, said sensors indicating the presence or absence of a syringe, wherein said movable arm moves said gripping means between a plurality of locations, including at least said specimen receiving station, said refrigerated specimen storage unit, said decapping means and said analytical instrument, said robot receiving commands from at least one of said at least one computer to grasp, release and move said sample specimen syringe;

comprising the steps of:
a- placing a first of a plurality of sample specimen syringes in said syringe receiving area of said specimen receiving station, thereby activating said sensors therein and notifying said database of the presence of said first syringe, b- assigning aid first syringe a syringe identification code in said database, c- said database commanding said robot to move to said specimen receiving station, d- said robot notifying said database when said specimen gripping means are in position to grasp said first syringe, e- said database commanding said specimen gripping means to close around said first syringe, said sensors registering the proximity of said syringe and sending said proximity to said database until said database commands said specimen gripping means to cease closing at a predetermined proximity, f- said database checking said specimen storage unit to determine which of said plurality of specimen holding means is vacant and memorizing its individual identification code and rotating said specimen storage unit to a position which is accessible to said robot;

g- said database commanding said robot to move said first syringe from said sample receiving station to the vacant specimen holding means corresponding to said specimen holding means individual identification code, h- said robot releasing said first syringe and notifying said database of the time of placing said sample in said vacant specimen holding means, i- said database determining a next sample specimen syringe to be analyzed and relaying a next syringe identification code to said specimen holding means, causing said specimen holding means to rotate such that said next syringe is accessible to said robot, j- said database commanding said robot to remove said next syringe from said specimen storage unit by transmitting the specimen holding means identification code of said next syringe to said robot, k- said robot arm moving to said specimen holding means, repeating step (e), and removing said next syringe, said sample specimen storage unit continuing rotation after removal of said syringe, l- robotically transferring said next sample specimen syringe from said specimen holding means to said decapping means and notifying said database that said gripping means are located in position over said decapping means, m- said database commanding said gripping device of said decapping means to be in a position to receive said syringe and said syringe cap, n- upon verification that said gripping means is in a position to receive said next syringe and syringe cap, said database commands said robot to place said next syringe into said decapping means until said decapping mans sensors notify said database that said syringe cap is positioned in said cap receiving area and that a syringe is present, o- said database commanding said power means to activate said gripping device to move into a position to lock said syringe cap in said cap receiving area, p- said database checking said analytical instrument to determine if said analytical instrument is ready to analyze said next syringe and receiving from said analytical instrument a proceed or hold signal, q- repeating step (p) until said analytical instrument sends said proceed signal, r- said database notifying said analytical instrument that said next syringe is being transferred and commanding said robot to remove said next syringe from said decapping means, said syringe cap being retained in said cap receiving area by said gripping device, s- said database commanding said robot to remove said next syringe from said decapping means and place said next syringe in said syringe analysis means of said analytical instrument, said sensor means in said syringe analysis means notifying said database when said next syringe is positioned within said syringe analysis means, t- said database commanding said movable arm to hold said next syringe proximate said analytical instrument and then commanding said analytical instrument to withdraw an aliquot of said substance contained within said next syringe into said analytical instrument, u- said analytical instrument notifying said database when said aliquot has been withdrawn, v- said database commanding said robot to remove said next syringe from said analytical instrument and return said syringe to said decapping means, w- said database verifying said syringe cap is in position within said cap receiving area to recap said syringe and, once verification is received, commanding said robot to place said next syringe into said decapping means until said sensors transmit to said database that said cap is locked onto said next syringe, x- said database commanding said gripping device to release said syringe cap, y- said database commanding said robot to repeat step (e) and lift said next syringe from said decapping means, move said next syringe to a storage area and place said next syringe in said storage area, the location in said storage area being given a storage area code, z- transferring test results obtained from the analysis of said next syringe with said syringe identification code to a computer at a remote second location through a computer data transfer link, said test results being viewed and an acceptance or rejection issued by a technologist at said remote second location, aa- said database receiving said acceptance or rejection of each of said syringes tested, said acceptance or rejection corresponding to said syringe identification code, bb- said database responding to an acceptance of said test results by commanding said robot to dispose of said syringe and entering into the database that said syringe was disposed of, cc- said database responding to a rejection of said test results by repeating steps i-bb, dd- repeating steps i-cc, until all syringes are tested, ee- repeating steps a-cc upon activation of said specimen receiving station sensors.

2. The method of claim 1 wherein said syringe in step (j) is chosen based on preset criteria programmed into the database, 3. The method of claim 2 wherein preset criteria in step (j) is based on the age of the sample.

4. The method of claim 1 wherein said syringe is chosen based on a user entered request.

5. The method of claim 1 wherein said specimen storage unit is maintained at a temperature substantially below ambient temperature in order to preserve said substance.

6. The method of claim 1 wherein said refrigerated specimen storage unit further comprises a door and opening/closing means said opening/closing means being activated by said database.

7. The method of claim 1 wherein said specimen storage unit is said specimen holding area.

* * * * *

UNITED STATES PATENT AND TRADEMARK OFFICE
CERTIFICATE OF CORRECTION

PATENT NO. : 5,366,896  Page 1 of 1
DATED : November 22, 1994
INVENTOR(S) : Keith S. Margrey et al.

It is certified that error appears in the above-identified patent and that said Letters Patent is hereby corrected as shown below:

Column 1,
Line 4, the following paragraph is inserted immediately following the title:
-- U.S. Government Rights
This invention was made with the United States Government support under Grant No. HL62211, awarded by the National Institutes of Health. The United States Government has ceartin rights in the invention. --

Signed and Sealed this

Sixth Day of July, 2004

JON W. DUDAS
*Acting Director of the United States Patent and Trademark Office*